United States Patent
Chan et al.

(10) Patent No.: US 11,633,460 B2
(45) Date of Patent: *Apr. 25, 2023

(54) INJECTABLE SOLUTION AT PH 7 COMPRISING AT LEAST ONE BASAL INSULIN WHEREIN THE PI IS COMPRISED FROM 5.8 TO 8.5 AND A CO-POLYAMINO ACID BEARING CARBOXYLATE CHARGES AND HYDROPHOBIC RADICALS

(71) Applicant: ADOCIA, Lyons (FR)

(72) Inventors: You-Ping Chan, Ternay (FR);
Alexandre Geissler, Lyons (FR);
Romain Noel, Villeurbanne (FR);
Walter Roger, Lyons (FR); Richard Charvet, Rillieux La Pape (FR);
Nicolas Laurent, Miribel (FR)

(73) Assignee: ADOCIA, Lyons (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/213,748

(22) Filed: Dec. 7, 2018

(65) Prior Publication Data

US 2019/0275115 A1 Sep. 12, 2019

Related U.S. Application Data

(60) Provisional application No. 62/606,138, filed on Dec. 7, 2017.

(30) Foreign Application Priority Data

Jun. 29, 2018 (EP) ..................... 18181037

(51) Int. Cl.
| | |
|---|---|
| A61K 38/28 | (2006.01) |
| A61K 9/00 | (2006.01) |
| A61K 9/08 | (2006.01) |
| A61K 47/34 | (2017.01) |
| A61K 47/02 | (2006.01) |
| C07D 207/16 | (2006.01) |
| A61K 47/10 | (2017.01) |

(52) U.S. Cl.
CPC ............ *A61K 38/28* (2013.01); *A61K 9/0019* (2013.01); *A61K 9/08* (2013.01); *A61K 47/02* (2013.01); *A61K 47/10* (2013.01); *A61K 47/34* (2013.01); *C07D 207/16* (2013.01)

(58) Field of Classification Search
CPC ........ A61K 38/28; A61K 38/00; A61K 47/34; C07K 14/62
See application file for complete search history.

(56) References Cited

U.S. PATENT DOCUMENTS

| | | |
|---|---|---|
| 5,124,314 A | 6/1992 | Cooper |
| 5,234,906 A | 8/1993 | Young et al. |
| 5,656,722 A | 8/1997 | Dorschug |
| 5,866,538 A | 2/1999 | Norup et al. |
| 6,100,376 A | 8/2000 | Dorschug |
| 10,383,920 B2 | 8/2019 | Geissler et al. |
| 10,548,952 B2 | 2/2020 | Geissler et al. |
| 2006/0099264 A1 | 5/2006 | Chan et al. |
| 2007/0248686 A1 | 10/2007 | Touraud et al. |
| 2013/0065826 A1 | 3/2013 | Soula et al. |

(Continued)

FOREIGN PATENT DOCUMENTS

| | | |
|---|---|---|
| CA | 2377211 A1 | 1/2001 |
| EP | 0 499 521 A1 | 8/1992 |

(Continued)

OTHER PUBLICATIONS

Kaushik et al., "Why Is Trehalose an Exceptional Protein Stabilizer", Journal of Biological Chemistry, 2003, 26458-26465 (Year: 2003).*

(Continued)

*Primary Examiner* — Lianko G Garyu
(74) *Attorney, Agent, or Firm* — Oliff PLC

(57) ABSTRACT

A composition includes co-polyamino acid bearing carboxylate charges and at least one hydrophobic radical -Hy that are chosen among the co-polyamino acids according to formula XXXb:

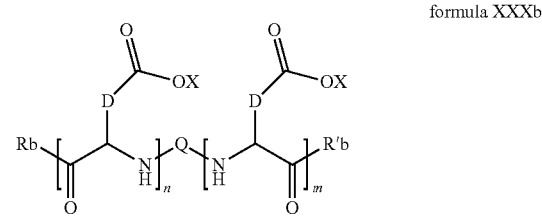

formula XXXb wherein,
D represents, independently, either a group —CH$_2$— (aspartic acid) or a group —CH$_2$—CH$_2$— (glutamic acid), X represents a cationic entity chosen from the group comprising alkali cations, Rb and R'b, identical or different, are either a hydrophobic radical -Hy, or a radical chosen from the group consisting of an H, a C2 to C10 linear acyl group, a C3 to C10 branched acyl group, a benzyl, a terminal "amino acid" unit and a pyroglutamate, at least one of Rb and R'b is a hydrophobic radical -Hy, n+m represents the degree of polymerization DP of the co-polyamino acid, namely the mean number of monomeric units per co-polyamino acid chain and 5≤n+m≤250.

15 Claims, No Drawings

(56) References Cited

U.S. PATENT DOCUMENTS

| | | |
|---|---|---|
| 2013/0178415 A1 | 7/2013 | Soula |
| 2014/0187499 A1 | 7/2014 | Soula et al. |
| 2014/0249079 A1 | 9/2014 | Soula et al. |
| 2014/0348767 A1 | 11/2014 | Hanabusa et al. |
| 2015/0320876 A1 | 11/2015 | Chen et al. |
| 2016/0030672 A1 | 2/2016 | Manderscheid et al. |
| 2017/0216405 A1 | 8/2017 | Sjogren et al. |
| 2017/0348423 A1 | 12/2017 | Geissler |
| 2018/0193421 A1 | 7/2018 | Soula |
| 2019/0216931 A1 | 7/2019 | Chan |
| 2019/0274954 A1 | 9/2019 | Chan et al. |
| 2019/0275109 A1 | 9/2019 | Chan et al. |
| 2019/0275156 A1 | 9/2019 | Chan et al. |
| 2019/0328842 A1 | 10/2019 | Chan et al. |
| 2019/0388515 A1 | 12/2019 | Geissler et al. |
| 2021/0205417 A1 | 7/2021 | Geissler |

FOREIGN PATENT DOCUMENTS

| | | |
|---|---|---|
| EP | 1063254 A1 | 12/2000 |
| FR | 2 801 226 A1 | 5/2001 |
| FR | 2 840 614 A1 | 12/2003 |
| FR | 2 843 117 A1 | 2/2004 |
| FR | 2 873 704 A1 | 2/2006 |
| FR | 2 885 521 A1 | 11/2006 |
| FR | 2 910 318 A1 | 6/2008 |
| FR | 2 985 428 A1 | 7/2013 |
| FR | 2 985 429 A1 | 7/2013 |
| FR | 3 001 896 A1 | 8/2014 |
| FR | 3 052 071 A1 | 12/2017 |
| WO | 2003/005339 A1 | 1/2003 |
| WO | 2004/096854 A2 | 11/2004 |
| WO | 2009/077844 A2 | 6/2009 |
| WO | 2013/021143 A1 | 2/2013 |
| WO | 2013/104861 A1 | 7/2013 |
| WO | 2014/124993 A1 | 8/2014 |
| WO | 2014/124994 A1 | 8/2014 |
| WO | 2015/114171 A1 | 8/2015 |
| WO | 2017/211916 A1 | 12/2017 |
| WO | 2017/211917 A1 | 12/2017 |
| WO | 2018/122278 A1 | 7/2018 |
| WO | 2019/110773 A1 | 6/2019 |

OTHER PUBLICATIONS

Kokotos et al., Novel 2-Oxoamide Inhibitors of Human Group IVA Phospholipase A2, J. Med. Chem. 2002, 45, 2891-2893 (Year: 2002).*

Oct. 25, 2019, Office Action issued in Pakistani Application No. 839/2018.

Nov. 11, 2019 Office Action issued in Pakistani Application No. 840/2018.

U.S. Appl. No. 16/213,809, filed Dec. 7, 2018 in the name of Chan et al.

U.S. Appl. No. 16/212,960, filed Dec. 7, 2018 in the name of Geissler.

U.S. Appl. No. 16/213,963, filed Dec. 7, 2018 in the name of Geissler.

C1266WW00 Recherche AA(STN), Nov. 24, 2016, pp. 1-11.

Finsinger et al., "Protective copolymers for nonviral gene vectors: synthesis, vector characterization and application in gene delivery," Gene Therapy, No. 7, 2000, pp. 1183-1192.

Wang et al., "Synthesis of y-Benzyl-a,L-glutamate Oligomers and their Star Derivatives," American Chemical Society, Polymer Preprints, Division of Polymer Chemistry, 1996, 37: 622-623.

Apr. 19, 2021 Office Action issued in U.S. Appl. No. 16/902,176.

Oct. 7, 2019 International Preliminary Report on Patentability issued in International Patent Application No. PCT/EP2018/083558.

Sep. 22, 2020 Office Action issued in U.S. Appl. No. 16/213,963.

Oct. 7, 2020 International Preliminary Report on Patentability issued in International Patent Application No. PCT/EP2018/083558.

Jun. 9, 2020 English Translation of International Preliminary Report on Patentability issued in International Patent Application No. PCT/EP2018/083558.

Deming; "Polypeptide and Polypeptide Hybrid Copolymer Synthesis via NCA Polymerization;" Adv. Polym. Sci; 2006; pp. 1-18; vol. 202.

Deming; "Facile synthesis of block copolypeptides of defined architecture;" Nature; 1997; pp. 386-389; vol. 390.

Lu et al.; "Hexamethyldisilazane-Mediated Controlled Polymerization of a-Amino Acid N-Carboxyanhydrides;" J. Am. Chem. Soc.; 2007; pp. 14114-14115; vol. 129.

Lu et al.; "N-Trimethylsilyl Amines for Controlled Ring-Opening Polymerization of Amino Acid N-Carboxyanhydrides and Facile End Group Functionalization of Polypeptides;" J. Am Chem. Soc.; 2008; pp. 12562-12563; vol. 130.

Bhatnagar et al.; "Structure-Activity Relationships of Novel Hematoregulatory Peptides;" J. Med. Chem.; 1996; pp. 3814-3819; vol. 39.

Hoppmann et al.; "Intramolecular bridges formed by photoswitchable click amino acids;" Beilstein J. Org. Chem.; 2012; pp. 884-889; vol. 8.

Burnett et al.; "Safety Assessment of Amino Acid Alkyl Amides as Used in Cosmetics;" International Journal of Toxicology; 2017; pp. 17S-56S; vol. 36, No. 1.

Wu et al.; "Interplay of Chemical Microenvironment and Redox Environment on Thiol-Disulfide Exchange Kinetics;" Chem. Eur. J.; 2011; pp. 10064-10070; vol. 17.

Liang et al.; "Distinct optical and kinetic responses from E/Z isomers of caspase probes with aggregation-induced emission characteristics;" J. Mater. Chem. B.; 2014; pp. 4363-4370; vol. 2.

Liu et al.; "Fluorescent Molecular Probes V: A Sensitive Caspase-3 Substrate for Fluorometric Assays;" Bioorganic & Medicinal Chemistry Letters; 1999; pp. 3231-3236; vol. 9.

Leishman et al.; "Lipidomics profile of a NAPE-PLD KO mouse provides evidence of a broader role of this enzyme in lipid metabolism in the brain;" Biochimica et Biophysica Acta; 2016; pp. 491-500; vol. 1861.

Schlitzer et al.; "Non-peptidic, Non-prenylic Bisubstrate Farnesyltransferase Inhibitors, 4. Effect on Farnesyltransferase Inhibitory Activity of Conformational Restrictions in the Central Group;" 2000; pp. 117-124; vol. 5.

Sep. 28, 2018 Search Report issued in French Patent Application No. 1761807.

Feb. 13, 2019 Search Report issued in International Patent Application No. PCT/EP2018/083896.

Feb. 4, 2019 Search Report issued in International Patent Application No. PCT/EP2018/083897.

Nov. 19, 2021 Office Action issued in U.S. Appl. No. 16/902,176.

May 27, 2022 Office Action issued in U.S. Appl. No. 16/902,176.

Sep. 8, 2021 Office Action in Eurasian Patent Office Patent Application No. 202091374.

Carbonization—Wikipedia (Apr. 13, 2022).

Amine—Wikipedia (Apr. 13, 2022).

Ethylenediamine—Wikipedia (Apr. 13, 2022).

Jan. 5, 2022 Office Action in Chinese Patent Application No. 201880084782.8.

Dec. 21, 2021 Office Action in Eurasian Patent Application No. 202091394.

Feb. 21, 2022 Examination Report in Pakistani Patent Application No. 840/2018.

Oct. 14, 2020 Office Action in Vietnamese Patent Application No. 1-2020-03916.

Dec. 16, 2021 Examination Report in Indian Patent Application No. 202017028528.

Sep. 14, 2020 Office Action in Vietnamese Patent Application No. 1-2020-03915.

Apr. 17, 2020 International Search Report in International Patent Application No. PCT/EP2019/084293.

Aug. 4, 2021 Office Action in Saudi Arabian Patent Application No. 520412142.

Jun. 21, 2021 Examination Report in Algerian Patent Appliation No. 200301.

(56) References Cited

OTHER PUBLICATIONS

Aug. 5, 2022 Office Action in Indonesian Patent Application No. P00202004885.
Sep. 20, 2022 Office Action issued in U.S. Appl. No. 16/902,176.
Jul. 26, 2022 Office Action issued in U.S. Appl. No. 16/902,176.
Dec. 1, 2022 Office Action issued in U.S. Appl. No. 17/208,514.

* cited by examiner

INJECTABLE SOLUTION AT PH 7 COMPRISING AT LEAST ONE BASAL INSULIN WHEREIN THE PI IS COMPRISED FROM 5.8 TO 8.5 AND A CO-POLYAMINO ACID BEARING CARBOXYLATE CHARGES AND HYDROPHOBIC RADICALS

The invention relates to insulin injection therapies for treating diabetes.

The invention relates to physically stable compositions in the form of an injectable aqueous solution, wherein the pH is comprised from 6.0 to 8.0, comprising at least one basal insulin which isoelectric point (pI) is comprised from 5.8 to 8.5 and a co-polyamino acid bearing carboxylate charges and hydrophobic radicals.

Insulin therapy, or insulin injection diabetes therapy, has seen remarkable progress in recent years due to notably the development of novel insulins offering superior patient blood glucose correction compared to human insulin and which allow better simulation of the physiological activity of the pancreas.

When type II diabetes is diagnosed in a patient, a gradual treatment is instituted. The patient firstly takes oral antidiabetic drugs (OADs) such as Metformin. When OADs alone are no longer sufficient to regulate the blood glucose level, a treatment modification must be made and, based on patient specificities, various treatment combinations may be put in place. The patient may for example have a treatment based on a basal insulin such as insulin glargine or insulin detemir in addition to OADs, and then subsequently according to the progression of the condition a treatment based on basal insulin and prandial insulin.

Moreover, at the present time, to ensure the transition from OAD treatments, if said treatments are no longer capable of controlling the blood glucose level, to a basal insulin/prandial insulin treatment, the injection of GLP-1 RA analogs is recommended.

GLP-1 RAs or Glucagon-Like Peptide-1 receptor agonists, are insulinotropic peptides or incretins, and belong to the family of the gastro intestinal hormones (or gut hormones) which stimulate insulin secretion when blood sugar is too elevated, for example after a meal.

The gastrointestinal hormones are also known as satiety hormones. They comprise in particular GLP-1 RA (Glucagon like peptide-1 receptor agonist) and GIP (Glucose-dependent insulinotropic peptide), oxyntomodulin (a derivative of proglucagon), peptide YY, amylin, cholecystokinin, pancreatic polypeptide (PP), ghrelin and enterostatin which have peptide or protein structures. They also stimulate insulin secretion, in response to glucose and to fatty acids and are therefore as such potential candidates for treating diabetes.

Among said gastrointestinal hormones, GLP-1 RAs are those which have furnished the best results in drug development to date. They have enabled type II diabetes patients to lose weight while having superior control of their blood sugar.

GLP-1 RA analogs or derivatives have thus been developed notably to enhance the stability thereof.

Moreover, a diabetic patient, to cover his/her daily insulin needs, currently has available, in a simplified manner two types of insulins having complementary actions: prandial insulins (or so-called rapid-acting insulins) and basal insulins (or so-called slow-acting insulins).

Prandial insulins enable rapid processing (metabolization and/or storage) of any glucose intake during meals and snacks. The patients must inject themselves with prandial insulin before each food intake, i.e. about 2 to 3 injections per day. The most commonly used prandial insulins are: recombinant human insulin, NovoLog® (insulin aspart from NOVO NORDISK), Humalog® (insulin lispro from ELI LILLY) and Apidra® (insulin glulisine from SANOFI).

Basal insulins help maintain the patient's glucose homeostasis, outside mealtimes. They act essentially to inhibit endogenous glucose production (hepatic glucose). The daily dose of basal insulin is generally equivalent to 40-50% of the total daily insulin requirements. According to the basal insulin used, this dose is dispensed in 1 or 2 injections, at regular intervals during the day. The most commonly used basal insulins are Levemir® (insulin detemir from NOVO NORDISK) and Lantus® (insulin glargine from SANOFI).

It is worth noting, in order to be exhaustive, that NPH (NPH insulin for Neutral Protamine Hagedorn; Humulin NPH®, Insulatard®) is the oldest form of basal insulin. This formulation is the result of a precipitation of human insulin (anionic at neutral pH) by a cationic protein, protamine. The microcrystals formed are dispersed in an aqueous suspension and are dissolved slowly after subcutaneous injection. This slow dissolution provides a sustained insulin release. However, this release does not provide a constant insulin concentration over time. The release profile is bell-shaped and only lasts from 12 to 16 hours. Therefore, it is injected twice daily. This NPH basal insulin is much less effective than modern basal insulins, Levemir® and Lantus®. NPH is an intermediate-acting basal insulin.

The principle of NPH has evolved with the appearance of rapid-acting insulin analogs to give so-called "Premix" products offering both rapid action and intermediate action. NovoLog Mix® (NOVO NORDISK) and Humalog Mix® (ELI LILLY) are formulations comprising a rapid-acting insulin analog, Novolog® and Humalog®, partially complexed with protamine. These formulations thus contain insulin analog microcrystals said to be intermediate-acting and a portion of insulin remaining soluble which is rapid-acting. These formulations indeed offer the advantage of a rapid-acting insulin but they also have the disadvantage of NPH, i.e. a limited duration of action from 12 to 16 hours and insulin released in a "bell" shape. However, these products enable patients to inject themselves with intermediate-acting basal insulin with a rapid-acting prandial insulin in one injection. Yet many patients are keen to reduce their number of injections.

The basal insulins currently on the market may be categorized according to the technological solution used to arrive at the sustained action and, at the present time, two approaches are used.

The first, that of insulin detemir, is the binding to albumin in vivo. It consists of an analog, soluble at pH 7, which comprises a fatty acid side chain (tetradecanoyl) bound at position B29 which, in vivo, enables this insulin to bind with albumin. The sustained action thereof is essentially due to this affinity for albumin after subcutaneous injection.

However, the pharmacokinetic profile thereof does not enable it to cover one day, meaning that it is generally used in two injections per day.

A further insulin soluble at pH 7, is insulin degludec marketed under the trade name Tresiba®[d]. It also comprises a fatty acid side chain bound to insulin (hexadecandioyl-γ-L-Glu).

The second, that of insulin glargine, is the precipitation at physiological pH. Insulin glargine is a human insulin analog obtained by an elongation of the C-terminal part of the B chain of human insulin with two arginine residues, and by substitution of the A21 asparagine residue, by a glycine residue (U.S. Pat. No. 5,656,722). The addition of two arginine residues was envisaged to adjust the pI (isoelectric point) of insulin glargine at physiological pH, and thus render this human insulin analog insoluble in physiological medium.

Also, the substitution of A21 was envisaged in order to render insulin glargine stable at acidic pH and thus to be able to formulate it in the form of an injectable solution at acidic pH. Following a subcutaneous injection, the change of insulin glargine from an acidic pH (pH 4-4.5) to a physiological pH (neutral pH) induces the precipitation thereof under the skin. The slow redissolution of the insulin glargine micro-particles provides a slow and sustained action.

The hypoglycemic effect of insulin glargine is quasi-constant over a 24-hour period enabling most patients to limit themselves to a single injection per day.

Insulin glargine is now considered as the most commonly used basal insulin.

However, the necessarily acidic pH of basal insulin formulations, which isoelectric point is comprised from 5.8 to 8.5, such as insulin glargine, may be a genuine drawback, as this acidic pH of the insulin glargine formulation sometimes causes pain upon injection in patients and particularly prevents any formulation with other proteins and in particular with prandial insulins as the latter are not stable at acidic pH. The inability to formulate a prandial insulin, at acidic pH, stems from the fact that a prandial insulin undergoes, under these conditions, a secondary deamidation reaction at position A21, which is not suitable for meeting the stability requirements applicable to injectable medicinal products.

To date, in the applications WO 2013/021143 A1, WO 2013/104861 A1, WO 2014/124994 A1 and WO 2014/124993 A1, it has been demonstrated that it was possible to solubilize these basal insulins, such as insulin glargine which isoelectric point is comprised from 5.8 to 8.5, at neutral pH, while maintaining a difference in solubility between the in-vitro medium (the container) and the in-vivo medium (under the skin), independently of the pH.

The application WO 2013/104861 A1, in particularly, describes compositions in the form of an injectable aqueous solution, wherein the pH is comprised from 6.0 and 8.0, comprising at least (a) a basal insulin which isoelectric point pI is comprised from 5.8 to 8.5 and (b) a co-polyamino acid bearing carboxylate charges substituted by hydrophobic radicals.

These prior art compositions do not make it possible to meet the specifications applicable to pharmaceutical formulations in a satisfactory manner.

Therefore, there is a need to find a solution suitable for solubilizing a basal insulin which isoelectric point (pI) is comprised from 5.8 to 8.5 while retaining the basal profile thereof after injection but also suitable for meeting standard physical stability requirements for insulin-based pharmaceutical products.

Surprisingly, the applicant discovered that the co-polyamino acids bearing carboxylate charges and hydrophobic radicals according to the invention make it possible to obtain compositions in the form of solutions which not only meet the requirements described in WO 2013/104861 A1 but which are furthermore capable of meeting all the requirements without having to increase the quantity of excipients used.

These performances never hitherto attained are furthermore maintained when the basal insulin which isoelectric point is comprised from 5.8 to 8.5 is associated in the composition with a prandial insulin and/or a gastrointestinal hormone.

Thus, surprisingly, the affinity of the co-polyamino acids according to the invention for insulin glargine was increased in that it makes it possible to obtain solubilization and stabilization of the insulin glargine solutions at a ratio [Hy]/[basal insulin] lower than that of the prior art; these results are furthermore obtained without impairing, even improving, the tendency of insulin glargine to precipitate as demonstrated in the experimental part.

This improvement of the affinity further makes it possible in the context of chronic treatments to limit the level of exposure to said excipients.

The co-polyamino acids bearing carboxylate charges and hydrophobic radicals Hy according to the invention exhibit an excellent resistance to hydrolysis. This may particularly be verified under accelerated conditions, for example by hydrolysis tests at basic pH (pH 12).

Moreover, forced oxidation tests, for example of the Fenton oxidation type, demonstrate that the co-polyamino acids bearing carboxylate charges and hydrophobic radicals Hy exhibit a good resistance to oxidation.

The invention relates to physically stable compositions in the form of an injectable aqueous solution, wherein the pH is comprised from 6.0 to 8.0, comprising at least:
  a) a basal insulin which isoelectric point (pI) is comprised from 5.8 to 8.5 and
  b) a co-polyamino acid bearing carboxylate charges and at least one hydrophobic radical according to formula X, said co-polyamino acid being chosen among the co-polyamino acids according to formula I.

The invention thus relates to physically stable compositions in the form of an injectable aqueous solution, wherein the pH is comprised from 6.0 to 8.0, comprising at least:
  a) a basal insulin which isoelectric point (pI) is comprised from 5.8 to 8.5,
  b) a prandial insulin, and
  c) a co-polyamino acid bearing carboxylate charges and at least one hydrophobic radical according to formula X, said co-polyamino acid being chosen among the co-polyamino acids according to formula I.

The invention thus relates to physically stable compositions in the form of an injectable aqueous solution, wherein the pH is comprised from 6.0 to 8.0, comprising at least:
  a) a basal insulin which isoelectric point (pI) is comprised from 5.8 to 8.5
  b) a gastrointestinal hormone, and
  c) a co-polyamino acid bearing carboxylate charges and at least one hydrophobic radical according to formula X, said co-polyamino acid being chosen among the co-polyamino acids according to formula I The invention thus relates to physically stable compositions in the form of an injectable aqueous solution, wherein the pH is comprised from 6.0 to 8.0, comprising at least:
  a) a basal insulin which isoelectric point (pI) is comprised from 5.8 to 8.5
  b) a prandial insulin and a gastrointestinal hormone, and
  c) a co-polyamino acid bearing carboxylate charges and at least one hydrophobic radical according to formula X, said co-polyamino acid being chosen among the co-polyamino acids according to formula I The invention thus relates to physically stable compositions in the form of an injectable aqueous solution, wherein the pH is comprised from 6.0 to 8.0, comprising at least:
  a) a basal insulin which isoelectric point (pI) is comprised from 5.8 to 8.5 and
  b) a co-polyamino acid bearing carboxylate charges and at least one hydrophobic radical according to formula X, said co-polyamino acid being chosen among the co-polyamino acids according to formula I:

[Q(PLG)$_k$][Hy]$_j$[Hy]$_{j'}$  Formula I

Wherein:
  j≥1; 0≤j'≤n'1 and j+j'≥1 and k≥2
  said co-polyamino acid according to formula I bearing at least one hydrophobic radical -Hy, carboxylate charges and consisting of at least two chains of glutamic or aspartic units PLG bound together by at least a divalent linear or branched radical or spacer Q[-*]$_k$ consisting of an alkyl chain comprising one or a plurality of heteroatoms chosen in the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions,
    said radical or spacer Q[-*]$_k$ being bound to at least two glutamic or aspartic unit chains PLG by an amide function and,
    said amide functions binding said radical or spacer Q[-*]$_k$ bound to said at least two chains of glutamic or aspartic units result from the reaction between an amine function and an acid function respectively borne either by the precursor Q' of the radical or spacer Q[-*]$_k$ or by a glutamic or aspartic unit,
    said hydrophobic radical -Hy being bound either to a terminal "amino acid" unit and then j≥1, or to a carboxyl function borne by one of the chains of the glutamic or aspartic units PLG and then j'=n'1 and n'1 is the mean number of monomeric units bearing a hydrophobic radical -Hy.

In one embodiment, k is 2, 3, 4, 5 or 6.
In one embodiment, k=2.
In one embodiment, k=3.
In one embodiment, k=4.
In one embodiment, k=5.
In one embodiment, k=6.
In one embodiment, j is 1, 2, 3, 4, 5 or 6.
In one embodiment, j=1.
In one embodiment, j=2.
In one embodiment, j=3.
In one embodiment, j=4.
In one embodiment, j=5.
In one embodiment, j=6.
In one embodiment, g+h≥2 and b is equal to 0 (b=0).
In one embodiment, g or h is greater than or equal to 2 (g≥2) and b is equal to 0.
In one embodiment, g+h≥2, b is equal to 0 (b=0) and e is equal to 1 (e=1).
In one embodiment, g or h is greater than or equal to 2 (g≥2), b is equal to 0 (b=0) and e is equal to 1 (e=1).
In one embodiment, g+h≥2.
In one embodiment, g is greater than or equal to 2 (g≥2).
In one embodiment, h is greater than or equal to 2 (h≥2).
In one embodiment, g+h≥2 and a and l are equal to 0 (a=l=0).
In one embodiment, the hydrophobic radical Hy is chosen in the group of hydrophobic radicals according to formula X, wherein h is greater than or equal to 2 and GpC is according to formula Ixe.
In one embodiment, the hydrophobic radical Hy is chosen in the group of hydrophobic radicals according to formula X, wherein g is greater than or equal to 2 and a, l and h are equal to 0 and GpC is according to formula Ixe.

In one embodiment, if r≥1 and g+l=1 then GpR is a radical according to formula VII' or VII".
In one embodiment, if r≥1 and g+l=1 then GpR is a radical according to formula VII' or VII" and e=0.
In one embodiment, if r≥1 and g+l=1 then GpR is a radical according to formula VII' or VII" and e=1.
In one embodiment, j'=0, g+h≥1, a=l=0 and e=0.
In one embodiment, j'=0, g+h≥1, a=l=0 and e=1.
In one embodiment, j'=0, g+h≥1, a+l≥1 and e=1
In one embodiment, j'=0, g+h≥1, a+l≥1 and e=0
In one embodiment, j'=0, g=h=0, a=l=0 and e=0.
In one embodiment, j'=0, g=h=0, a=l=0 and e=1.
In one embodiment, j'=0, g=h=0, a+l≥1 and e=1
In one embodiment, j'=0, g=h=0, a+l≥1 and e=0

Said co-polyamino acid bearing carboxylate charges and hydrophobic radicals -Hy is soluble in aqueous solution at pH from 6.0 to 8.0, at a temperature of 25° C. and at a concentration below 100 mg/ml.

Said co-polyamino acid bearing carboxylate charges and hydrophobic radicals -Hy is soluble in aqueous solution at pH from 6.0 to 8.0, at a temperature of 25° C. and at a concentration below 60 mg/ml.

The term "alkyl radical" denotes a linear or branched carbon chain, which does not comprise a heteroatom.

Said co-polyamino acid is a statistical co-polyamino acid in the chain of glutamic and/or aspartic units.

In the formulas, the * indicate the binding sites of the different elements represented.

The term "physically stable composition" denotes compositions meeting the visual inspection criteria described in the European, US and international pharmacopeia, namely compositions which are clear and free from visible particles, but also colorless.

The term "injectable aqueous solution" denotes solutions wherein the solvent is water and which meet the EP and US pharmacopeia requirements.

The compositions in the form of an injectable aqueous solution according to the invention are clear solutions. The term "clear solution" denotes compositions meeting the criteria described in the US and European pharmacopeias in respect of injectable solutions. In the US pharmacopeia, solutions are defined in part <1151> referring to injection <1> (referring to <788> as per USP 35 and specified in <788> as per USP 35 and in <787>, <788> and <790> USP 38 (from Aug. 1, 2014), as per USP 38). In the European pharmacopeia, injectable solutions must comply with the criteria provided in sections 2.9.19 and 2.9.20.

The terms "co-polyamino acid consisting of glutamic or aspartic units" denotes non-cyclic linear chains of glutamic acid or aspartic acid units bound together by peptide bonds, said chains having a C-terminal part, corresponding to the carboxylic acid of one extremity, and an N-terminal part, corresponding to the amine of the other extremity of the chain.

The term "soluble" denotes suitable for enabling the preparation of a clear, particle-free solution at a concentration below 100 mg/ml in distilled water at 25° C.

The term "soluble" denotes suitable for enabling the preparation of a clear, particle-free solution at a concentration below 60 mg/ml in distilled water at 25° C.

The radicals -Hy, GpR, GpG, GpA, GpL, GpH and GpC are each independently identical or different from one residue to another.

In one embodiment, the composition is characterized in that the pH is comprised from 6.0 to 8.0.

In one embodiment, the composition is characterized in that the pH is comprised from 6.6 to 7.8.

In one embodiment, the composition is characterized in that the pH is comprised from 7.0 to 7.8.

In one embodiment, the composition is characterized in that the pH is comprised from 6.8 to 7.4.

In one embodiment, the composition according to the invention is characterized in that Hy comprises from 15 to 100 carbon atoms.

In one embodiment, the composition according to the invention is characterized in that Hy comprises from 30 to 70 carbon atoms.

In one embodiment, the composition according to the invention is characterized in that Hy comprises to 40 to 60 carbon atoms.

In one embodiment, the composition according to the invention is characterized in that Hy comprises to 20 to 30 carbon atoms In one embodiment, Hy comprises more than 15 carbon atoms.

In one embodiment, Hy comprises more than 30 carbon atoms.

In one embodiment, the radical or spacer $Q[-*]_k$ is represented by a radical according to formula II:

$$Q[-*]_k = ([Q']_q[-*]_k \quad \text{Formula II}$$

Wherein $1 \leq q \leq 5$

The radicals Q' being identical or different and chosen in the group consisting of radicals of the following formulas III to VI', to form $Q[-*]_k$:

by a radical according to formula III

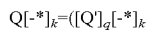

Formula III wherein $1 \leq t \leq 8$ by a radical according to formula IV:

Formula IV wherein:
At least one of $u_1''$ or $u_2''$ is different to 0.
If $u_1'' \neq 0$ then $u_1' \neq 0$ and if $u_2'' \neq 0$ then $u_2' \neq 0$,
$u_1'$ and $u_2'$ are identical or different and,
$2 \leq u \leq 4$,
$0 \leq u_1' \leq 4$,
$0 \leq u_1'' \leq 4$,
$0 \leq u_2' \leq 4$
$0 \leq u_2'' \leq 4$,
by a radical according to formula V:

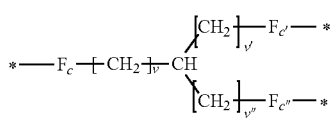

Formula V

Wherein:
v, v' and v" identical or different, are integers $\geq 0$, and $v+v'+v'' \leq 15$, by a radical according to formula VI:

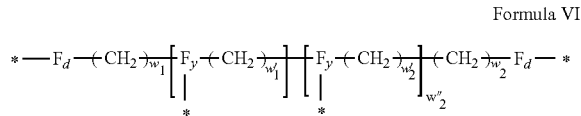

Formula VI

Wherein:
$w_1'$ is different to 0,
$0 < w_2'' \leq 1$,
$w_1 \leq 6$ and $w_1' \leq 6$ and/or $w_2 \leq 6$ and $w_2' \leq 6$
where Fd, and Fd' identical or different representing functions —NH— or —CO— and Fy representing a trivalent nitrogen atom —N=,
where in each of the radicals represented above Fx=Fa, Fb, Fc, Fd, Fa', Fb', Fc', Fc" and Fd' identical or different representing functions —NH— or —CO— and Fy representing a trivalent nitrogen atom —N=,
two radicals Q' being bound together by a covalent bond between a carbonyl function, Fx=—CO—, and an amine function Fx=—NH— or Fy=—N=, thus forming an amide bond and where a function Fx=Fa, Fb, Fc, Fd, Fa', Fb', Fc', Fc" and Fd' is not used in a bond between two Q', this function is then free and salified.

In one embodiment, said radical Q' is chosen among the radicals according to formula VI, wherein $w_2=0$ according to formula VI' as defined hereinafter:

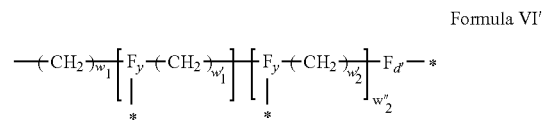

Formula VI' wherein:
$w_1'$ is different to 0,
$0 \leq w_2'' \leq 1$,
$w_1 \leq 6$ and $w_1' \leq 6$ and/or $w_2' \leq 6$
where Fd, and Fd' identical or different representing functions —NH— or —CO— and Fy representing a trivalent nitrogen atom —N=,
two radicals Q' being bound together by a covalent bond between a carbonyl function, Fx=—CO—, and an amine function Fx=—NH— or Fy=—N=, thus forming an amide bond,
where in each of the radicals represented above, Fx=Fa, Fb, Fc, Fd, Fa', Fb', Fc' and Fd' identical or different representing functions —NH— or —CO— and Fy representing a trivalent nitrogen atom —N=,
two radicals Q' being bound together by a covalent bond between a carbonyl function, Fx=—CO—, and an amine function Fx=—NH— or Fy=—N=, thus forming an amide bond.

In one embodiment, if Fa and Fa' are —NH—, then $t \geq 2$.
In one embodiment, if Fa and Fa' are —CO—, then $t \geq 1$.
In one embodiment, if Fa and Fa' are —CO— and —NH—, then $t \geq 1$.
In one embodiment, if Fb and Fb' are —NH—, then u and $u_1' \geq 2$ and/or $u_2' \geq 2$.
In one embodiment, if Fc, Fc' and Fc' are —NH— then at least two of v, v' and v" are different to 0.
In one embodiment, if Fc, Fc' and Fc' are 2-NH— and 1-CO— then at least one of the indices of the —(CH$_2$)— bearing a nitrogen is different to 0.

In one embodiment, if Fc, Fc' and Fc' are 1-NH— and 2-CO— then no conditions.

In one embodiment, if Fc, Fc' and Fc' are —CO— then at least one of v, v' and v" is different to 0.

In one embodiment, if Fd and Fd' are —NH—, w1 and w1'≥2 and/or w2 and w'2≥2.

In one embodiment, if Fd and Fd' are —CO—, w1 and w1'≥1 and/or w2 and w2'≥1.

In one embodiment, if Fd and Fd' are —CO— and —NH—, w1 and w1'≥1 and/or w2 and w2'≥1.

The at least two chains of glutamic or aspartic units PLG being bound to Q[-*]k by a function Fx or Fy by a covalent bond to form an amide bond with a function —NH— or —CO— of the PLG.

In one embodiment, 1≤q≤5.

In one embodiment, v+v'+v"≤15.

In one embodiment, at least one of the Q' is a radical according to formula III,

III wherein the precursor is a diamine.

In one embodiment, the precursor of the radical according to formula III is a diamine chosen in the group consisting of ethylene diamine, butylenediamine, hexylenediamine, 1,3-diaminopropane and 1,5-diaminopentane, propylene diamine, pentylene diamine.

In one embodiment, t=2 and the precursor of the radical according to formula III is ethylenediamine.

In one embodiment, t=4 and the precursor of the radical according to formula III is butylenediamine.

In one embodiment, t=6 and the precursor of the radical according to formula III is hexylenediamine.

In one embodiment, t=3 and the precursor of the radical according to formula III is 1,3-diaminopropane.

In one embodiment, t=5 and the precursor of the radical according to formula III is 1,5-diaminopentane.

In one embodiment, the precursor of the radical according to formula III is an amino acid.

In one embodiment, the precursor of the radical according to formula III is an amino acid chosen in the group consisting of aminobutanoic acid, aminohexanoic acid and beta-alanine.

In one embodiment, t=2 and the precursor of the radical according to formula III is beta-alanine.

In one embodiment, t=6 and the precursor of the radical according to formula III is aminohexanoic acid.

In one embodiment, t=4 and the precursor of the radical according to formula III is aminobutanoic acid In one embodiment, the precursor of the radical according to formula III is a diacid.

In one embodiment, the precursor of the radical according to formula III is a diacid chosen in the group consisting of succinic acid, glutaric acid and adipic acid.

In one embodiment, t=2 and the precursor of the radical according to formula III is succinic acid.

In one embodiment, t=3 and the precursor of the radical according to formula III is glutaric acid.

In one embodiment, t=4 and the precursor of the radical according to formula III is adipic acid.

In one embodiment, at least one of the Q' is a radical according to formula IV,

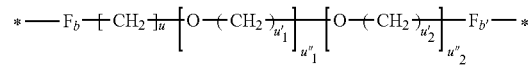

Formula IV wherein the precursor is a diamine.

In one embodiment, the precursor of the radical according to formula IV is a diamine chosen in the group consisting of diethyleneglycoldiamine, triethyleneglycol diamine, 1-amino-4,9-dioxa-12-dodecanamine and 1-amino-4,7,10-trioxa-13-tridecanamine.

In one embodiment, $u=u'_1=2$, $u''_1=1$, $u''_2=0$ and the precursor of the radical according to formula IV is diethyleneglycol diamine.

In one embodiment, $u=u'_1=u'_2=2$, $u''_1=u''_2=1$ and the precursor of the radical according to formula IV is triethyleneglycol diamine.

In one embodiment, $u=u'_2=3$, $u'_1=4$, $u''_1=u''_2=1$ and the precursor of the radical according to formula IV is 4,9-dioxa-1,12-dodecanediamine.

In one embodiment, $u=u'_2=3$, $u'_1=u''_1=2$, $u''_2=1$ and the precursor of the radical according to formula IV is 4,7,10-trioxa-1,13-tridecanediamine.

In one embodiment, at least one of the Q' is a radical according to formula V,

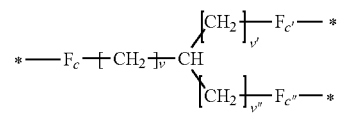

Formula V wherein the precursor is chosen in the group consisting of amino acids.

In one embodiment, the precursor of the radical according to formula V is an amino acid chosen in the group consisting of lysine, ornithine, 1,3-diaminopropionic acid.

In one embodiment, v=4, v'=v"=0 and the precursor of the radical according to formula V is lysine.

In one embodiment, v=3, v'=v"=0 and the precursor of the radical according to formula V is ornithine.

In one embodiment, v=2, v'=v"=0 and the precursor of the radical according to formula V is 2,3-diaminopropionic acid.

In one embodiment, at least one of the Q' is a radical according to formula V,

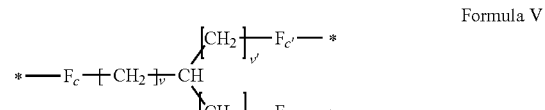

Formula V wherein the precursor is chosen in the group consisting of triacids.

In one embodiment, the precursor of the radical according to formula V is a triacid chosen in the group consisting of tricarballylic acid.

In one embodiment, v=0, v'=v"=1 and the precursor of the radical according to formula V is tricarballylic acid.

In one embodiment, at least one of the Q' is a radical according to formula V,

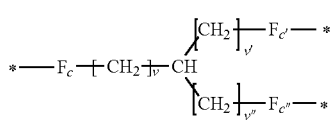

Formula V wherein the precursor is chosen in the group consisting of triamines.

In one embodiment, the precursor of the radical according to formula V is a triamine chosen in the group consisting of (2-(aminomethyl)propane-1,3-diamine).

In one embodiment, $v=v'=v''=1$ and the precursor of the radical according to formula V is (2-(aminomethyl)propane-1,3-diamine).

In one embodiment, at least one of the Q' is a radical according to formula VI,

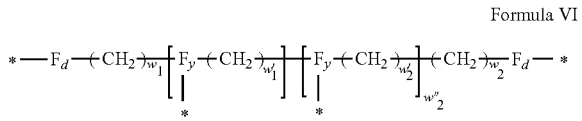

Formula VI wherein the precursor is a triamine.

In one embodiment, $w''_2=0$ and the precursor of the radical according to formula VI is a triamine chosen in the group consisting of spermidine, norspermidine, and diethylenetriamine and bis(hexamethylene)triamine.

In one embodiment, $w''_2=0$ and the precursor of the radical according to formula VI is spermidine.

In one embodiment, $w''_2=0$ and the precursor of the radical according to formula VI is norspermidine.

In one embodiment, $w''_2=0$ and the precursor of the radical according to formula VI is diethylenetriamine.

one embodiment, $w''_2=0$ and the precursor of the radical according to formula VI is bis(hexamethylene)triamine.

In one embodiment, at least one of the Q' is a radical according to formula VI,

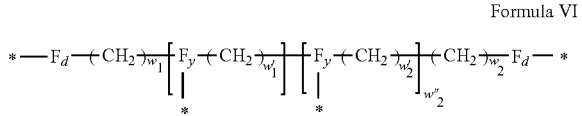

Formula VI wherein the precursor is a tetramine.

In one embodiment, $w''_2=1$ and the precursor of the radical according to formula VI is a tetramine.

In one embodiment, $w''_2=1$ and the precursor of the radical according to formula VI is a tetramine chosen in the group consisting of spermine and triethylenetetramine.

In one embodiment, $w''_2=1$ and the precursor of the radical according to formula VI is spermine.

In one embodiment, $w''_2=1$ and the precursor of the radical according to formula VI is triethylenetetramine.

In one embodiment, the precursor of the radical or spacer Q[-*]$_k$ has 4 reactive functions, chosen among the amine and carboxylic acid functions. Such a precursor may be 1,2,3,4-butanetetraoic acid.

In one embodiment, at least one of the Q' is a radical according to formula VI',

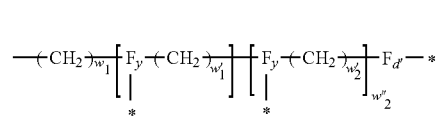

Formula VI' wherein the precursor is a triamine.

In one embodiment, $w''2=0$ and the precursor of the radical according to formula VI' is a triamine chosen in the group consisting of spermidine, norspermidine, and diethylenetriamine and bis(hexamethylene)triamine.

In one embodiment, $w''2=0$ and the precursor of the radical according to formula VI' is spermidine.

In one embodiment, $w''2=0$ and the precursor of the radical according to formula VI' is norspermidine.

In one embodiment, $w''2=0$ and the precursor of the radical according to formula VI' is diethylenetriamine.

one embodiment, $w''2=0$ and the precursor of the radical according to formula VI is bis(hexamethylene)triamine.

In one embodiment, at least one of the Q' is a radical according to formula VI',

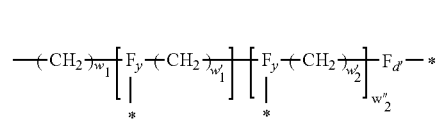

Formula VI' wherein the precursor is a tetramine.

In one embodiment, $w''2=1$ and the precursor of the radical according to formula VI' is a tetramine.

In one embodiment, $w''2=1$ and the precursor of the radical according to formula VI' is a tetramine chosen in the group consisting of spermine and triethylenetetramine.

In one embodiment, $w''2=1$ and the precursor of the radical according to formula VI' is spermine.

In one embodiment, $w''2=1$ and the precursor of the radical according to formula VI' is triethylenetetramine.

In one embodiment, the precursor of the radical or spacer Q[-*]$_k$ has 4 reactive functions, chosen among the amine and carboxylic acid functions.

In one embodiment, the precursor of the radical or spacer Q[-*]$_k$ has 4 reactive functions and the precursor of the radical or spacer Q[-*]$_k$ is 1,2,3,4-butanetetraoic acid.

In one embodiment, all the Fx are bound to the PLG or to other Fx or Fy.

In one embodiment, one or plurality of Fx are free, i.e. are not bound to the PLG, or to another Fx, or to an Fy.

In one embodiment, one Fx is free, i.e. is not bound to the PLG, or to another Fx, or to an Fy.

In one embodiment, the —CO— type Fx(s) is free, it is in carboxylic acid salt form.

In one embodiment, the free —CO— type Fx is borne by a radical Q' according to Formula V.

In one embodiment, the —NH— type Fx(s) is free, it is in amine or ammonium form.

In one embodiment, the PLGs are bound to Fx where Fx=—NH— or to Fy by at least one carbonyl function of the PLG.

In one embodiment, the PLGs are bound to Fx where Fx=—NH— or to Fy by at least one carbonyl function which is not in the C-terminal position of the PLG.

In one embodiment, the PLGs are bound to Fx where Fx=—NH— or to Fy by the carbonyl function in the C-terminal function of the PLG.

In one embodiment, the PLGs are bound to Fx where Fx=—NH— by the carbonyl function in the C-terminal function of the PLG.

In one embodiment, the PLGs are bound to Fx where Fx=Fy by the carbonyl function in the C-terminal function of the PLG.

In one embodiment, the PLGs are bound to Fx, where Fx=—CO— by the nitrogen atom in the N-terminal function of the PLG.

In one embodiment, the composition according to the invention is characterized in that the co-polyamino acid bearing carboxylate charges and at least one hydrophobic radical -Hy is chosen among the co-polyamino acids according to formula XXXa hereinafter:

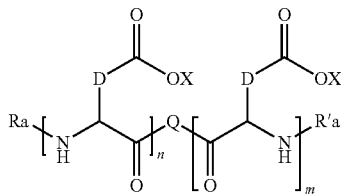

Formula XXXa wherein,
- D represents, independently, either a group —CH$_2$— (aspartic acid) or a group —CH$_2$—CH$_2$— (glutamic acid),
- X represents a cationic entity chosen in the group comprising alkali cations,
- Ra and R'a, identical or different, are either a hydrophobic radical -Hy, or a radical chosen in the group consisting of an H, a C2 to C10 linear acyl group, a C3 to C10 branched acyl group, a benzyl, a terminal "amino acid" unit and a pyroglutamate,
- at least one of Ra and R'a being a hydrophobic radical -Hy,
- Q is as defined above
- -Hy is as defined hereinafter.
- n+m represents the degree of polymerization DP of the co-polyamino acid, namely the mean number of monomeric units per co-polyamino acid chain and 5≤n+m≤250.

In one embodiment, the composition according to the invention is characterized in that the co-polyamino acid bearing carboxylate charges and at least one hydrophobic radical -Hy is chosen among the co-polyamino acids according to formula XXXa wherein $R_a$ and $R'_a$, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa wherein $R_a$ and $R'_a$, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXa wherein $R_a$ is a hydrophobic radical -Hy and $R'_a$ is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa wherein $R'_a$ is a hydrophobic radical -Hy, and $R_a$ is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' hereinafter:

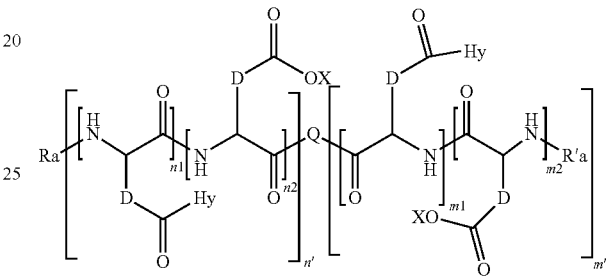

Formula XXXa'

Wherein:
- D, X, Ra and R'a are as defined above,
- Q and Hy are as defined above,
- $n_1+m_1$ represents the number of glutamic units or aspartic units of the PLG chains of the co-polyamino acid bearing a radical -Hy,
- $n_2+m_2$ represents the number of glutamic units or aspartic units of the PLG chains of the co-polyamino acid not bearing a radical -Hy,
- $n_1+n_2=n'$ and $m_1+m_2=m'$
- n'+m' represents the degree of polymerization DP of the co-polyamino acid, namely the mean number of monomeric units per co-polyamino acid chain and 5≤n'+m'≤250.

In one embodiment, the composition according to the invention is characterized in that the co-polyamino acid bearing carboxylate charges and at least one hydrophobic radical -Hy is chosen among the co-polyamino acids according to formula XXXa' wherein Ra and R'a, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' wherein Ra and R'a, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXa' wherein Ra is a hydrophobic radical -Hy and R'a is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' wherein R'a is a hydrophobic radical -Hy, and Ra is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb hereinafter:

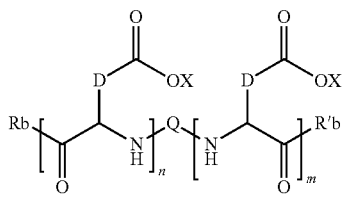

Formula XXXb wherein,

D and X are as defined above,

Rb and R'b, identical or different, are either a hydrophobic radical -Hy, or a radical chosen in the group consisting of an —OH, an amine group, a terminal "amino acid" unit and a pyroglutamate, at least one of Rb and R'b is a hydrophobic radical -Hy, Q and Hy are as defined above.

n+m is as defined above.

In one embodiment, the composition according to the invention is characterized in that the co-polyamino acid bearing carboxylate charges and at least one hydrophobic radical -Hy is chosen among the co-polyamino acids according to formula XXXb wherein Rb and R'b, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb wherein Rb and R'b, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXb wherein Rb is a hydrophobic radical -Hy and R'b is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb wherein R'b is a hydrophobic radical -Hy, and Rb is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' hereinafter:

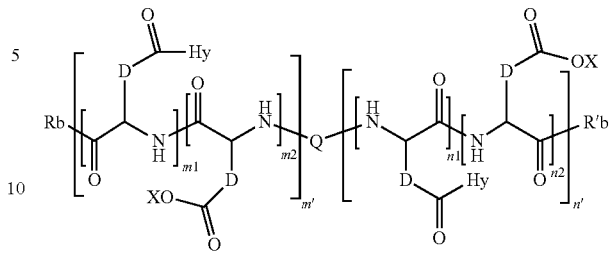

Formula XXXb' wherein:

D and X are as defined above,

Q and Hy are as defined above.

Rb and Rb', identical or different, are either a hydrophobic radical -Hy, or a radical chosen in the group consisting of an —OH, an amine group, a terminal "amino acid" unit and a pyroglutamate, at least one of Rb and R'b is a hydrophobic radical -Hy, n1+m1 represents the number of glutamic units or aspartic units of the PLG chains of the co-polyamino acid bearing a radical -Hy, n2+m2 represents the number of glutamic units or aspartic units of the PLG chains of the co-polyamino acid not bearing a radical -Hy, n1+n2=n' and m1+m2=m', n'+m' represents the degree of polymerization DP of the co-polyamino acid, namely the mean number of monomeric units per co-polyamino acid chain and $5 \leq n'+m' \leq 250$.

In one embodiment, the composition according to the invention is characterized in that the co-polyamino acid bearing carboxylate charges and at least one hydrophobic radical -Hy is chosen among the co-polyamino acids according to formula XXXb' wherein Rb and R'b, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' wherein Rb and R'b, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXb' wherein Rb is a hydrophobic radical -Hy and R'b is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' wherein R'b is a hydrophobic radical -Hy, and Rb is not a hydrophobic radical -Hy.

In one embodiment, the composition is characterized in that the co-polyamino acid bearing carboxylate charges and hydrophobic radicals is chosen among the co-polyamino acids according to formulas XXXa, XXXb, XXXa' or XXXb' wherein the group D is a group —CH$_2$—CH$_2$— (glutamic unit).

In one embodiment, the composition is characterized in that the co-polyamino acid bearing carboxylate charges and hydrophobic radicals is chosen among the co-polyamino acids according to formulas XXXa, XXXa', XXXb' wherein the group D is a group —CH$_2$— (aspartic unit).

When the co-polyamino acid comprises one or a plurality of aspartic unit(s), they can undergo structural rearrangements.

In one embodiment, the composition according to the invention is characterized in that when the co-polyamino acids comprises aspartate units, then the co-polyamino acids may further comprise monomeric units according to formulas XXXX and/or XXXX':

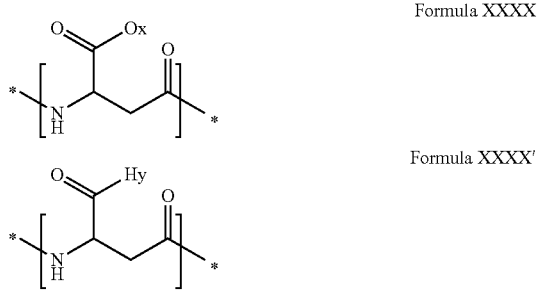

Formula XXXX

Formula XXXX'

The term "statistical grafting co-polyamino acid" denotes a co-polyamino acid bearing carboxylate charges and at least one hydrophobic radical, represented by a co-polyamino acid according to formula XXXa' and XXXb'.

The term "defined grafting co-polyamino acid" denotes a co-polyamino acid bearing carboxylate charges and at least one hydrophobic radical, represented by a co-polyamino acid according to formula XXXa and XXXb.

In one embodiment, the concentration of co-polyamino acid bearing carboxylate charges and hydrophobic radicals is not more than 60 mg/mL.

In one embodiment, the concentration of co-polyamino acid bearing carboxylate charges and hydrophobic radicals is not more than 40 mg/mL.

In one embodiment, the concentration of co-polyamino acid bearing carboxylate charges and hydrophobic radicals is not more than 20 mg/mL.

In one embodiment, the concentration of co-polyamino acid bearing carboxylate charges and hydrophobic radicals is not more than 10 mg/mL.

In one embodiment, the concentration of co-polyamino acid bearing carboxylate charges and hydrophobic radicals is not more than 5 mg/ml.

In one embodiment, the concentration of co-polyamino acid bearing carboxylate charges and hydrophobic radicals is not more than 2.5 mg/ml.

In one embodiment, the composition according to the invention is characterized in that n+m is comprised from 10 to 250.

In one embodiment, the composition according to the invention is characterized in that n+m is comprised from 10 to 200.

In one embodiment, the composition according to the invention is characterized in that n+m is comprised from 15 to 150.

In one embodiment, the composition according to the invention is characterized in that n+m is comprised from 15 to 100.

In one embodiment, the composition according to the invention is characterized in that n+m is comprised from 15 to 80.

In one embodiment, the composition according to the invention is characterized in that n+m is comprised from 15 to 65.

In one embodiment, the composition according to the invention is characterized in that n+m is comprised from 20 to 60.

In one embodiment, the composition according to the invention is characterized in that n+m is comprised from 20 to 50.

In one embodiment, the composition according to the invention is characterized in that n+m is comprised from 20 to 40.

In one embodiment, the invention relates to a composition in the form of an injectable aqueous solution, wherein the pH is comprised from 6.0 to 8.0, comprising at least:
- a basal insulin which isoelectric point pI is comprised from 5.8 to 8.5;
- a co-polyamino acid according to formula I defined above bearing carboxylate charges and hydrophobic radicals -Hy and said at least one hydrophobic radical Hy is chosen among the radical according to formula X:

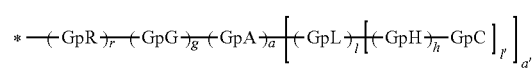

Formula X wherein

GpR is chosen among the radicals according to formulas VII, VII' or VII":

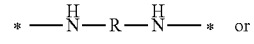

Formula VII

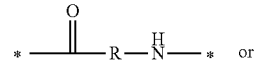

Formula VII'

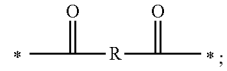

Formula VII";

GpG and GpH identical or different are chosen among the radicals according to formulas XI or XI':

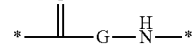

Formula XI

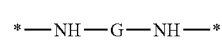

Formula XI'

GpA is chosen among the radicals according to formula VIII

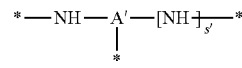

Formula VIII wherein A' is chosen among the radicals according to VIII', VIII" or VIII'"

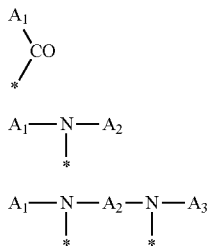

Formula VIII'

Formula VIII"

Formula VIII'"

-GpL is chosen among the radicals according to formula XII

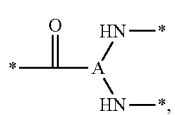

Formula XII

GpC is a radical according to formula IX:

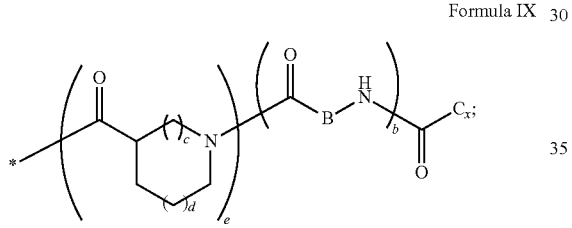

Formula IX the * indicate the binding sites of the different groups bound by amide functions;
a is an integer equal to 0 or to 1 and a'=1 if a=0 and a'=1, 2 or 3 if a=1;
a' is an integer equal to 1, to 2 or to 3
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
r is an integer equal to 0, to 1 or to 2, and
s' is an integer equal to 0 or 1;
A, $A_1$, $A_2$ and $A_3$ identical or different are linear or branched alkyl radicals comprising from 1 to 8 carbon atoms and optionally substituted by a radical from a saturated, unsaturated or aromatic ring;
B is a radical chosen in the group consisting of a non-substituted ether or polyether radical comprising from 4 to 14 carbon atoms and from 1 to 5 oxygen atoms or a linear or branched alkyl radical, optionally comprising an aromatic nucleus, comprising from 1 to 9 carbon atoms;

$C_x$ is a linear or branched monovalent alkyl radical, optionally comprising a cyclic part, wherein x indicates the number of carbon atoms and $6<x<25$:
When the hydrophobic radical -Hy bears 1-GpC, then $9 \leq x \leq 25$,
When the hydrophobic radical -Hy bears 2-GpC, then $9 \leq x \leq 15$,
When the hydrophobic radical -Hy bears 3-GpC, then $7 \leq x \leq 13$,
When the hydrophobic radical -Hy bears 4-GpC, then $7 \leq x \leq 11$,
When the hydrophobic radical -Hy bears at least 5-GpC, then $6 \leq x \leq 11$,
G is a linear or branched divalent alkyl radical of 1 to 8 carbon atoms, said alkyl radical bearing one or a plurality of free carboxylic acid function(s),
R is a radical chosen in the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms:
The hydrophobic radical(s) -Hy according to formula X being bound to the PLG:
via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, and/or
via a covalent bond between a nitrogen atom of the hydrophobic radical -Hy and a carbonyl borne by the PLG thus forming an amide function obtained from the reaction of an amine function of the precursor -Hy' of the hydrophobic radical -Hy and an acid function borne by the PLG,
the ratio M between the number of hydrophobic radicals and the number of glutamic or aspartic units being between $0<M \leq 0.5$;
when a plurality of hydrophobic radicals are borne by a co-polyamino acid then they are identical or different,
the free carboxylic acid functions being in the form of alkali cation salt chosen in the group consisting of $Na^+$ and $K^+$.

In one embodiment, when a'=1, x is comprised from 11 to 25 ($11 \leq x \leq 25$). In particular, when x is comprised from 15 to 16 (x=15 or 16) then r=1 and R is an ether or polyether radical and when x is greater than 17 ($x \geq 17$) then r=1 and R is an ether or polyether radical.

In one embodiment, when a'=2, x is comprised from 9 to 15 ($9 \leq x \leq 15$).

In one embodiment, when r=2 then the group GpR bound to the PLG is chosen among the GpR according to formula VII.

In one embodiment, when r=2 then the group GpR bound to the PLG is chosen among the GpR according to formula VII and the second GpR is chosen among the GpR according to formula VII".

In one embodiment, when r=2 then the group GpR bound to the PLG is chosen among the GpR according to formula VII".

In one embodiment, when r=2 then the group GpR bound to the PLG is chosen among the GpR according to formula VII" and the second GpR is chosen among the GpR according to formula VII.

In one embodiment, said at least one hydrophobic radical -Hy is chosen among the radicals according to formula X wherein r=1 according to formula Xc, as defined hereinafter:

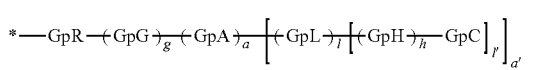

Formula Xc wherein GpR, GpG, GpA, GpL, GpH, GpC, a, a', g, h, l and l' are as defined above.

In one embodiment, said at least one hydrophobic radical -Hy is chosen among the radicals according to formula X wherein r=1 according to formula Xc, as defined hereinafter:

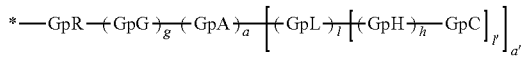

Formula Xc wherein GpR is a radical according to formula VII.

Formula VII wherein GpG, GpA, GpL, GpH, GpC, R, a, a', g, h, l and l' are as defined above.

In one embodiment, said at least one hydrophobic radical -Hy is chosen among the radicals according to formula Xc, as defined hereinafter:

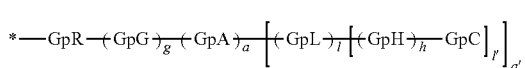

Formula Xc wherein GpR is a radical according to formula VII'.

Formula VII' wherein GpG, GpA, GpL, GpH, GpC, R, a, a', g, h, l and l' are as defined above.

In one embodiment, said at least one hydrophobic radical -Hy is chosen among the radicals according to formula Xc, as defined hereinafter:

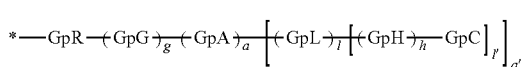

Formula Xc wherein GpR is a radical according to formula VII".

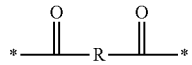

Formula VII"

wherein GpG, GpA, GpL, GpH, GpC, R, a, a', g, h, l and l' are as defined above.

In one embodiment, said at least one hydrophobic radical -Hy is chosen among the radicals according to formula X wherein r=2 according to formula Xc', as defined hereinafter:

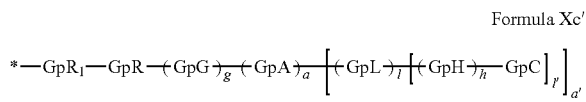

Formula Xc' wherein $GpR_1$ is a radical according to formula VII.

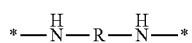

Formula VII wherein GpR, GpG, GpA, GpL, GpH, GpC, R, a, a', g, h, l and l' are as defined above.

In one embodiment, said at least one hydrophobic radical -Hy is chosen among the radicals according to formula X wherein r=2 according to formula Xc', as defined hereinafter:

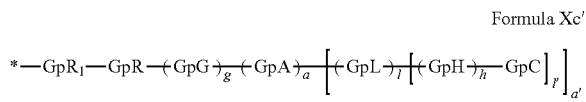

Formula Xc' wherein $GpR_1$ is a radical according to formula VII".

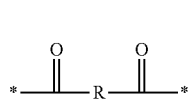

Formula VII"

wherein GpR, GpG, GpA, GpL, GpH, GpC, R, a, a', g, h, l and l' are as defined above.

In one embodiment, said at least one hydrophobic radical -Hy is chosen among the radicals according to formula X wherein r=0 according to formula Xq as defined hereinafter:

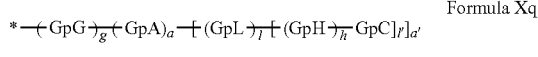

Formula Xq wherein GpG, GpA, GpL, GpH, GpC, g, a, a', l, h and l' are as defined above.

In one embodiment, said at least one hydrophobic radical -Hy is chosen among the radicals according to formula X wherein G=0 according to formula Xr as defined hereinafter:

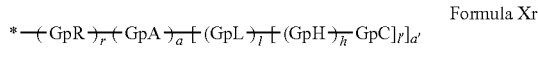

Formula Xr wherein GpR, GpA, GpL, GpH, GpC, r, a, a', l, h and l' are as defined above.

In one embodiment, the composition according to the invention is characterized in that said hydrophobic radicals are chosen among the hydrophobic radicals according to formula X wherein h=0 and g=0, represented by the formula Xj hereinafter:

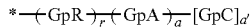  Formula Xj wherein GpR, GpA, GpC, r, a' and a are as defined above.

In one embodiment, the composition according to the invention is characterized in that said hydrophobic radicals are chosen among the hydrophobic radicals according to formula X wherein h=0 and g=0 and a'=1, represented by the formula Xk hereinafter:

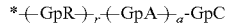  Formula Xk wherein GpR, GpA, GpC, r and a are as defined above.

In one embodiment, the composition according to the invention is characterized in that said hydrophobic radicals are chosen among the hydrophobic radicals according to formula X wherein h=0 and g=0 and a=1 and a'=2, represented by the formula Xl hereinafter:

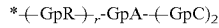  Formula Xl wherein GpR, GpA, GpC and r are as defined above.

In one embodiment, the composition according to the invention is characterized in that said hydrophobic radicals are chosen among the hydrophobic radicals according to formula X wherein a=1 and a'=1 and g=l=0, represented by the formula Xn hereinafter:

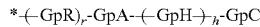  Formula Xn wherein GpR, GpA, GpH, GpC, r and h are as defined above.

In one embodiment, the composition according to the invention is characterized in that said hydrophobic radicals are chosen among the hydrophobic radicals according to formula X wherein a=1 and a'=2 and g=l=0, represented by the formula Xp hereinafter:

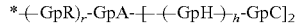  Formula Xp wherein GpR, GpA, GpH, GpC, r and h are as defined above.

In one embodiment, the composition according to the invention is characterized in that said hydrophobic radicals are chosen among the hydrophobic radicals according to formula X wherein a=1, g, h and l=0 and a'=3, represented by the formula Xm hereinafter:

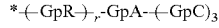  Formula Xm wherein GpA is a radical chosen among the radicals according to formula VIIId and GpR, GpC, r are as defined above.

In one embodiment, the composition according to the invention is characterized in that said hydrophobic radicals are chosen among the hydrophobic radicals according to formula X wherein a, g, h and l=0, represented by the formula Xm' hereinafter:

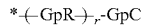  Formula Xm' wherein GpR, GpC, r are as defined above.

In one embodiment, said at least one hydrophobic radical -Hy is chosen among the radicals according to formula X wherein r, g, a, l, h are equal to 0, according to formula Xo as defined hereinafter:

  Formula Xo wherein GpC is as defined above.

In one embodiment, said at least one hydrophobic radical -Hy is chosen among the radicals according to formula X wherein r, g, a, l, h are equal to 0, according to formula Xo as defined hereinafter:

  Formula Xo wherein GpC is a radical according to formula IX wherein e=0, b=0 and GpC is a radical according to formula IXc

  IXc

In one embodiment, said at least one hydrophobic radical -Hy is chosen among the radicals according to formula X wherein a=0 according to formula Xs as defined hereinafter:

  Formula Xs wherein GpR, GpG, GpL, GpH, GpC, r, g, l, h and l' are as defined above.

In one embodiment, said at least one hydrophobic radical -Hy is chosen among the radicals according to formula X wherein a=1 and a'=1 according to formula Xa as defined hereinafter:

  Formula Xa wherein GpA, GpR, GpG, GpL, GpH, GpC, r, g, h, l and l' are as defined above.

In one embodiment, said at least one hydrophobic radical -Hy is chosen among the radicals according to formula X wherein a=1 and a'=1 according to formula Xa as defined hereinafter:

  Formula Xa wherein GpA is a radical according to formula VIII and A' is chosen among the radicals according to formula VIII' where s'=0 and GpA is a radical according to formula VIIIb

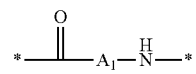  Formula VIIIb wherein GpR, GpG, GpL, GpH, GpC, r, g, h, l and l' are as defined above.

In one embodiment, said at least one hydrophobic radical -Hy is chosen among the radicals according to formula X wherein a=1 and a'=2 according to formula Xb as defined hereinafter:

Formula Xb

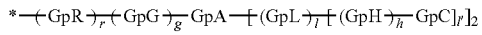

wherein GpA, GpR, GpG, GpL, GpH, GpC, r, g, h, l and l' are as defined above.

In one embodiment, said at least one hydrophobic radical -Hy is chosen among the radicals according to formula X wherein a=1 and a'=2 according to formula Xb as defined hereinafter:

Formula Xb

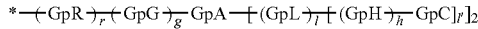

wherein GpA is a radical according to formula VIII and A' is chosen among the radicals according to formula VIII' where s'=1 and GpA is a radical according to formula VIIIa where a'=2

Formula VIIIa

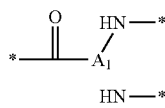

wherein GpR, GpG, GpL, GpH, GpC, $A_1$, r, g, h, l and l' are as defined above.

In one embodiment, said at least one hydrophobic radical -Hy is chosen among the radicals according to formula X wherein a=1 and a'=2 according to formula Xb as defined hereinafter:

Formula Xb

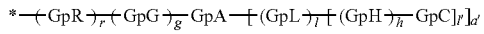

wherein GpA is a radical according to formula VIII and A is chosen among the radicals according to formula VIII' where s'=1 and GpA is a radical according to formula VIIIc Formula VIIIc

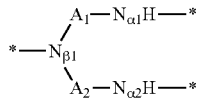

wherein GpR, GpG, GpL, GpH, GpC, $A_1$, $A_2$, r, g, h, l and l' are as defined above.

In one embodiment, said at least one hydrophobic radical -Hy is chosen among the radicals according to formula X wherein a=1 and a'=3 according to formula Xb as defined hereinafter:

Formula Xb

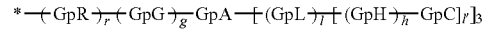

wherein GpA is a radical according to formula VIII and A is chosen among the radicals according to formula VIII''' where s'=1 and GpA is a radical according to formula VIIId Formula VIIId

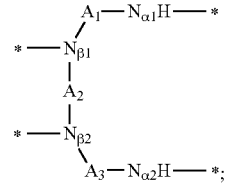

wherein GpR, GpG, GpL, GpH, GpC, $A_1$, $A_2$, $A_3$, r, g, h, l and l' are as defined above.

In one embodiment said at least one hydrophobic radical -Hy is chosen among the radicals according to formula X as defined above wherein l=0 according to formula Xd as defined hereinafter:

*-(-GpR-)-$_r$-(-GpG-)-$_g$-(GpA)$_a$-[-GpH-)-$_h$-GpC]$_{a'}$   Formula Xd wherein GpR, GpG, GpA, GpH, GpC, r, g, a, h and a' are as defined above.

In one embodiment, said at least one hydrophobic radical -Hy is chosen among the radicals according to formula X wherein -l=0,
according to formula Xd as defined hereinafter

*-(-GpR-)-$_r$-(-GpG-)-$_g$-(GpA)$_a$-[-GpH-)-$_h$-GpC]$_{a'}$   Formula Xd wherein
GpA is chosen among the radicals according to formula VIII wherein s'=1 represented by the formula VIIIa or according to formula VIII wherein s'=0 represented by the formula VIIIb:

Formula VIIIa

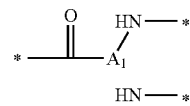

Formula VIIIb

b, c, d, e, g, h, r, and s' are as defined above;
GpR, GpH, GpG, GpC, $A_1$, B, Cx, G, H, R are as defined above;

In one embodiment said at least one hydrophobic radical -Hy is chosen among the radicals according to formula X as defined above wherein l=0 according to formula Xd as defined hereinafter:

*-(-GpR-)-$_r$-(-GpG-)-$_g$-(GpA)$_a$-[-GpH-)-$_h$-GpC]$_{a'}$   Formula Xd wherein
GpA is chosen among the radicals according to formula VIII wherein s'=1 represented by the formula VIIIc or the formula VIIId:

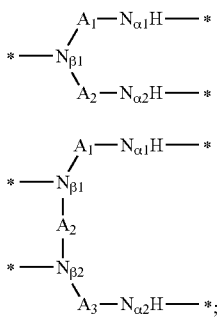

Formula VIIIc

Formula VIIId wherein GpR, GpG, GpH, GpC, $A_1$, $A_2$, $A_3$, r, g, a, h and a' are as defined above.

In one embodiment, the composition according to the invention is characterized in that said hydrophobic radicals are chosen among the hydrophobic radicals according to formula X wherein GpA is a radical according to formula VIIIb, a'=1 and l=0 represented by the formula Xe hereinafter:

*-(-GpR-)$_r$-(-GpG-)$_g$-(GpA)$_a$-(-GpH-)$_h$-GpC]     Formula Xe wherein GpR, GpG, GpA, GpH, GpC, r, g, h, and a are as defined above.

In one embodiment, the composition according to the invention is characterized in that said hydrophobic radicals are chosen among the hydrophobic radicals according to formula X wherein a'=2 and a=1 and l=0 represented by the formula Xf hereinafter:

*-(-GpR-)$_r$-(-GpG-)$_g$-GpA-[-GpH-)$_h$-GpC]$_2$     Formula Xf wherein GpR, GpG, GpA, GpH, GpC, r, g and h are as defined above.

In one embodiment, the composition according to the invention is characterized in that said hydrophobic radicals are chosen among the hydrophobic radicals according to formula X wherein h=0, l=0 and l'=1 represented by the formula Xg hereinafter:

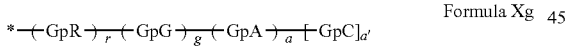

Formula Xg wherein GpR, GpG, GpA, GpC, r, g, a and a' are as defined above.

In one embodiment, the composition according to the invention is characterized in that said hydrophobic radicals are chosen among the hydrophobic radicals according to formula X wherein h=0, a'=1 represented by the formula Xh hereinafter:

*-(-GpR-)$_r$-(-GpG-)$_g$-(-GpA-)$_a$-GpC     Formula Xh wherein GpR, GpG, GpA, GpC, r, a and g are as defined above.

In one embodiment, the composition according to the invention is characterized in that said hydrophobic radicals are chosen among the hydrophobic radicals according to formula X wherein h=0, a'=2 and a=1 represented by the formula Xi hereinafter:

*-(-GpR-)$_r$-(-GpG-)$_g$-GpA-(GpC)$_2$     Formula Xi wherein GpR, GpG, GpA, GpC, r and g are as defined above.

In one embodiment said at least one hydrophobic radical -Hy is chosen among the radicals according to formula X as defined above wherein h=0 according to formula Xt as defined hereinafter:

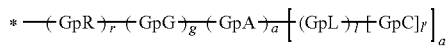

Formula Xt wherein GpR, GpG, GpA, GpL, GpC, r, g, a, l, l' and a' are as defined above.

In one embodiment said at least one hydrophobic radical -Hy is chosen among the radicals according to formula X as defined above wherein h and g=0 according to formula Xt' as defined hereinafter:

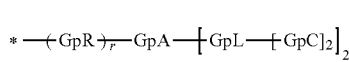

Formula Xt' wherein GpR, GpA, GpL, GpC and r are as defined above.

In one embodiment, the composition according to the invention is characterized in that said hydrophobic radicals are chosen among the hydrophobic radicals according to formula X wherein, l'=2 and a'=2 represented by the formula Xu hereinafter:

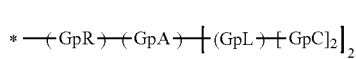

Formula Xu wherein GpR, GpA, GpL and GpC are as defined above.

In one embodiment, said at least one hydrophobic radical -Hy is chosen among the radicals according to formulas X, Xa to Xu:
wherein at least one of g and/or h is greater than or equal to 1
wherein GpC is a radical according to formula IX wherein e=0 and GpC is a radical according to formula IXa.

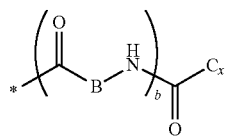

Formula IXa wherein B, b and Cx are as defined above.

In one embodiment, said at least one hydrophobic radical -Hy is chosen among the radicals according to formulas X, Xa to Xu wherein GpC is a radical according to formula IX wherein e=0 and GpC is a radical according to formula IXa,

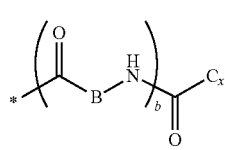

Formula IXa wherein B, b and Cx are as defined above.

In one embodiment, said at least one hydrophobic radical -Hy is chosen among the radicals according to formulas X, Xa to Xu wherein GpC is a radical according to formula IX wherein e=1, b=0 and GpC is a radical according to formula IXd.

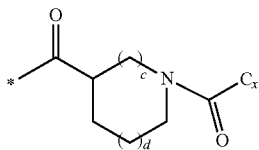

Formula IXd wherein c, d and Cx are as defined above.

In one embodiment, said at least one hydrophobic radical -Hy is chosen among the radicals according to formula X wherein GpC is a radical according to formula IX wherein e=0, b=0 and GpC is a radical according to formula IXc

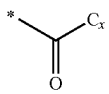

IXc wherein Cx is as defined above.

In one embodiment, said at least one hydrophobic radical -Hy is chosen among the radicals according to formulas X, Xa to Xu wherein GpC is a radical according to formula IX wherein e=1 and GpC is a radical according to formula IXb.

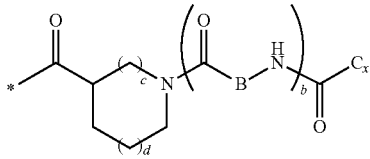

Formula IXb wherein c, d, B, b and Cx are as defined above.

In one embodiment, said at least one hydrophobic radical -Hy is chosen among the radicals according to formula X wherein
GpA is chosen among the radicals according to formula VIII wherein s'=1 represented by the formula VIIIa or according to formula VIII wherein s'=0 represented by the formula VIIIb:

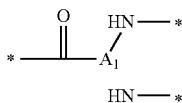

Formula VIIIa

Formula VIIIb wherein $A_1$ is as defined above.

In one embodiment, said at least one hydrophobic radical -Hy is chosen among the radicals according to formula X wherein GpA is chosen among the radicals according to formula VIII wherein s'=1 represented by the formula VIIIc or the formula VIIId:

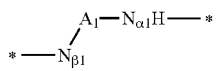

Formula VIIIc

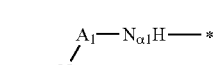

Formula VIIId wherein $A_1$, $A_2$ and $A_3$ are as defined above.

In one embodiment, if GpA is a radical according to formula VIIIc and r=1, then:
the GpC are bound directly or indirectly to $N_{\alpha 1}$ and $N_{\alpha 1}$ and the PLG is bound directly or indirectly via-GpR to $N_{\beta 1}$, or
the GpC are bound directly or indirectly to $N_{\alpha 1}$ and $N_{\beta 1}$, and the PLG is bound directly or indirectly via GpR to $N_{\alpha 2}$; or
the GpC are bound directly or indirectly to $N_{\alpha 2}$ and $N_{\beta 1}$, and the PLG is bound directly or indirectly via-GpR to $N_{\alpha 1}$.

In one embodiment, if GpA is a radical according to formula VIIIc and r=0, then:
the GpC are bound directly or indirectly to $N_{\alpha 1}$ and $N_{\alpha 2}$ and the PLG is bound directly or indirectly to $N_{\beta 1}$; or
the GpC are bound directly or indirectly to $N_{\alpha 1}$ and $N_{\beta 1}$, and the PLG is bound to directly or indirectly $N_{\alpha 2}$; or
the GpC are bound directly or indirectly to $N_{\alpha 2}$ and $N_{\beta 1}$, and the PLG is bound directly or indirectly to $N_{\alpha 1}$.

In one embodiment, if GpA is a radical according to formula VIIId and r=1, then
the GpC are bound directly or indirectly to $N_{\alpha 1}$, $N_{\alpha 2}$ and $N_{\beta 1}$ and the PLG is bound directly or indirectly via GpR to $N_{\beta 2}$; or
the GpC are bound directly or indirectly to $N_{\alpha 1}$, $N_{\alpha 2}$ and $N_{\beta 2}$ and the PLG is bound directly or indirectly via GpR to $N_{\alpha 1}$; or
the GpC are bound directly or indirectly to $N_{\alpha 1}$, $N_{\beta 1}$ and $N_{\beta 2}$ and the PLG is bound directly or indirectly via -GpR- to $N_{\alpha 2}$; or
the GpC are bound directly or indirectly to $N_{\alpha 2}$, $N_{\beta 1}$ and $N_{\alpha 2}$ and the PLG is bound directly or indirectly via GpR to $N_{\alpha 1}$.

In one embodiment, if GpA is a radical according to formula VIIId r=0, then
the GpC are bound directly or indirectly to $N_{\alpha 1}$, $N_{\alpha 2}$ and $N_{\beta 1}$ and the PLG is bound directly or indirectly to $N_{\alpha 2}$; or
the GpC are bound directly or indirectly to $N_{\alpha 1}$, $N_{\alpha 2}$ and $N_{\beta 2}$ and the PLG is bound directly or indirectly to $N_{\alpha 2}$; or
the GpC are bound directly or indirectly to $N_{\alpha 2}$, $N_{\beta 1}$ and $N_{\beta 2}$ and the PLG is bound directly or indirectly to $N_{\alpha 2}$; or
the GpC are bound directly or indirectly to $N_{\alpha 2}$, $N_{\beta 1}$ and $N_{\alpha 2}$ and the PLG is bound directly or indirectly to $N_{\alpha 1}$.

In the formulas, the * indicate the binding sites of the hydrophobic radicals to the PLG or between the different groups GpR, GpG, GpA, GpL, GpH and GpC to form amide functions.

The radicals -Hy are bounded to the PLG via amide functions.

In the formulas VII, VII' and VII", the * indicate, from left to right respectively, the binding sites of GpR:
to the PLG and
to GpR if r=2 or to GpG if g≥1 or to GpA if g=0 or to GpL if l=1 and g=a=0 or to GpH if h≥1 and g=a=l=0 or GpC if a'=1 and g=a=l=h=0.

In the formulas VIIIa, VIIIb, VIIIc and VIIId, the * indicate, from left to right respectively, the binding sites of GpA:
to GpG if g≥1 or to GpR if r=1 or 2 and g=0 or to the PLG if g=r=0 and
to GpL if l=1 or to GpH if h≥1 and l=0 or to GpC if l=h=0

In the formula IX, the * indicates the binding site of GpC:
to GpH if h≥1,
to GpL if l=1 and h=0
to GpA if a=1 and h=l=0
to GpG if g≥1 and h=l=a=0
to GpR if r=1 or 2 and h=l=a=g=0
to the PLG if h=l=a=g=r=0

In one embodiment, a=0.
In one embodiment, h=1 and g=0.
In one embodiment, h=0 and g=1.
In one embodiment, r=0, g=1 and h=0.
In one embodiment, r=1 and GpR is chosen among the radicals according to formula VII' or VII" and h=0.
In one embodiment, r=1, g=0 and GpR is a radical according to formula VII' and h=0.
In one embodiment, r=1, g=0 and GpR is a radical according to formula VII' and h=1.
In one embodiment, r=1, g=0, GpR is a radical according to formula VII', GpA is chosen among the radicals according to formula VIIIa or VIIIb and h=0.
In one embodiment, r=1, g=0, GpR is a radical according formula VII', GpA is chosen among the radicals according to formula VIIIa or VIIIb and h=1.
In one embodiment, r=1, g=0, GpR is a radical according to formula VII', GpA is a radical according to formula VIIIa and h=0.
In one embodiment, r=1, g=0, GpR is a radical according to formula VII', GpA is a radical according to formula VIIIa and h=1.
In one embodiment, r=1, g=0, GpR is a radical according to formula VII', GpA is a radical according to formula VIIIb and h=0.
In one embodiment, r=1, g=0, GpR is a radical according to formula VII', GpA is a radical according to formula VIIIb and h=1.
In one embodiment, r=0, g=0 and GpA is chosen among the radicals according to formula VIIIa and VIIIb.
In one embodiment, r=0, g=0, GpA is chosen among the radicals according to formula VIIIa and VIIIb and h=0.
In one embodiment, g+h≥2.
In one embodiment, g is greater than or equal to 2 (g≥2).
In one embodiment, h is greater than or equal to 2 (h≥2).
In one embodiment, g+h≥2 and a and l are equal to 0 (a=l=0).
In one embodiment, g+h≥2 and b is equal to 0 (b=0).
In one embodiment, g or h is greater than or equal to 2 (g≥2) and b is equal to 0.
In one embodiment, g+h≥2, b is equal to 0 (b=0) and e is equal to 1 (e=1).

In one embodiment, g or h is greater than or equal to 2 (g≥2), b is equal to 0 (b=0) and e is equal to 1 (e=1).

In one embodiment, the composition is characterized in that the hydrophobic radical according to formula X is a radical wherein R is a divalent linear alkyl radical comprising from 2 to 12 carbon atoms.

In one embodiment, the composition is characterized in that the hydrophobic radical according to formula X is a radical wherein R is a divalent alkyl radical comprising from 2 to 6 carbon atoms.

In one embodiment, the composition is characterized in that the hydrophobic radical according to formula X is a radical wherein R is a divalent linear alkyl radical comprising from 2 to 6 carbon atoms.

In one embodiment, the composition is characterized in that the hydrophobic radical according to formula X is a radical wherein R is a divalent alkyl radical comprising from 2 to 4 carbon atoms.

In one embodiment, the composition is characterized in that the hydrophobic radical according to formula X is a radical wherein R is a divalent linear alkyl radical comprising from 2 to 4 carbon atoms.

In one embodiment, the composition is characterized in that the hydrophobic radical according to formula X is a radical wherein R is a divalent alkyl radical comprising 2 carbon atoms.

In one embodiment, the composition is characterized in that the hydrophobic radical according to formula X is a radical wherein R is a divalent linear alkyl radical comprising from 1 to 11 carbon atoms.

In one embodiment, the composition is characterized in that the hydrophobic radical according to formula X is a radical wherein R is a divalent alkyl radical comprising from 1 to 6 carbon atoms.

In one embodiment, the composition is characterized in that the hydrophobic radical according to formula X is a radical wherein R is a divalent alkyl radical comprising from 2 to 5 carbon atoms and bearing one or a plurality of amide functions (—CONH$_2$).

In one embodiment, the composition is characterized in that the hydrophobic radical according to formula X is a radical wherein R is a divalent linear alkyl radical comprising from 2 to 5 carbon atoms and bearing one or a plurality of amide functions (—CONH$_2$).

In one embodiment, the composition is characterized in that the hydrophobic radical according to formula X is a radical wherein R is a radical chosen in the group consisting of the radicals represented by the formulas hereinafter:

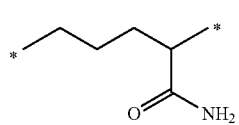

Formula X1

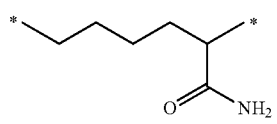

Formula X2

In one embodiment, the composition is characterized in that the hydrophobic radical according to formula X is a radical wherein R is a radical according to formula X1.

In one embodiment, the composition is characterized in that the hydrophobic radical according to formula X is a radical wherein R is a radical according to formula X2.

In one embodiment, the composition is characterized in that the hydrophobic radical according to formula X is a radical wherein R is bound to the co-polyamino acid via an amide function borne by the carbon in the delta or epsilon position (or in position 4 or 5) with respect to the amide function (—CONH2).

In one embodiment, the composition is characterized in that the hydrophobic radical according to formula X is a radical wherein R is a non-substituted ether or polyether linear radical comprising from 4 to 14 carbon atoms and from 1 to 5 oxygen atoms.

In one embodiment, the composition is characterized in that the hydrophobic radical according to formula X is a radical wherein R is an ether radical.

In one embodiment, the composition is characterized in that the hydrophobic radical according to formula X is a radical wherein R is an ether radical comprising from 4 to 6 carbon atoms.

In one embodiment, the composition is characterized in that the hydrophobic radical according to formula X is a radical wherein R is a divalent alkyl radical comprising 6 carbon atoms.

In one embodiment, the composition is characterized in that the hydrophobic radical according to formula X is a radical wherein R is an ether radical represented by the formula

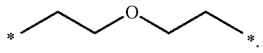

In one embodiment, the composition is characterized in that the hydrophobic radical according to formula X is a radical wherein R is a polyether radical.

In one embodiment, the composition is characterized in that the hydrophobic radical according to formula X is a radical wherein R is a polyether linear radical comprising from 6 to 10 carbon atoms and from 2 to 3 oxygen atoms.

In one embodiment, the composition is characterized in that the hydrophobic radical according to formula X is a radical wherein R is a polyether radical chosen in the group consisting of the radicals represented by the formulas hereinafter:

Formula X3
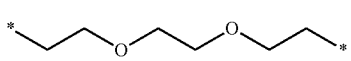

Formula X4
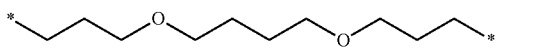

Formula X5

Formula X6
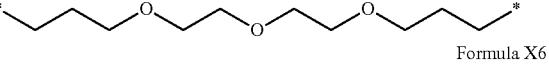

In one embodiment, the composition is characterized in that the hydrophobic radical according to formula X is a radical wherein R is a radical according to formula X3.

In one embodiment, the composition is characterized in that the hydrophobic radical according to formula X is a radical wherein R is a radical according to formula X4.

In one embodiment, the composition is characterized in that the hydrophobic radical according to formula X is a radical wherein R is a radical according to formula X5.

In one embodiment, the composition is characterized in that the hydrophobic radical according to formula X is a radical wherein R is a radical according to formula X6.

In one embodiment, the composition is characterized in that the hydrophobic radical according to formula X is a radical wherein R is a polyether radical chosen in the group consisting of the radicals represented by the formulas x5 and X6 hereinafter:

Formula X5
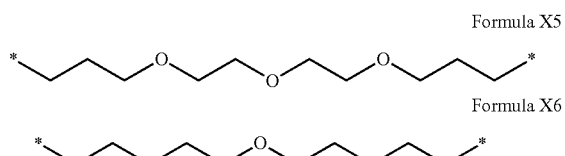

Formula X6

In one embodiment, the composition is characterized in that the hydrophobic radical according to formula X is a radical wherein the radical GpG and/or GpH is according to formula XI' wherein G is an alkyl radical comprising 6 carbon atoms represented by the formula Z hereinafter:

Formula Z
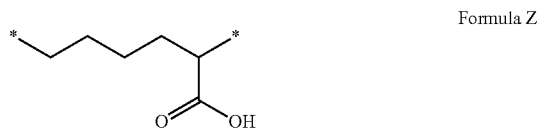 [SMILES: *CCCCC(*)C(=O)O]

In one embodiment, the composition is characterized in that the hydrophobic radical according to formula X is a radical wherein the radical GpG and/or GpH is according to formula XI wherein G is an alkyl radical comprising 4 carbon atoms represented by the formula Z' hereinafter:

Formula Z'

In one embodiment, the composition is characterized in that the hydrophobic radical according to formula X is a radical wherein the radical GpG and/or GpH is according to formula XI wherein G is an alkyl radical comprising 4 carbon atoms represented by —(CH2)2-CH(COOH)—.

In one embodiment, the composition is characterized in that the hydrophobic radical according to formula X is a radical wherein the radical GpG and/or GpH is according to formula XI wherein G is an alkyl radical comprising 4 carbon atoms represented by —CH((CH2)2COOH)—.

In one embodiment, the composition is characterized in that the hydrophobic radical according to formula X is a radical wherein the radical GpG and/or GpH is according to formula XI wherein G is an alkyl radical comprising 3 carbon atoms represented by —CH2-CH—(COOH).

In one embodiment, the composition is characterized in that the hydrophobic radical according to formula X is a radical wherein the radical GpG and/or GpH is according to formula XI wherein G is an alkyl radical comprising 3 carbon atoms represented by —CH(CH2)(COOH)—.

In one embodiment, the composition is characterized in that the hydrophobic radical according to formula X is a radical wherein the radical GpA is according to formula VIII and wherein $A_1$, $A_2$ or $A_3$ is chosen in the group consisting of radicals represented by the formulas hereinafter:

Formula Y1

Formula Y2

Formula Y3

Formula Y4

Formula Y5

Formula Y6

Formula Y7

Formula Y8

Formula Y9

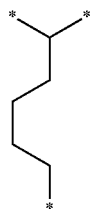

Formula Y10

In one embodiment, the composition is characterized in that the hydrophobic radical according to formula X is a radical wherein the radical GpC according to formula IX is chosen in the group consisting of the radicals according to formulas IXe, IXf or IXg represented hereinafter:

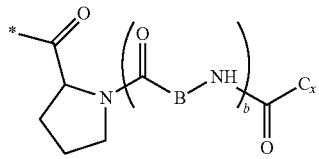

Formula IXe

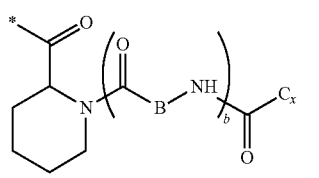

Formula IXVf

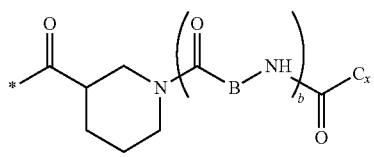

Formula IXg

In one embodiment, the composition is characterized in that the hydrophobic radical according to formula X is a radical wherein the radical GpC according to formula IX is chosen in the group consisting of the radicals according to formulas IXe, IXf or IXg wherein b is equal to 0, responding respectively to formulas IXh, IXi, and IXj represented hereinafter:

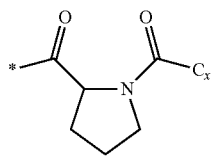

Formula IXh

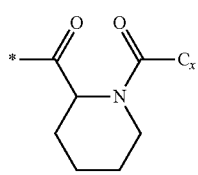

Formula IXi

Formula IXj

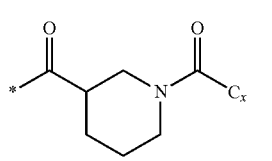

In one embodiment, the composition is characterized in that the hydrophobic radical according to formula X is a radical wherein the radical GpC responds to formula IX or IXe wherein b=0, and responds to formula IVh.

In one embodiment, the composition is characterized in that the hydrophobic radical according to formula X is a radical wherein Cx is chosen in the group consisting of linear alkyl radicals.

In one embodiment, the composition is characterized in that the hydrophobic radical according to formula X is a radical wherein Cx is chosen in the group consisting of branched alkyl radicals.

In one embodiment, the composition is characterized in that the hydrophobic radical according to formula X is a radical wherein Cx is chosen in the group consisting of alkyl radicals comprising from 9 to 14 carbon atoms.

In one embodiment, the composition is characterized in that the hydrophobic radical according to formula X is a radical wherein Cx is chosen in the group consisting of the radicals represented by the formulas hereinafter:

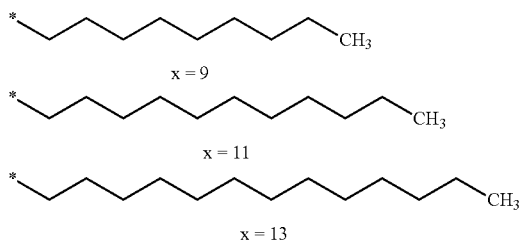

In one embodiment, the composition is characterized in that the hydrophobic radical according to formula X is a radical wherein Cx is chosen in the group consisting of alkyl radicals comprising from 15 to 16 carbon atoms.

In one embodiment, the composition is characterized in that the hydrophobic radical according to formula X is a radical wherein Cx is chosen in the group consisting of the radicals represented by the formulas hereinafter:

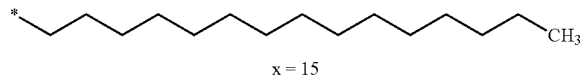 [SMILES: *CCCCCCCCCCCCCCC]

In one embodiment, the composition is characterized in that the hydrophobic radical according to formula X is a radical wherein Cx is chosen in the group consisting of the radicals represented by the formulas hereinafter:

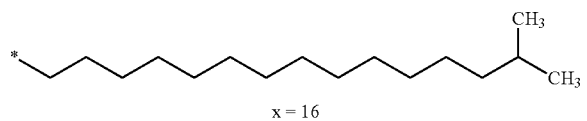 [SMILES: *CCCCCCCCCCCCCC(C)C]

In one embodiment, the composition is characterized in that the hydrophobic radical according to formula X is a radical wherein Cx is chosen in the group consisting of alkyl radicals comprising from 17 to 25 carbon atoms.

In one embodiment, the composition is characterized in that the hydrophobic radical according to formula X is a radical wherein Cx is chosen in the group consisting of alkyl radicals comprising from 17 to 18 carbon atoms.

In one embodiment, the composition is characterized in that the hydrophobic radical according to formula X is a radical wherein Cx is chosen in the group consisting of the alkyl radicals represented by the formulas hereinafter:

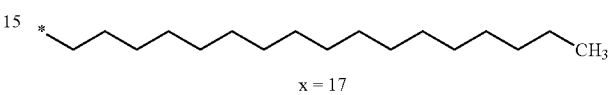

In one embodiment, the composition is characterized in that the hydrophobic radical according to formula X is a radical wherein Cx is chosen in the group consisting of alkyl radicals comprising from 18 to 25 carbon atoms.

In one embodiment, the composition is characterized in that the hydrophobic radical according to formula X is a radical wherein Cx is chosen in the group consisting of the alkyl radicals represented by the formulas hereinafter:

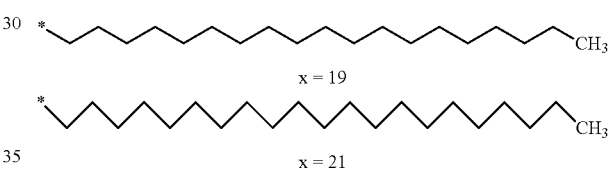

In one embodiment, the composition is characterized in that the hydrophobic radical is a radical according to formula X wherein the radical GpC according to formula IV is chosen in the group consisting of the radicals wherein Cx is chosen in the group consisting of alkyl radicals comprising 14 or 15 carbon atoms.

In one embodiment, the composition is characterized in that the hydrophobic radical is a radical according to formula X wherein the radical GpC according to formula IV is chosen in the group consisting of the radicals wherein Cx is chosen in the group consisting of the radicals represented by the formulas hereinafter:

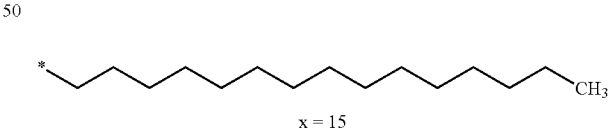

n one embodiment, when l' or a'=1, x is comprised from 11 to 25 (11≤x≤25). In particular, when x is comprised from 15 to 16 (x=15 or 16) then r=1 and R is an ether or polyether radical and when x is greater than 17 (x≥17) then r=1 and R is an ether or polyether radical.

In one embodiment, when l' or a'=2, x is comprised from 9 to 15 (9≤x≤15).

In one embodiment, the composition is characterized in that the ratio M between the number of hydrophobic radicals and the number of glutamic or aspartic units is comprised from 0.007 to 0.35.

In one embodiment, the composition is characterized in that the ratio M between the number of hydrophobic radicals and the number of glutamic or aspartic units is comprised from 0.007 to 0.3.

In one embodiment, the composition is characterized in that the ratio M between the number of hydrophobic radicals and the number of glutamic or aspartic units is comprised from 0.01 to 0.3.

In one embodiment, the composition is characterized in that the ratio M between the number of hydrophobic radicals and the number of glutamic or aspartic units is comprised from 0.02 to 0.2.

In one embodiment, the composition is characterized in that the hydrophobic radical observes the formula X and the ratio M between the number of hydrophobic radicals and the number of glutamic or aspartic units is comprised from 0.007 to 0.15.

In one embodiment, the composition is characterized in that the hydrophobic radical observes the formula X and the ratio M between the number of hydrophobic radicals and the number of glutamic or aspartic units is comprised from 0.01 to 0.1.

In one embodiment, the composition is characterized in that the hydrophobic radical observes the formula X and the ratio M between the number of hydrophobic radicals and the number of glutamic or aspartic units is comprised from 0.02 to 0.08.

In one embodiment, the composition is characterized in that the hydrophobic radical observes the formula X and the ratio M between the number of hydrophobic radicals and the number of glutamic or aspartic units is comprised from 0.007 to 0.3.

In one embodiment, the composition is characterized in that the hydrophobic radical observes the formula X and the ratio M between the number of hydrophobic radicals and the number of glutamic or aspartic units is comprised from 0.01 to 0.3.

In one embodiment, the composition is characterized in that the hydrophobic radical observes the formula X and the ratio M between the number of hydrophobic radicals and the number of glutamic or aspartic units is comprised from 0.015 to 0.2.

In one embodiment, the composition is characterized in that the hydrophobic radical observes the formula X wherein the radical Cx comprises from 9 to 10 carbon atoms and the ratio M between the number of hydrophobic radicals and the number of glutamic or aspartic units is comprised from 0.03 to 0.15.

In one embodiment, the composition is characterized in that the hydrophobic radical observes the formula X wherein the radical Cx comprises from 11 to 12 carbon atoms and the ratio M between the number of hydrophobic radicals and the number of glutamic or aspartic units is comprised from 0.015 to 0.2.

In one embodiment, the composition is characterized in that the hydrophobic radical observes the formula X wherein the radical Cx comprises from 11 to 12 carbon atoms and the ratio M between the number of hydrophobic radicals and the number of glutamic or aspartic units is comprised from 0.015 to 0.1.

In one embodiment, the composition is characterized in that the hydrophobic radical observes the formula X wherein the radical Cx comprises from 11 to 12 carbon atoms and the ratio M between the number of hydrophobic radicals and the number of glutamic or aspartic units is comprised from 0.02 to 0.08.

In one embodiment, the composition is characterized in that the hydrophobic radical observes the formula X wherein the radical Cx comprises from 13 to 15 carbon atoms and the ratio M between the number of hydrophobic radicals and the number of glutamic or aspartic units is comprised from 0.01 to 0.1.

In one embodiment, the composition is characterized in that the hydrophobic radical observes the formula X wherein the radical Cx comprises from 13 to 15 carbon atoms and the ratio M between the number of hydrophobic radicals and the number of glutamic or aspartic units is comprised from 0.01 to 0.06.

In one embodiment, the composition is characterized in that the hydrophobic radical observes the formula X wherein the radical Cx comprises from 11 to 14 carbon atoms and the ratio M between the number of hydrophobic radicals and the number of glutamic or aspartic units is comprised from 0.1 to 0.2.

In one embodiment, the composition is characterized in that the hydrophobic radical observes the formula X wherein the radical Cx comprises from 15 to 16 carbon atoms and the ratio M between the number of hydrophobic radicals and the number of glutamic or aspartic units is comprised from 0.04 to 0.15.

In one embodiment, the composition is characterized in that the hydrophobic radical observes the formula X wherein the radical Cx comprises from 17 to 18 carbon atoms and the ratio M between the number of hydrophobic radicals and the number of glutamic or aspartic units is comprised from 0.02 to 0.06.

In one embodiment, the composition is characterized in that the hydrophobic radical observes the formula X wherein the radical Cx comprises from 19 to 25 carbon atoms and the ratio M between the number of hydrophobic radicals and the number of glutamic or aspartic units is comprised from 0.01 to 0.06.

In one embodiment, the composition is characterized in that the hydrophobic radical observes the formula X wherein the radical Cx comprises from 19 to 25 carbon atoms and the ratio M between the number of hydrophobic radicals and the number of glutamic or aspartic units is comprised from 0.01 to 0.05.

The hydrophobic radical to basal insulin ratio is defined as the ratio of their respective molar concentrations: [Hy]/[basal insulin] (mol/mol) to obtain the expected performances, namely the solubilization of the basal insulin at pH from 6.0 to 8.0, the precipitation of the basal insulin and the stability of the compositions according to the invention.

The minimum value of the hydrophobic radical to basal insulin ratio [Hy]/[basal insulin] measured is the value at which the basal insulin is solubilized, as solubilization is the minimum effect to be obtained; this solubilization is the prerequisite for all the other technical effects which can only be observed if the basal insulin is solubilized at pH from 6.0 to 8.0.

In the compositions according to the invention, the hydrophobic radical to basal insulin ratio [Hy]/[basal insulin] may be greater than the minimum value determined by the limit of solubilization.

In one embodiment, the hydrophobic radical to basal insulin ratio [Hy]/[basal insulin]≤3.

In one embodiment, the hydrophobic radical to basal insulin ratio [Hy]/[basal insulin]≤2.

In one embodiment, the hydrophobic radical to basal insulin ratio [Hy]/[basal insulin]≤1.75.

In one embodiment, the hydrophobic radical to basal insulin ratio [Hy]/[basal insulin]≤1.5.

In one embodiment, the hydrophobic radical to basal insulin ratio [Hy]/[basal insulin]≤1.25.

In one embodiment, the hydrophobic radical to basal insulin ratio [Hy]/[basal insulin]≤1.00.

In one embodiment, the hydrophobic radical to basal insulin ratio [Hy]/[basal insulin]≤0.75.

In one embodiment, the hydrophobic radical to basal insulin ratio [Hy]/[basal insulin]≤0.5.

In one embodiment, the hydrophobic radical to basal insulin ratio [Hy]/[basal insulin]≤0.25.

The invention also relates to a method for preparing stable injectable compositions.

The invention also relates to said co-polyamino acids I, bearing carboxylate charges and hydrophobic radicals according to formula X and the precursors of said hydrophobic radicals.

The invention also relates to a co-polyamino acid bearing carboxylate charges and at least one hydrophobic radical according to formula X, said co-polyamino acid being chosen among the co-polyamino acids according to formula I:

   Formula I

Wherein:
j≥1; 0≤j'≤n'1 and j+j'≥1 and k≥2 said co-polyamino acid according to formula I bearing at least one hydrophobic radical -Hy, carboxylate charges and consisting of at least two chains of glutamic or aspartic units PLG bound together by an at least divalent linear or branched radical or spacer Q[-*]$_k$ consisting of an alkyl chain comprising one or a plurality of heteroatoms chosen in the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions, said radical or spacer Q[-*]$_k$ being bound to at least two glutamic or aspartic unit chains PLG by an amide function and, said amide functions binding said radical or spacer Q[-*]$_k$ bound to said at least two chains of glutamic or aspartic units result from the reaction between an amine function and an acid function respectively borne either by the precursor Q' of the radical or spacer Q[-*]$_k$ or by a glutamic or aspartic unit, said hydrophobic radical -Hy being bound either to a terminal "amino acid" unit and then j≥1, or to a carboxyl function borne by one of the chains of the glutamic or aspartic units PLG and then j'=n'1 and n'1 is the mean number of monomeric units bearing a hydrophobic radical -Hy.

The co-polyamino acids bearing carboxylate charges and hydrophobic radicals according to formula I are soluble in distilled water at a pH from 6.0 to 8.0, at a temperature of 25° C. and at a concentration below 100 mg/ml.

In one embodiment, the invention also relates to the precursors Hy' of said hydrophobic radicals according to formula X' as defined hereinafter:

Formula X'

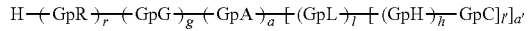

wherein

GpR is chosen among the radicals according to formulas VII, VII' or VII":

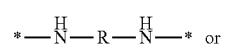   Formula VII

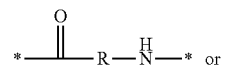   Formula VII'

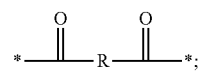   Formula VII"

GpG and GpH identical or different are chosen among the radicals according to formulas XI or XI':

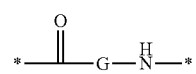   Formula XI

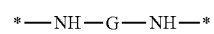   Formula XI'

GpA is chosen among the radicals according to formula VIII

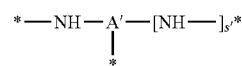   Formula VIII

Wherein A' is chosen among the radicals according to VIII', VIII" or VIII'"

   Formula VIII'

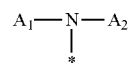   Formula VIII"

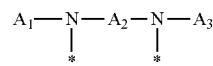   Formula VIII'"

GpL is chosen among the radicals according to formula XII

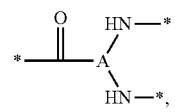   Formula XII

GpC is a radical according to formula IX:

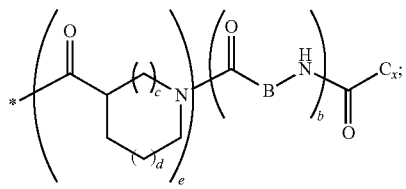

Formula IX the * indicate the binding sites of the different groups bound by amide functions;

a is an integer equal to 0 or to 1 and a'=1 if a=0 and a'=1, 2 or 3 if a=1;

a' is an integer equal to 1, to 2 or to 3 b is an integer equal to 0 or to 1;

c is an integer equal to 0 or to 1, and if c is equal to 0 then d is equal to 1 or to 2;

d is an integer equal to 0, to 1 or to 2;

e is an integer equal to 0 or to 1;

g is an integer equal to 0, to 1, to 2, to 3 to 4 to 5 or to 6;

h is an integer equal to 0, to 1, to 2, to 3 to 4 to 5 or to 6;

l is an integer equal to 0 or 1 and l'=1 if l=0 and l'=2 if l=1;

l' is an integer equal to 1 or to 2;

r is an integer equal to 0, 1 or to 2, and s' is an integer equal to 0 or 1;

A, $A_1$, $A_2$ and $A_3$ identical or different are linear or branched alkyl radicals comprising from 1 to 8 carbon atoms and optionally substituted by a radical from a saturated, unsaturated or aromatic ring;

B is a radical chosen in the group consisting of a non-substituted ether or polyether radical comprising from 4 to 14 carbon atoms and from 1 to 5 oxygen atoms or a linear or branched alkyl radical, optionally comprising an aromatic nucleus, comprising from 1 to 9 carbon atoms;

$C_x$ is a radical chosen in the group consisting of a linear or branched monovalent alkyl radical, optionally comprising a cyclic part, wherein x indicates the number of carbon atoms and $6 \leq x \leq 25$:

When the hydrophobic radical -Hy bears 1-GpC, then $9 \leq x \leq 25$,

When the hydrophobic radical -Hy bears 2-GpC, then $9 \leq x \leq 15$,

When the hydrophobic radical -Hy bears 3-GpC, then $7 \leq x \leq 13$,

When the hydrophobic radical -Hy bears 4-GpC, then $7 \leq x \leq 11$,

When the hydrophobic radical -Hy bears at least 5-GpC, then $6 \leq x \leq 11$,

G is a linear or branched divalent alkyl radical comprising from 1 to 8 carbon atoms, said alkyl radical bearing one or a plurality of free carboxylic acid function(s).

R is a radical chosen in the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms:

The hydrophobic radical(s) -Hy according to formula X being bound to the PLG:
via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, and
via a covalent bond between a nitrogen atom of the hydrophobic radical -Hy and a carbonyl borne by the PLG thus forming an amide function obtained from the reaction of an amine function of the precursor -Hy' of the hydrophobic radical -Hy and an acid function borne by the PLG,
the ratio M between the number of hydrophobic radicals and the number of glutamic or aspartic units being between $0 < M \leq 0.5$;
when a plurality of hydrophobic radicals are borne by a co-polyamino acid then they are identical or different,
the degree of polymerization DP in glutamic or aspartic units for the PLG chains is comprised from 5 to 250;
the free carboxylic acid functions being in the form of alkali cation salt chosen in the group consisting of $Na^+$ and $K^+$.

In one embodiment, the co-polyamino acid is chosen in the group of co-polyamino acids according to formula I, wherein $Q[-*]_k$ is a radical according to formula III.

In one embodiment, the co-polyamino acid is a sodium poly-L-glutamate modified at two of its extremities thereof, according to the formula represented hereinafter, described in example B14.

B14

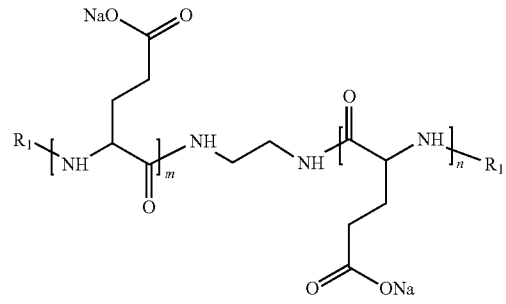

i = 0.072, DP (m + n) = 24
$R_1$ = H, pyroglutamate or

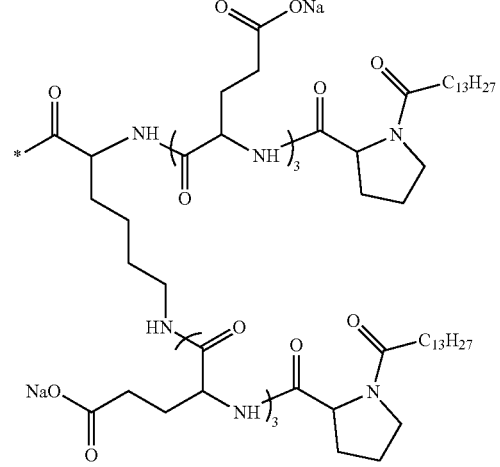

In one embodiment, the co-polyamino acid is a sodium poly-L-glutamate modified at two of its extremities thereof, according to the formula represented hereinafter, described in example B19.

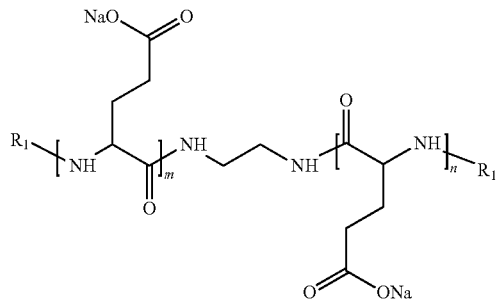

i = 0.066, DP (m + n) = 24

$R_1$ = H, pyroglutamate or

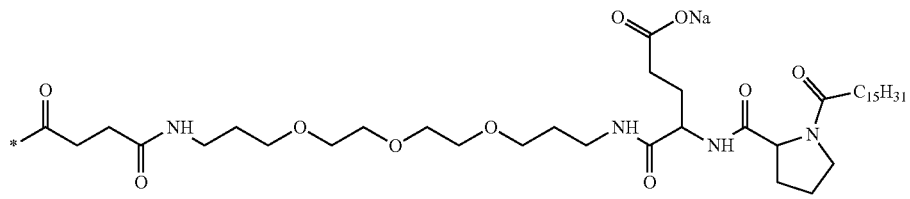

In one embodiment, the co-polyamino acid is a sodium poly-L-glutamate modified at two of its extremities thereof, according to the formula represented hereinafter, described in example B23.

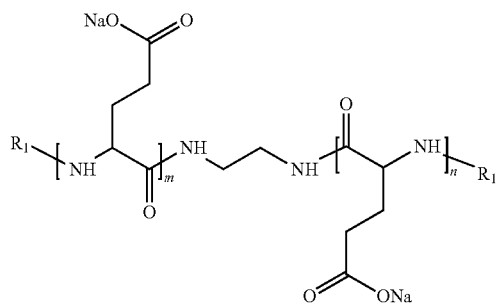

i = 0.080, DP (m + n) = 24

$R_1$ = H, pyroglutamate or

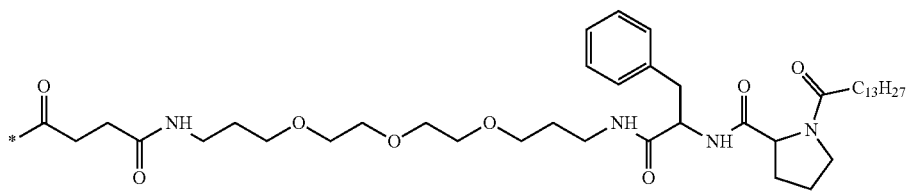

In one embodiment, the composition according to the invention is characterized in that the co-polyamino acid is obtained from a polyamino acid obtained by polymerization.

In one embodiment, the composition according to the invention is characterized in that the co-polyamino acid is obtained from a polyamino acid obtained by ring-opening polymerization of a glutamic acid N-carboxyanhydride derivative or of an aspartic acid N-carboxyanhydride derivative.

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative as described in the journal article Adv. Polym. Sci. 2006, 202, 1-18 (Deming, T. J.).

In one embodiment, the composition according to the invention is characterized in that the co-polyamino acid is obtained from a polyamino acid obtained by polymerization of a glutamic acid N-carboxyanhydride derivative.

In one embodiment, the composition according to the invention is characterized in that the co-polyamino acid is obtained from a polyamino acid obtained by polymerization of a glutamic acid N-carboxyanhydride derivative chosen in the group consisting of poly-methyl glutamate N-carboxyanhydride (GluOMe-NCA), poly-benzyl glutamate N-carboxyanhydride (GluOBzl-NCA) poly-t-butyl glutamate N-carboxyanhydride (GluOtBu-NCA).

In one embodiment, the glutamic acid N-carboxyanhydride derivative is the poly-L-methyl glutamate N-carboxyanhydride (L-GluOMe-NCA).

In one embodiment, the glutamic acid N-carboxyanhydride derivative is the poly-L-benzyl glutamate N-carboxyanhydride (L-GluOBzl-NCA).

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative using an organometallic complex as initiator as described in the publication Nature 1997, 390, 386-389 (Deming, T. J.).

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative using ammonia or a primary amine as initiator as described in the patent FR 2,801,226 (Touraud, F.; et al.) and the references cited by this patent. Similarly, the initiator may be a polyamine in order to obtain polyamino acid comprising a plurality of PLGs. Said polyamines may be chosen among diamines, triamines and tetramines. The amines of these polyamines may be primary amines.

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative using hexamethyldisilazane as initiator as described in the publication J. Am. Chem. Soc. 2007, 129, 14114-14115 (Lu H.; et al.) or a silylated amine as described in the publication J. Am. Chem. Soc. 2008, 130, 12562-12563 (Lu H.; et al.).

In one embodiment, the composition according to the invention is characterized in that the synthesis method of the polyamino acid obtained by polymerization of a glutamic acid N-carboxyanhydride derivative or of an aspartic acid N-carboxyanhydride derivative from which the co-polyamino acid is obtained comprises an ester function hydrolysis step.

In one embodiment, this ester function hydrolysis step may consist of a hydrolysis in acidic medium or a hydrolysis in basic medium or be performed by hydrogenation.

In one embodiment, this ester group hydrolysis step is a hydrolysis in acidic medium.

In one embodiment, this ester group hydrolysis step is performed by hydrogenation.

In one embodiment, the composition according to the invention is characterized in that the co-polyamino acid is obtained from a polyamino acid obtained by depolymerization of a polyamino acid of higher molecular weight.

In one embodiment, the composition according to the invention is characterized in that the co-polyamino acid is obtained from a polyamino acid obtained by enzymatic depolymerization of a polyamino acid of higher molecular weight.

In one embodiment, the composition according to the invention is characterized in that the co-polyamino acid is obtained from a polyamino acid obtained by chemical depolymerization of a polyamino acid of higher molecular weight.

In one embodiment, the composition according to the invention is characterized in that the co-polyamino acid is obtained from a polyamino acid obtained by enzymatic and chemical depolymerization of a polyamino acid of higher molecular weight.

In one embodiment, the composition according to the invention is characterized in that the co-polyamino acid is obtained from a polyamino acid obtained by depolymerization of a polyamino acid of higher molecular weight chosen in the group consisting of sodium polyglutamate and sodium polyaspartate.

In one embodiment, the composition according to the invention is characterized in that the co-polyamino acid is obtained from a polyamino acid obtained by depolymerization of a sodium polyglutamate of higher molecular weight.

In one embodiment, the composition according to the invention is characterized in that the co-polyamino acid is obtained from a polyamino acid obtained by depolymerization of a sodium polyaspartate of higher molecular weight.

In one embodiment, the composition according to the invention is characterized in that the co-polyamino acid is obtained by grafting a hydrophobic group on a poly-L-glutamic acid or poly-L-aspartic acid using amide bond formation methods well-known to those skilled in the art.

In one embodiment, the composition according to the invention is characterized in that the co-polyamino acid is obtained by grafting a hydrophobic group on a poly-L-glutamic acid or poly-L-aspartic acid using amide bond formation methods used for peptide synthesis.

In one embodiment, the composition according to the invention is characterized in that the co-polyamino acid is obtained by grafting a hydrophobic group on a poly-L-glutamic acid or poly-L-aspartic acid as described in the patent FR 2,840,614 (Chan, Y. P.; et al.).

During synthesis of the intermediate compounds Hy and during grafting, conventional protection and deprotection techniques are used:

the one or a plurality of free carboxylic acid function(s) of Hy may be in protected form prior to grafting on the PLG via an acid protecting group, this protection is performed for example by esterification using methanol, ethanol, benzyl alcohol or t-Butanol. After grafting, the functions are deprotected, i.e. a deprotection reaction is carried out so that the carboxylic function(s) is/are free or in the form of alkali cation salt chosen in the group consisting of Na+ and K+.

the one or a plurality of amine function(s) may be in protected form prior to grafting on the PLG via an amine protecting group, this protection is performed for example by acid or basic hydrolysis with heat via the phenylmethoxycarbonyl group or the 1,1-dimethylethoxycarbonyl group. After grafting, the functions are deprotected, i.e. a deprotection reaction is carried out so that the amine functions is/are free.

Hereinafter, the units used are for the insulins those recommended by pharmacopeias, the equivalences in mg/ml whereof are given in the table hereinafter:

| Insulin | EP Pharmacopeia 8.0 (2014) | US Pharmacopeia-USP38 (2015) |
|---|---|---|
| Aspart | 1U = 0.0350 mg of insulin aspart | 1 USP = 0.0350 mg of insulin aspart |
| Lispro | 1U = 0.0347 mg of insulin lispro | 1 USP = 0.0347 mg of insulin lispro |
| Human | 1IU = 0.0347 mg of human insulin | 1 USP = 0.0347 mg of human insulin |
| Glargine | 1U = 0.0364 mg of insulin glargine | 1 USP = 0.0364 mg of insulin glargine |
| Porcine | 1IU = 0.0345 mg of porcine insulin | 1 USP = 0.0345 mg of porcine insulin |
| Bovine | 1IU = 0.0342 mg of bovine insulin | 1 USP = 0.0342 mg of bovine insulin |

Basal insulin which isoelectric point is comprised from 5.8 to 8.5 denotes an insulin insoluble at pH 7 and which the duration of action is comprised from 8 to 24 hours or more in standard diabetes models.

These basal insulins which isoelectric point is comprised from 5.8 to 8.5 are recombinant insulins which primary structure has been modified essentially by introducing basic amino acids such as Arginine or Lysine. They are described for example in the following patents, patent applications or publications WO 2003/053339, WO 2004/096854, U.S. Pat. Nos. 5,656,722 and 6,100,376 the content whereof is incorporated by way of reference.

In one embodiment, the basal insulin which isoelectric point is comprised from 5.8 to 8.5 is insulin glargine. Insulin glargine is marketed under the trade name Lantus® (100 U/ml) or Toujeo® (300 U/ml) by SANOFI.

In one embodiment, the basal insulin which isoelectric point is comprised from 5.8 to 8.5 is a biosimilar insulin glargine.

A biosimilar insulin glargine is currently being developed for market under the trade name Abasaglar® or Basaglar® by ELI LILLY.

In one embodiment, the compositions according to the invention comprise from 40 to 500 U/mL of basal insulin which isoelectric point is comprised from 5.8 to 8.5.

In one embodiment, the compositions according to the invention comprise 40 U/mL of basal insulin which isoelectric point is comprised from 5.8 to 8.5.

In one embodiment, the compositions according to the invention comprise 100 U/mL (or about 3.6 mg/mL) of basal insulin which isoelectric point is comprised from 5.8 to 8.5.

In one embodiment, the compositions according to the invention comprise 150 U/mL of basal insulin which isoelectric point is comprised from 5.8 to 8.5.

In one embodiment, the compositions according to the invention comprise 200 U/mL of basal insulin which isoelectric point is comprised from 5.8 to 8.5.

In one embodiment, the compositions according to the invention comprise 225 U/mL of basal insulin which isoelectric point is comprised from 5.8 to 8.5.

In one embodiment, the compositions according to the invention comprise 250 U/mL of basal insulin which isoelectric point is comprised from 5.8 to 8.5.

In one embodiment, the compositions according to the invention comprise 300 U/mL of basal insulin which isoelectric point is comprised from 5.8 to 8.5.

In one embodiment, the compositions according to the invention comprise 400 U/mL of basal insulin which isoelectric point is comprised from 5.8 to 8.5.

In one embodiment, the compositions according to the invention comprise 500 U/mL of basal insulin which isoelectric point is comprised from 5.8 to 8.5.

In one embodiment, the mass ratio between the basal insulin, which isoelectric point is comprised from 5.8 to 8.5, and the co-polyamino acid, or co-polyamino acid/basal insulin, is comprised from 0.2 to 8.

In one embodiment, the mass ratio is comprised from 0.2 to 6.

In one embodiment, the mass ratio is comprised from 0.2 to 5.

In one embodiment, the mass ratio is comprised from 0.2 to 4.

In one embodiment, the mass ratio is comprised from 0.2 to 3.

In one embodiment, the mass ratio is comprised from 0.2 to 2.

In one embodiment, the mass ratio is comprised from 0.2 to 1.

In one embodiment, the compositions according to the invention further comprise a prandial insulin. Prandial insulins are soluble at pH 7.

Prandial insulin denotes a so-called rapid-acting or "regular" insulin.

So-called rapid-acting prandial insulins are insulins required to meet the needs induced by the intake of proteins and carbohydrates during a meal, they must act in less than 30 minutes.

In one embodiment, the so-called "regular" prandial insulin is human insulin.

In one embodiment, the prandial insulin is a recombinant human insulin described in the European Pharmacopeia and the US Pharmacopeia.

Human insulin is for example marketed under the trade names Humulin® (ELI LILLY) and Novolin® (NOVO NORDISK).

So-called very rapid-acting (fast-acting) prandial insulins are insulins obtained by recombination and which primary structure has been modified to reduce their duration of action.

In one embodiment, the so-called very rapid-acting (fast-acting) insulins are chosen in the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

In one embodiment, the compositions according to the invention comprise in total from 60 to 800 U/mL of insulin with a combination of prandial insulin and basal insulin which isoelectric point is comprised from 5.8 to 8.5.

In one embodiment, the compositions according to the invention comprise in total from 100 to 500 U/mL of insulin with a combination of prandial insulin and basal insulin which isoelectric point is comprised from 5.8 to 8.5.

In one embodiment, the compositions according to the invention comprise in total 800 U/mL of insulin with a combination of prandial insulin and basal insulin which isoelectric point is comprised from 5.8 to 8.5.

In one embodiment, the compositions according to the invention comprise in total 700 U/mL of insulin with a combination of prandial insulin and basal insulin which isoelectric point is comprised from 5.8 to 8.5.

In one embodiment, the compositions according to the invention comprise in total 600 U/mL of insulin with a combination of prandial insulin and basal insulin which isoelectric point is comprised from 5.8 to 8.5.

In one embodiment, the compositions according to the invention comprise in total 500 U/mL of insulin with a combination of prandial insulin and basal insulin which isoelectric point is comprised from 5.8 to 8.5.

In one embodiment, the compositions according to the invention comprise in total 400 U/mL of insulin with a combination of prandial insulin and basal insulin which isoelectric point is comprised from 5.8 to 8.5.

In one embodiment, the compositions according to the invention comprise in total 300 U/mL of insulin with a combination of prandial insulin and basal insulin which isoelectric point is comprised from 5.8 to 8.5.

In one embodiment, the compositions according to the invention comprise in total 266 U/mL of insulin with a combination of prandial insulin and basal insulin which isoelectric point is comprised from 5.8 to 8.5.

In one embodiment, the compositions according to the invention comprise in total 200 U/mL of insulin with a combination of prandial insulin and basal insulin which isoelectric point is comprised from 5.8 to 8.5.

In one embodiment, the compositions according to the invention comprise in total 100 U/mL of insulin with a combination of prandial insulin and basal insulin which isoelectric point is comprised from 5.8 to 8.5.

The proportions between the basal insulin which isoelectric point is comprised from 5.8 to 8.5 and the prandial insulin are for example 25/75, 30/70, 40/60, 50/50, 60/40, 63/37, 70/30, 75/25, 80/20, 83/17, 90/10 in percentage for formulations as described above comprising from 60 to 800 U/mL. However, any other proportion may be embodied.

In one embodiment, the basal insulin which isoelectric point is comprised from 5.8 to 8.5 and the prandial insulin are present respectively in the following concentrations (in U/ml) 75/25, 150/50, 200/66 or 300/100.

In one embodiment, the basal insulin which isoelectric point is comprised from 5.8 to 8.5 and the prandial insulin are present respectively in the following concentrations (in U/ml) 75/25.

In one embodiment, the basal insulin which isoelectric point is comprised from 5.8 to 8.5 and the prandial insulin are present respectively in the following concentrations (in U/ml) 150/50.

In one embodiment, the compositions according to the invention further comprise a gastrointestinal hormone.

The term "gastrointestinal hormones" denotes the hormones chosen in the group consisting of GLP-1 RA (Glucagon like peptide-1 receptor agonist) and GIP (Glucose-dependent insulinotropic peptide), oxyntomodulin (a derivative of proglucagon), peptide YY, amylin, cholecystokinin, pancreatic polypeptide (PP), ghrelin and enterostatin, the analogs or derivatives thereof and/or the pharmaceutically acceptable salts thereof.

In one embodiment, the gastrointestinal hormonesare analogs or derivatives of GLP-1 RA chosen in the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), their analogs or derivatives or their pharmaceutically acceptable salts.

In one embodiment, the gastrointestinal hormone is pramlintide or Symlin®® (ASTRA-ZENECA).

In one embodiment, the gastrointestinal hormone is exenatide or Byetta®, its analogs or derivatives and its pharmaceutically acceptable saltsits analogs or derivatives and its pharmaceutically acceptable salts.

In one embodiment, the gastrointestinal hormone is liraglutide or Victoza®, its analogs or derivatives and its pharmaceutically acceptable saltsits analogs or derivatives and its pharmaceutically acceptable salts.

In one embodiment, the gastrointestinal hormone is lixisenatide or Lyxumia®, its analogs or derivatives and its pharmaceutically acceptable saltsits analogs or derivatives and its pharmaceutically acceptable salts.

In one embodiment, the gastrointestinal hormone is albiglutide or Tanzeum®, its analogs or derivatives and its pharmaceutically acceptable saltsits analogs or derivatives and its pharmaceutically acceptable salts.

In one embodiment, the gastrointestinal hormone is dulaglutide or Trulicity®, its analogs or derivatives and its pharmaceutically acceptable saltsits analogs or derivatives and its pharmaceutically acceptable salts.

In one embodiment, the gastrointestinal hormone is pramlintide or Symlin®, its analogs or derivatives and its pharmaceutically acceptable saltsits analogs or derivatives and its pharmaceutically acceptable salts.

The term "analog" denotes, when used with reference to a peptide or a protein, a peptide or a protein, which one or a plurality of its constituent amino acid residues have been substituted by other amino acid residues and/or which one or a plurality of its constituent amino acid residues have been removed and/or which one or a plurality of its constituent amino acid residues have been added. The percentage of homology allowed for the present definition of an analog is 50%.

The term "derivative" denotes, when used with reference to a peptide or a protein, a peptide or a protein or an analog chemically modified by a substituent which is not present in the reference peptide or protein or analog, i.e. a peptide or a protein which has been modified by creating covalent bonds, to introduce substituents.

In one embodiment, the substituent is chosen in the group consisting of fatty chains.

In one embodiment, the concentration of gastrointestinal hormone is within a range from 0.01 to 100 mg/mL.

In one embodiment, the concentration of exenatide, its analogs or derivatives and its pharmaceutically acceptable salts is within a range from 0.04 to 0.5 mg/mL.

In one embodiment, the concentration of liraglutide, its analogs or derivatives and its pharmaceutically acceptable salts is within a range from 1 to 10 mg/mL.

In one embodiment, the concentration of lixisenatide, its analogs or derivatives and its pharmaceutically acceptable salts is within a range from 0.01 to 1 mg/mL.

In one embodiment, the concentration of albiglutide, its analogs or derivatives and its pharmaceutically acceptable salts salts is comprised from 5 to 100 mg/mL.

In one embodiment, the concentration of dulaglutide, its analogs or derivatives and its pharmaceutically acceptable salts is comprised from 0.1 to 10 mg/mL.

In one embodiment, the concentration of pramlintide, its analogs or derivatives and its pharmaceutically acceptable salts is comprised from 0.1 to 5 mg/mL.

In one embodiment, the compositions according to the invention are obtained by mixing commercial solutions of basal insulin which isoelectric point is comprised from 5.8 to 8.5 and commercial solutions of GLP-1 RA, analog or derivative of GLP-1 RA in volume ratios within a range from 10/90 to 90/10.

In one embodiment, the composition according to the invention comprises a daily dose of basal insulin and a daily dose of gastrointestinal hormone.

In one embodiment, the compositions according to the invention comprise from 40 U/mL from 500 U/mL of basal insulin which isoelectric point is comprised from 5.8 to 8.5 and, from 0.05 from 0.5 mg/mL of exanatide.

In one embodiment, the compositions according to the invention comprise from 40 U/mL to 500 U/mL of basal insulin which isoelectric point is comprised from 5.8 to 8.5 and, from 1 to 10 mg/mL of liraglutide.

In one embodiment, the compositions according to the invention comprise from 40 U/ml to 500 U/mL of basal insulin which isoelectric point is comprised from 5.8 to 8.5 and, from 0.01 to 1 mg/mL of lixisenatide.

In one embodiment, the compositions according to the invention comprise from 40 U/mL to 500 U/mL of basal insulin which isoelectric point is comprised from 5.8 to 8.5 and, from 5 to 100 mg/mL of albiglutide.

In one embodiment, the compositions according to the invention comprise from 40 U/mL to 500 U/mL of basal insulin which isoelectric point is comprised from 5.8 to 8.5 and, from 0.1 to 10 mg/mL of dulaglutide.

In one embodiment, the compositions according to the invention comprise 500 U/mL of basal insulin which isoelectric point is comprised from 5.8 to 8.5 and, from 0.04 to 0.5 mg/mL of exenatide.

In one embodiment, the compositions according to the invention comprise 500 U/mL of basal insulin which isoelectric point is comprised from 5.8 to 8.5 and, from 1 to 10 mg/mL of liraglutide.

In one embodiment, the compositions according to the invention comprise 500 U/mL of basal insulin which isoelectric point is comprised from 5.8 to 8.5 and, from 0.01 to 1 mg/mL of lixisenatide.

In one embodiment, the compositions according to the invention comprise 500 U/mL of basal insulin which isoelectric point is comprised from 5.8 to 8.5 and, from 5 to 100 mg/mL of albiglutide.

In one embodiment, the compositions according to the invention comprise 500 U/mL of basal insulin which isoelectric point is comprised from 5.8 to 8.5 and, from 0.1 to 10 mg/mL of dulaglutide.

In one embodiment, the compositions according to the invention comprise 400 U/mL of basal insulin which isoelectric point is comprised from 5.8 to 8.5 and, from 0.04 to 0.5 mg/mL of exenatide.

In one embodiment, the compositions according to the invention comprise 400 U/mL of basal insulin which isoelectric point is comprised from 5.8 to 8.5 and, from 1 to 10 mg/mL of liraglutide.

In one embodiment, the compositions according to the invention comprise 400 U/mL of basal insulin which isoelectric point is comprised from 5.8 to 8.5 and, from 0.01 to 1 mg/mL of lixisenatide.

In one embodiment, the compositions according to the invention comprise 400 U/mL of basal insulin which isoelectric point is comprised from 5.8 to 8.5 and, from 5 to 100 mg/mL of albiglutide.

In one embodiment, the compositions according to the invention comprise 400 U/mL of basal insulin which isoelectric point is comprised from 5.8 to 8.5 and, from 0.1 to 10 mg/mL of dulaglutide.

In one embodiment, the compositions according to the invention comprise 300 U/mL of basal insulin which isoelectric point is comprised from 5.8 to 8.5 and, from 0.04 to 0.5 mg/mL of exenatide.

In one embodiment, the compositions according to the invention comprise 300 U/mL of basal insulin which isoelectric point is comprised from 5.8 to 8.5 and, from 1 to 10 mg/mL of liraglutide.

In one embodiment, the compositions according to the invention comprise 300 U/mL of basal insulin which isoelectric point is comprised from 5.8 to 8.5 and, from 0.01 to 1 mg/mL of lixisenatide.

In one embodiment, the compositions according to the invention comprise 300 U/mL of basal insulin which isoelectric point is comprised from 5.8 to 8.5 and, from 5 to 100 mg/mL of albiglutide.

In one embodiment, the compositions according to the invention comprise 300 U/mL of basal insulin which isoelectric point is comprised from 5.8 to 8.5 and, from 0.1 to 10 mg/mL of dulaglutide.

In one embodiment, the compositions according to the invention comprise 225 U/mL of basal insulin which isoelectric point is comprised from 5.8 to 8.5 and, from 0.04 to 0.5 mg/mL of exenatide.

In one embodiment, the compositions according to the invention comprise 225 U/mL of basal insulin which isoelectric point is comprised from 5.8 to 8.5 and, from 1 to 10 mg/mL of liraglutide.

In one embodiment, the compositions according to the invention comprise 225 U/mL of basal insulin which isoelectric point is comprised from 5.8 to 8.5 and, from 0.01 to 1 mg/mL of lixisenatide.

In one embodiment, the compositions according to the invention comprise 225 U/mL of basal insulin which isoelectric point is comprised from 5.8 to 8.5 and, from 5 to 100 mg/mL of albiglutide.

In one embodiment, the compositions according to the invention comprise 225 U/mL of basal insulin which isoelectric point is comprised from 5.8 to 8.5 and, from 0.1 to 10 mg/mL of dulaglutide.

In one embodiment, the compositions according to the invention comprise 200 U/mL of basal insulin which isoelectric point is comprised from 5.8 to 8.5 and, from 0.04 to 0.5 mg/mL of exenatide.

In one embodiment, the compositions according to the invention comprise 200 U/mL of basal insulin which isoelectric point is comprised from 5.8 to 8.5 and, from 1 to 10 mg/mL of liraglutide.

In one embodiment, the compositions according to the invention comprise 200 U/mL of basal insulin which isoelectric point is comprised from 5.8 to 8.5 and, from 0.01 to 1 mg/mL of lixisenatide.

In one embodiment, the compositions according to the invention comprise 200 U/mL of basal insulin which isoelectric point is comprised from 5.8 to 8.5 and, from 5 to 100 mg/mL of albiglutide.

In one embodiment, the compositions according to the invention comprise 200 U/mL of basal insulin which isoelectric point is comprised from 5.8 to 8.5 and, from 0.1 to 10 mg/mL of dulaglutide.

In one embodiment, the compositions according to the invention comprise 100 U/mL (or about 3.6 mg/mL) of basal insulin which isoelectric point is comprised from 5.8 to 8.5 and, from 0.04 to 0.5 mg/mL of exenatide.

In one embodiment, the compositions according to the invention comprise 100 U/mL (or about 3.6 mg/mL) of basal insulin which isoelectric point is comprised from 5.8 to 8.5 and, from 1 to 10 mg/mL of liraglutide.

In one embodiment, the compositions according to the invention comprise 100 U/mL (or about 3.6 mg/mL) of basal insulin which isoelectric point is comprised from 5.8 to 8.5 and, from 0.01 to 1 mg/mL of lixisenatide.

In one embodiment, the compositions according to the invention comprise 100 U/mL of basal insulin which isoelectric point is comprised from 5.8 to 8.5 and, from 5 to 100 mg/mL of albiglutide.

In one embodiment, the compositions according to the invention comprise 100 U/mL of basal insulin which isoelectric point is comprised from 5.8 to 8.5 and, from 0.1 to 10 mg/mL of dulaglutide.

In one embodiment, the compositions according to the invention comprise 40 U/mL of basal insulin which isoelectric point is comprised from 5.8 to 8.5 and, from 0.04 to 0.5 mg/mL of exenatide.

In one embodiment, the compositions according to the invention comprise 40 U/mL of basal insulin which isoelectric point is comprised from 5.8 to 8.5 and, from 1 to 10 mg/mL of liraglutide.

In one embodiment, the compositions according to the invention comprise 40 U/mL of basal insulin which isoelectric point is comprised from 5.8 to 8.5 and, from 0.01 to 1 mg/mL of lixisenatide.

In one embodiment, the compositions according to the invention comprise 40 U/mL of basal insulin which isoelectric point is comprised from 5.8 to 8.5 and, from 5 to 100 mg/mL of albiglutide.

In one embodiment, the compositions according to the invention comprise 40 U/mL of basal insulin which isoelectric point is comprised from 5.8 to 8.5 and, from 0.1 to 10 mg/mL of dulaglutide.

In one embodiment, the compositions according to the invention further comprise zinc salts at a concentration from 0 to 5000 µM.

In one embodiment, the compositions according to the invention further comprise zinc salts at a concentration from 0 to 4000 µM.

In one embodiment, the compositions according to the invention further comprise zinc salts at a concentration from 0 to 3000 µM.

In one embodiment, the compositions according to the invention further comprise zinc salts at a concentration from 0 to 2000 µM.

In one embodiment, the compositions according to the invention further comprise zinc salts at a concentration from 0 to 1000 µM.

In one embodiment, the compositions according to the invention further comprise zinc salts at a concentration from 50 to 600 µM.

In one embodiment, the compositions according to the invention further comprise zinc salts at a concentration from 100 to 500 µM.

In one embodiment, the compositions according to the invention further comprise zinc salts at a concentration from 200 to 500 µM.

In one embodiment, the compositions according to the invention further comprise buffers.

In one embodiment, the compositions according to the invention comprise buffers at concentrations from 0 to 100 mM.

In one embodiment, the compositions according to the invention comprise buffers at concentrations from 15 to 50 mM.

In one embodiment, the compositions according to the invention comprise a buffer chosen in the group consisting of a phosphate buffer, Tris (trishydroxymethylaminomethane) and sodium citrate.

In one embodiment, the buffer is sodium phosphate.

The invention also relates to compositions further comprising ionic species, said ionic species being suitable for improving the physicochemical stability of the compositions.

The invention also relates to the use of ionic species chosen in the group of anions, cations and/or zwitterions for improving the physicochemical stability of the compositions.

In one embodiment, the ionic species comprise less than 10 carbon atoms.

Said ionic species are chosen in the group of anions, cations and/or zwitterions. The term zwitterion denotes a species bearing at least one positive charge and at least one negative charge on two non-adjacent atoms.

Said ionic species are used alone or in a mixture and preferably in a mixture.

In one embodiment, the anions are chosen among organic anions.

In one embodiment, the organic anions comprise less than 10 carbon atoms.

In one embodiment, the organic anions are chosen in the group consisting of acetate, citrate and succinate In one embodiment, the anions are chosen among inorganic anions.

In one embodiment, the inorganic anions are chosen in the group consisting of sulfates, phosphates and halides, particularly chlorides.

In one embodiment, the cations are chosen among organic cations.

In one embodiment, the organic cations comprise less than 10 carbon atoms.

In one embodiment, the organic cations are chosen in the group consisting of ammoniums, for example 2-Amino-2-(hydroxymethyl)propane-1,3-diol where the amine is in ammonium form.

In one embodiment, the cations are chosen among inorganic cations.

In one embodiment, the inorganic cations are chosen in the group consisting of zinc, in particular $Zn^{2+}$ and alkali metals, in particular $Na^+$ and $K^+$, In one embodiment, the zwitterions are chosen among organic zwitterions.

In one embodiment, the organic zwitterions are chosen among amino acids.

In one embodiment, the amino acids are chosen among aliphatic amino acids in the group consisting of glycine, alanine, valine, isoleucine and leucine.

In one embodiment, the amino acids are chosen among cyclic amino acids in the group consisting of proline.

In one embodiment, the amino acids are chosen among hydroxylated amino acids in the group consisting of cysteine, serine, threonine, and methionine.

In one embodiment, the amino acids are chosen among aromatic amino acids in the group consisting of phenylalanine, tyrosine and tryptophan.

In one embodiment, the amino acids are chosen among amino acids wherein the carboxyl function of the side chain is amidified in the group consisting of asparagine and glutamine.

In one embodiment, the organic zwitterions are chosen in the group consisting of amino acids having a non-charged side chain.

In one embodiment, the organic zwitterions are chosen in the group consisting of amino diacids or acidic amino acids.

In one embodiment, the amino diacids are chosen in the group consisting of glutamic acid and aspartic acid, optionally in salt form.

In one embodiment, the organic zwitterions are chosen in the group consisting of basic or so-called "cationic" amino acids.

In one embodiment, the so-called "cationic" amino acids are chosen among arginine, histidine and lysine, in particular arginine and lysine.

Most particularly, the zwitterions comprise as many negative charges as positive charges and therefore a nil overall charge at the isoelectric point and/or at a pH from 6 to 8.

Said ionic species are introduced into the compositions in salt form. The introduction thereof may be made in solid form prior solubilization in the compositions, or in solution form, in particular concentrated solution.

For example, the inorganic cations are added in the form of salts chosen among sodium chloride, zinc chloride, sodium phosphate, sodium sulfate, etc.

For example, the organic cations are added in the form of salts chosen among sodium or potassium citrate, sodium acetate.

For example, the amino acids are added in the form of salts chosen among arginine hydrochloride, histidine hydrochloride or in the non-salified form such as for example histidine, arginine.

In one embodiment, the total molar concentration of ionic species in the composition is greater than or equal to 10 mM.

In one embodiment, the total molar concentration of ionic species in the composition is greater than or equal to 20 mM.

In one embodiment, the total molar concentration of ionic species in the composition is greater than or equal to 30 mM.

In one embodiment, the total molar concentration of ionic species in the composition is greater than or equal to 50 mM.

In one embodiment, the total molar concentration of ionic species in the composition is greater than or equal to 75 mM.

In one embodiment, the total molar concentration of ionic species in the composition is greater than or equal to 100 mM.

In one embodiment, the total molar concentration of ionic species in the composition is greater than or equal to 200 mM.

In one embodiment, the total molar concentration of ionic species in the composition is greater than or equal to 300 mM.

In one embodiment, the total molar concentration of ionic species in the composition is greater than or equal to 500 mM.

In one embodiment, the total molar concentration of ionic species in the composition is greater than or equal to 600 mM.

In one embodiment, the total molar concentration of ionic species in the composition is greater than or equal to 700 mM.

In one embodiment, the total molar concentration of ionic species in the composition is greater than or equal to 800 mM.

In one embodiment, the total molar concentration of ionic species in the composition is greater than or equal to 900 mM.

In one embodiment, the total molar concentration of ionic species in the composition is less than or equal to 1000 mM.

In one embodiment, the total molar concentration of ionic species in the composition is less than or equal to 1500 mM.

In one embodiment, the total molar concentration of ionic species in the composition is less than or equal to 1200 mM.

In one embodiment, the total molar concentration of ionic species in the composition is less than or equal to 1000 mM.

In one embodiment, the total molar concentration of ionic species in the composition is less than or equal to 900 mM.

In one embodiment, the total molar concentration of ionic species in the composition is less than or equal to 800 mM.

In one embodiment, the total molar concentration of ionic species in the composition is less than or equal to 700 mM.

In one embodiment, the total molar concentration of ionic species in the composition is less than or equal to 600 mM.

In one embodiment, the total molar concentration of ionic species in the composition is less than or equal to 500 mM.

In one embodiment, the total molar concentration of ionic species in the composition is less than or equal to 400 mM.

In one embodiment, the total molar concentration of ionic species in the composition is less than or equal to 300 mM.

In one embodiment, the total molar concentration of ionic species in the composition is less than or equal to 200 mM.

In one embodiment, the total molar concentration of ionic species in the composition is less than or equal to 100 mM.

In one embodiment, the total molar concentration of ionic species in the composition is comprised from 10 to 1000 mM.

In one embodiment, the total molar concentration of ionic species in the composition is comprised from 20 to 1000 mM.

In one embodiment, the total molar concentration of ionic species in the composition is comprised from 30 to 1000 mM.

In one embodiment, the total molar concentration of ionic species in the composition is comprised from 50 to 1000 mM.

In one embodiment, the total molar concentration of ionic species in the composition is comprised from 75 to 1000 mM.

In one embodiment, the total molar concentration of ionic species in the composition is comprised from 100 to 1000 mM.

In one embodiment, the total molar concentration of ionic species in the composition is comprised from 200 to 1000 mM.

In one embodiment, the total molar concentration of ionic species in the composition is comprised from 300 to 1000 mM.

In one embodiment, the total molar concentration of ionic species in the composition is comprised from 400 to 1000 mM.

In one embodiment, the total molar concentration of ionic species in the composition is comprised from 500 to 1000 mM.

In one embodiment, the total molar concentration of ionic species in the composition is comprised from 600 to 1000 mM.

In one embodiment, the total molar concentration of ionic species in the composition is comprised from 10 to 900 mM.

In one embodiment, the total molar concentration of ionic species in the composition is comprised from 20 to 900 mM.

In one embodiment, the total molar concentration of ionic species in the composition is comprised from 30 to 900 mM.

In one embodiment, the total molar concentration of ionic species in the composition is comprised from 50 to 900 mM.

In one embodiment, the total molar concentration of ionic species in the composition is comprised from 75 to 900 mM.

In one embodiment, the total molar concentration of ionic species in the composition is comprised from 100 to 900 mM.

In one embodiment, the total molar concentration of ionic species in the composition is comprised from 200 to 900 mM.

In one embodiment, the total molar concentration of ionic species in the composition is comprised from 300 to 900 mM.

In one embodiment, the total molar concentration of ionic species in the composition is comprised from 400 to 900 mM.

In one embodiment, the total molar concentration of ionic species in the composition is comprised from 500 to 900 mM.

In one embodiment, the total molar concentration of ionic species in the composition is comprised from 600 to 900 mM.

In one embodiment, the total molar concentration of ionic species in the composition is comprised from 10 to 900 mM.

In one embodiment, the total molar concentration of ionic species in the composition is comprised from 20 to 800 mM.

In one embodiment, the total molar concentration of ionic species in the composition is comprised from 30 to 800 mM.

In one embodiment, the total molar concentration of ionic species in the composition is comprised from 50 to 800 mM.

In one embodiment, the total molar concentration of ionic species in the composition is comprised from 75 to 800 mM.

In one embodiment, the total molar concentration of ionic species in the composition is comprised from 100 to 800 mM.

In one embodiment, the total molar concentration of ionic species in the composition is comprised from 200 to 800 mM.

In one embodiment, the total molar concentration of ionic species in the composition is comprised from 300 to 800 mM.

In one embodiment, the total molar concentration of ionic species in the composition is comprised from 400 to 800 mM.

In one embodiment, the total molar concentration of ionic species in the composition is comprised from 500 to 800 mM.

In one embodiment, the total molar concentration of ionic species in the composition is comprised from 600 to 800 mM.

In one embodiment, the total molar concentration of ionic species in the composition is comprised from 10 to 700 mM.

In one embodiment, the total molar concentration of ionic species in the composition is comprised from 20 to 700 mM.

In one embodiment, the total molar concentration of ionic species in the composition is comprised from 30 to 700 mM.

In one embodiment, the total molar concentration of ionic species in the composition is comprised from 50 to 700 mM.

In one embodiment, the total molar concentration of ionic species in the composition is comprised from 75 to 700 mM.

In one embodiment, the total molar concentration of ionic species in the composition is comprised from 100 to 700 mM.

In one embodiment, the total molar concentration of ionic species in the composition is comprised from 200 to 700 mM.

In one embodiment, the total molar concentration of ionic species in the composition is comprised from 300 to 700 mM.

In one embodiment, the total molar concentration of ionic species in the composition is comprised from 400 to 700 mM.

In one embodiment, the total molar concentration of ionic species in the composition is comprised from 500 to 700 mM.

In one embodiment, the total molar concentration of ionic species in the composition is comprised from 600 to 700 mM.

In one embodiment, the total molar concentration of ionic species in the composition is comprised from 10 to 600 mM.

In one embodiment, the total molar concentration of ionic species in the composition is comprised from 20 to 600 mM.

In one embodiment, the total molar concentration of ionic species in the composition is comprised from 30 to 600 mM.

In one embodiment, the total molar concentration of ionic species in the composition is comprised from 50 to 600 mM.

In one embodiment, the total molar concentration of ionic species in the composition is comprised from 75 to 600 mM.

In one embodiment, the total molar concentration of ionic species in the composition is comprised from 100 to 600 mM.

In one embodiment, the total molar concentration of ionic species in the composition is comprised from 200 to 600 mM.

In one embodiment, the total molar concentration of ionic species in the composition is comprised from 300 to 600 mM.

In one embodiment, the total molar concentration of ionic species in the composition is comprised from 400 to 600 mM.

In one embodiment, the total molar concentration of ionic species in the composition is comprised from 500 to 600 mM.

In one embodiment, the total molar concentration of ionic species in the composition is comprised from 10 to 500 mM.

In one embodiment, the total molar concentration of ionic species in the composition is comprised from 20 to 500 mM.

In one embodiment, the total molar concentration of ionic species in the composition is comprised from 30 to 500 mM.

In one embodiment, the total molar concentration of ionic species in the composition is comprised from 50 to 500 mM.

In one embodiment, the total molar concentration of ionic species in the composition is comprised from 75 to 500 mM.

In one embodiment, the total molar concentration of ionic species in the composition is comprised from 100 to 500 mM.

In one embodiment, the total molar concentration of ionic species in the composition is comprised from 200 to 500 mM.

In one embodiment, the total molar concentration of ionic species in the composition is comprised from 300 to 500 mM.

In one embodiment, the total molar concentration of ionic species in the composition is comprised from 400 to 500 mM.

In one embodiment, the total molar concentration of ionic species in the composition is comprised from 10 to 400 mM.

In one embodiment, the total molar concentration of ionic species in the composition is comprised from 20 to 400 mM.

In one embodiment, the total molar concentration of ionic species in the composition is comprised from 30 to 400 mM.

In one embodiment, the total molar concentration of ionic species in the composition is comprised from 50 to 400 mM.

In one embodiment, the total molar concentration of ionic species in the composition is comprised from 75 to 400 mM.

In one embodiment, the total molar concentration of ionic species in the composition is comprised from 100 to 400 mM.

In one embodiment, the total molar concentration of ionic species in the composition is comprised from 200 to 400 mM.

In one embodiment, the total molar concentration of ionic species in the composition is comprised from 300 to 400 mM.

In one embodiment, the total molar concentration of ionic species in the composition is comprised from 10 to 300 mM.

In one embodiment, the total molar concentration of ionic species in the composition is comprised from 20 to 300 mM.

In one embodiment, the total molar concentration of ionic species in the composition is comprised from 30 to 300 mM.

In one embodiment, the total molar concentration of ionic species in the composition is comprised from 50 to 300 mM.

In one embodiment, the total molar concentration of ionic species in the composition is comprised from 75 to 300 mM.

In one embodiment, the total molar concentration of ionic species in the composition is comprised from 100 to 300 mM.

In one embodiment, the total molar concentration of ionic species in the composition is comprised from 200 to 300 mM.

In one embodiment, the total molar concentration of ionic species in the composition is comprised from 10 to 200 mM.

In one embodiment, the total molar concentration of ionic species in the composition is comprised from 20 to 200 mM.

In one embodiment, the total molar concentration of ionic species in the composition is comprised from 30 to 200 mM.

In one embodiment, the total molar concentration of ionic species in the composition is comprised from 50 to 200 mM.

In one embodiment, the total molar concentration of ionic species in the composition is comprised from 75 to 200 mM.

In one embodiment, the total molar concentration of ionic species in the composition is comprised from 100 to 200 mM.

In one embodiment, the total molar concentration of ionic species in the composition is comprised from 10 to 100 mM.

In one embodiment, the total molar concentration of ionic species in the composition is comprised from 20 to 100 mM.

In one embodiment, the total molar concentration of ionic species in the composition is comprised from 30 to 100 mM.

In one embodiment, the total molar concentration of ionic species in the composition is comprised from 50 to 100 mM.

In one embodiment, the total molar concentration of ionic species in the composition is comprised from 75 to 100 mM.

In one embodiment, the total molar concentration of ionic species in the composition is comprised from 10 to 75 mM.

In one embodiment, the total molar concentration of ionic species in the composition is comprised from 20 to 75 mM.

In one embodiment, the total molar concentration of ionic species in the composition is comprised from 30 to 75 mM.

In one embodiment, the total molar concentration of ionic species in the composition is comprised from 50 to 75 mM.

In one embodiment, the total molar concentration of ionic species in the composition is comprised from 10 to 50 mM.

In one embodiment, the total molar concentration of ionic species in the composition is comprised from 20 to 50 mM.

In one embodiment, the total molar concentration of ionic species in the composition is comprised from 30 to 50 mM.

In one embodiment, said ionic species are present at a concentration ranging from 5 to 400 mM.

In one embodiment, said ionic species are present at a concentration ranging from 5 to 300 mM.

In one embodiment, said ionic species are present at a concentration ranging from 5 to 200 mM.

In one embodiment, said ionic species are present at a concentration ranging from 5 to 100 mM.

In one embodiment, said ionic species are present at a concentration ranging from 5 to 75 mM.

In one embodiment, said ionic species are present at a concentration ranging from 5 to 50 mM.

In one embodiment, said ionic species are present at a concentration ranging from 5 to 25 mM.

In one embodiment, said ionic species are present at a concentration ranging from 5 to 20 mM.

In one embodiment, said ionic species are present at a concentration ranging from 5 to 10 mM.

In one embodiment, said ionic species are present at a concentration ranging from 10 to 400 mM.

In one embodiment, said ionic species are present at a concentration ranging from 10 to 300 mM.

In one embodiment, said ionic species are present at a concentration ranging from 10 to 200 mM.

In one embodiment, said ionic species are present at a concentration ranging from 10 to 100 mM.

In one embodiment, said ionic species are present at a concentration ranging from 10 to 75 mM.

In one embodiment, said ionic species are present at a concentration ranging from 10 to 50 mM.

In one embodiment, said ionic species are present at a concentration ranging from 10 to 25 mM.

In one embodiment, said ionic species are present at a concentration ranging from 10 to 20 mM.

In one embodiment, said ionic species are present at a concentration ranging from 20 to 300 mM.

In one embodiment, said ionic species are present at a concentration ranging from 20 to 200 mM.

In one embodiment, said ionic species are present at a concentration ranging from 20 to 100 mM.

In one embodiment, said ionic species are present at a concentration ranging from 20 to 75 mM.

In one embodiment, said ionic species are present at a concentration ranging from 20 to 50 mM.

In one embodiment, said ionic species are present at a concentration ranging from 20 to 25 mM.

In one embodiment, said ionic species are present at a concentration ranging from 50 to 300 mM.

In one embodiment, said ionic species are present at a concentration ranging from 50 to 200 mM.

In one embodiment, said ionic species are present at a concentration ranging from 50 to 100 mM.

In one embodiment, said ionic species are present at a concentration ranging from 50 to 75 mM.

In the case of inorganic cations and in particular of $Zn^{2+}$, the molar concentration thereof in the composition may be from 0.25 to 20 mM, in particular from 0.25 to 10 mM or from 0.25 to 5 mM.

In one embodiment, the composition comprises zinc.

In one embodiment, the composition comprises from 0.2 to 2 mM of zinc.

In one embodiment, the composition comprises NaCl.

In one embodiment, NaCl is present at a concentration ranging from 2 to 25 mM

In one embodiment, NaCl is present at a concentration ranging from 2.5 to 20 mM

In one embodiment, NaCl is present at a concentration ranging from 4 to 15 mM

In one embodiment, NaCl is present at a concentration ranging from 5 to 10 mM

In one embodiment, the buffer is Tris (trishydroxymethylaminomethane).

In one embodiment, the buffer is sodium citrate.

In one embodiment, the compositions according to the invention further comprise preservatives.

In one embodiment, the preservatives are chosen in the group consisting of m-cresol and phenol, alone or in a mixture.

In one embodiment, the concentration of the preservatives is comprised from 10 to 50 mM.

In one embodiment, the concentration of the preservatives is comprised from 10 to 40 mM.

In one embodiment, the compositions according to the invention further comprise a surfactant.

In one embodiment, the surfactant is chosen in the group consisting of propylene glycol and polysorbate.

The compositions according to the invention may further comprise additives such as tonicity agents.

In one embodiment, the tonicity agents are chosen in the group consisting of glycerin, sodium chloride, mannitol and glycine.

The compositions according to the invention may further comprise any excipients complying with the pharmacopeias and compatible with insulins used at customary concentrations.

The invention also relates to a pharmaceutical formulation according to the invention, characterized in that it is obtained by drying and/or freeze-drying.

In the case of local and systemic releases, the modes of administration envisaged are by the intravenous, subcutaneous, intradermal or intramuscular route.

The transdermal, oral, nasal, vaginal, ocular, buccal, pulmonary administration routes are also envisaged.

The invention also relates to single-dose formulations at pH from 6.0 to 8.0 comprising a basal insulin which isoelectric point is comprised from 5.8 to 8.5.

The invention also relates to single-dose formulations at pH from 6.0 to 8.0 comprising a basal insulin which isoelectric point is comprised from 5.8 to 8.5 and a prandial insulin.

The invention also relates to single-dose formulations at pH from 6.0 to 8.0 comprising a basal insulin which isoelectric point is comprised from 5.8 to 8.5 and a gastrointestinal hormone, as defined above.

The invention also relates to single-dose formulations at pH from 6.0 to 8.0 comprising a basal insulin which isoelectric point is comprised from 5.8 to 8.5, a prandial insulin and a gastrointestinal hormone, as defined above.

The invention also relates to single-dose formulations at pH from 6.6 to 7.8 comprising a basal insulin which isoelectric point is comprised from 5.8 to 8.5.

The invention also relates to single-dose formulations at pH from 6.6 to 7.8 comprising a basal insulin which isoelectric point is comprised from 5.8 to 8.5 and a prandial insulin.

The invention also relates to single-dose formulations at pH from 6.6 to 7.8 comprising a basal insulin which isoelectric point is comprised from 5.8 to 8.5 and a gastrointestinal hormone, as defined above.

The invention also relates to single-dose formulations at pH from 6.6 to 7.8 comprising a basal insulin which isoelectric point is comprised from 5.8 to 8.5, a prandial insulin and a gastrointestinal hormone, as defined above.

The invention also relates to single-dose formulations at pH from 6.6 to 7.6 comprising a basal insulin which isoelectric point is comprised from 5.8 to 8.5.

The invention also relates to single-dose formulations at pH from 6.6 to 7.6 comprising a basal insulin which isoelectric point is comprised from 5.8 to 8.5 and a prandial insulin.

The invention also relates to single-dose formulations at pH from 6.6 to 7.6 comprising a basal insulin which isoelectric point is comprised from 5.8 to 8.5 and a gastrointestinal hormone, as defined above.

The invention also relates to single-dose formulations at pH from 6.6 to 7.6 comprising a basal insulin which isoelectric point is comprised from 5.8 to 8.5, a prandial insulin and a gastrointestinal hormone, as defined above.

In one embodiment, the single-dose formulations further comprise a co-polyamino acid as defined above.

In one embodiment, the formulations are in the form of an injectable solution.

"In one embodiment, the composition according to the invention is characterized in that it is administered once per day.

In one embodiment, the composition according to the invention is characterized in that it is administered at least 2 times per day.

In one embodiment, the composition according to the invention is characterized in that it is administered 2 times per day.

In one embodiment, the composition according to the invention is characterized in that it further comprises a prandial insulin.

In one embodiment, the composition according to the invention further comprising at least one prandial insulin is characterized in that it is administered at least once per day.

In one embodiment, the composition according to the invention further comprising at least one prandial insulin is characterized in that it is administered at least 2 times per day.

In one embodiment, the composition according to the invention further comprising at least one prandial insulin is characterized in that it is administered 2 times per day.

In one embodiment, the composition according to the invention is characterized in that it further comprises a gastrointestinal hormone.

In one embodiment, the composition according to the invention further comprising at least one gastrointestinal hormone is characterized in that it is administered at least once per day.

In one embodiment, the composition according to the invention further comprising at least one gastrointestinal hormone is characterized in that it is administered at least 2 times per day.

In one embodiment, the composition according to the invention further comprising at least one gastrointestinal hormone is characterized in that it is administered 2 times per day.

In one embodiment, the composition according to the invention is characterized in that the gastrointestinal hormone is a GLP-1 RA.

In one embodiment, the composition according to the invention further comprising at one GLP-1 RA is characterized in that it is administered once per day.

In one embodiment, the composition according to the invention further comprising at least one GLP-1 RA is characterized in that it is administered at least 2 times per day.

In one embodiment, the composition according to the invention further comprising at least one GLP-1 RA is characterized in that it is administered 2 times per day.".

The solubilization at pH from 6.0 to 8.0 of the basal insulins which isoelectric point is comprised from 5.8 to 8.5, by the co-polyamino acids bearing carboxylate charges and at least one hydrophobic radical according to the invention, may be observed and controlled simply, with the naked eye, by means of a change of appearance of the solution.

The solubilization at pH from 6.6 to 7.8 of the basal insulins which isoelectric point is comprised from 5.8 to 8.5, by the co-polyamino acids bearing carboxylate charges and at least one hydrophobic radical according to the invention, may be observed and controlled simply, with the naked eye, by means of a change of appearance of the solution.

Moreover and equally importantly, the applicant was able to confirm that a basal insulin which isoelectric point is comprised from 5.8 to 8.5, solubilized at pH from 6.0 to 8.0 in the presence of a co-polyamino acid bearing carboxylate charges and at least one hydrophobic radical according to the invention retains its slow-acting insulin action whether alone or in combination with a prandial insulin or a gastrointestinal hormone.

The applicant also confirmed that a prandial insulin mixed at pH from 6.0 to 8.0 in the presence of a co-polyamino acid bearing carboxylate charges and at least one hydrophobic radical according to the invention and of a basal insulin which isoelectric point is comprised from 5.8 to 8.5, retains its rapid-acting insulin action.

The preparation of a composition according to the invention offers the advantage of being suitable for being carried out by merely mixing an aqueous solution of basal insulin which isoelectric point is comprised from 5.8 to 8.5, and a co-polyamino acid bearing carboxylate charges and at least one hydrophobic radical according to the invention, in aqueous solution or in freeze-dried form. If required, the pH of the preparation is adjusted to pH from 6 to 8.

The preparation of a composition according to the invention offers the advantage of being suitable for being carried out by merely mixing an aqueous solution of basal insulin which isoelectric point is comprised from 5.8 to 8.5, a solution of prandial insulin, and a co-polyamino acid bearing carboxylate charges and at least one hydrophobic radical according to the invention, in aqueous solution or in freeze-dried form. If required, the pH of the preparation is adjusted to pH from 6 to 8.

The preparation of a composition according to the invention offers the advantage of being suitable for being carried out by merely mixing an aqueous solution of basal insulin which isoelectric point is comprised from 5.8 to 8.5, a solution of GLP-1 RA, an analog or a derivative of GLP-1 RA, and a co-polyamino acid bearing carboxylate charges and at least one hydrophobic radical according to the invention, in aqueous solution or in freeze-dried form. If required, the pH of the preparation is adjusted to pH from 6 to 8.

The preparation of a composition according to the invention offers the advantage of being suitable for being carried out by merely mixing an aqueous solution of basal insulin which isoelectric point is comprised from 5.8 to 8.5, a solution of prandial insulin, a solution of GLP-1 RA, an analog or a derivative of GLP-1 RA, and a co-polyamino acid bearing carboxylate charges and at least one hydrophobic radical according to the invention, in aqueous solution or in freeze-dried form. If required, the pH of the preparation is adjusted to pH from 6 to 8.

In one embodiment, the mixture of basal insulin and co-polyamino acid is concentrated by ultrafiltration prior to mixing with the prandial insulin in aqueous solution or in freeze-dried form.

If required, the composition of the mixture is adjusted with excipients such as glycerin, m-cresol, zinc chloride, and polysorbate (Tween®) by adding concentrated solutions of these excipients in the mixture. If required, the pH of the preparation is adjusted to pH from 6 to 8.

The examples hereinafter illustrate, in a non-limiting manner, the invention.

EXAMPLES

Part A—Synthesis of Hydrophobic Intermediate Compounds Hyd for Obtaining the Radicals -Hy.

| # | HYDROPHOBIC INTERMEDIATE COMPOUNDS |
|---|---|
| A1 | 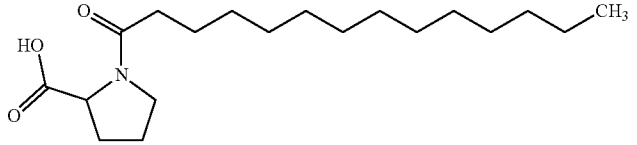 [SMILES: CCCCCCCCCCCCCC(=O)N1CCCC1C(=O)O] |
| A2 | 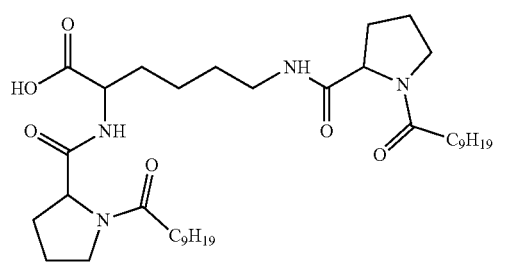 |

-continued
| # | HYDROPHOBIC INTERMEDIATE COMPOUNDS |
|---|---|
| A3 | 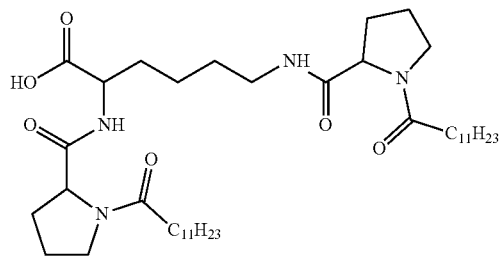 |
| A4 | 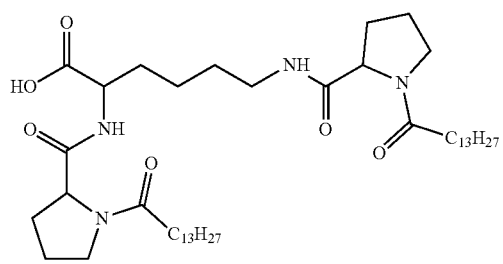 |
| A5 | 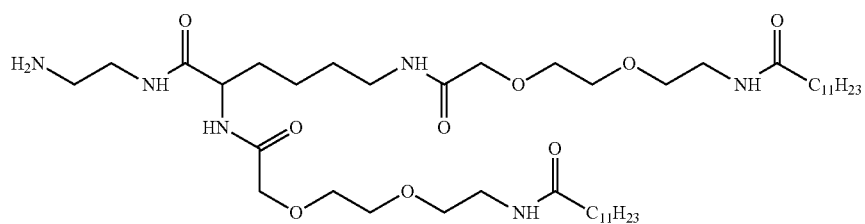 |
| A6 | 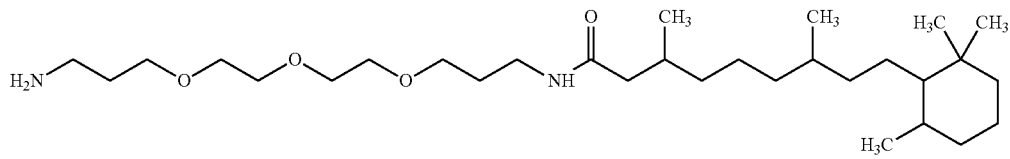 [SMILES: CC(CCCC(C)CC(=O)NCCCOCCOCCOCCCN)CCC1C(C)CCCC1(C)C] |
| A7 | 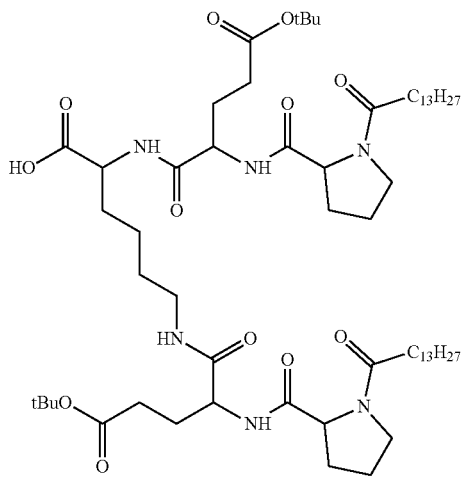 |

| # | HYDROPHOBIC INTERMEDIATE COMPOUNDS |
|---|---|
| A8 | 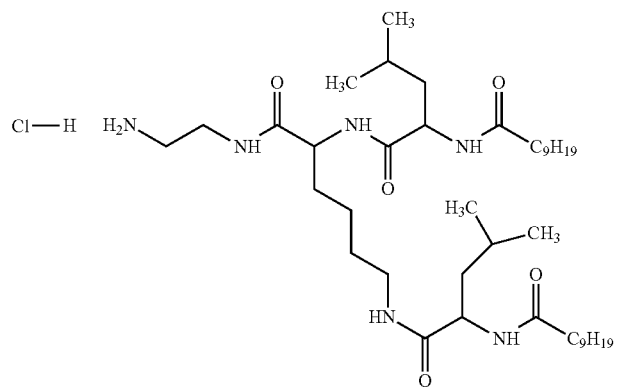 |
| A9 | 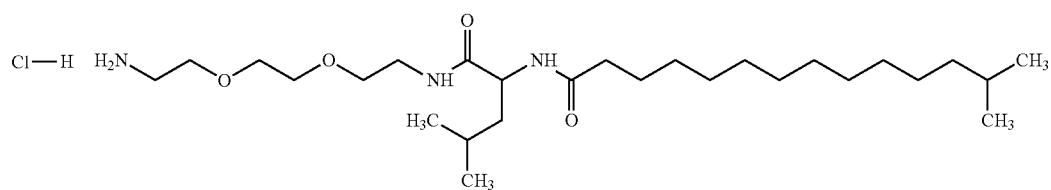 |
| A10 | 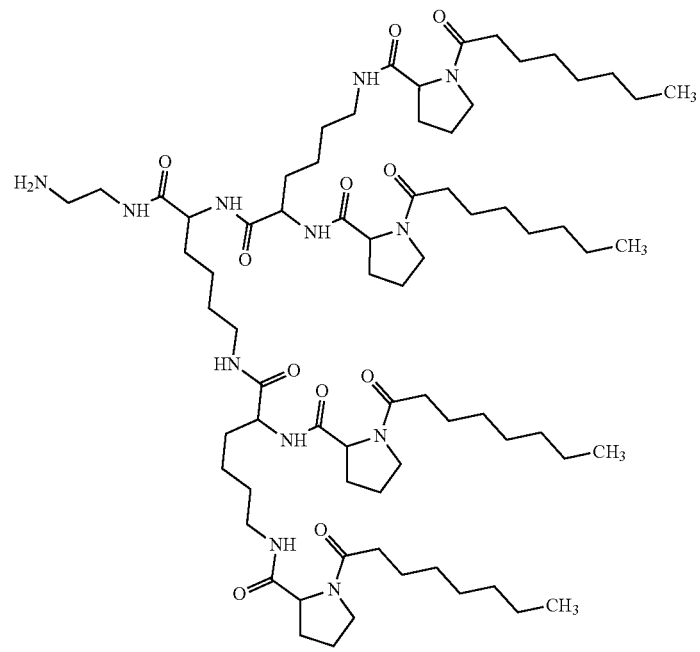 [SMILES: CCCCCCCC(=O)N1CCCC1C(=O)NCCCCC(NC(=O)C1CCCN1C(=O)CCCCCCC)C(=O)NCCCCC(NC(=O)C(CCCCNC(=O)C1CCCN1C(=O)CCCCCCC)NC(=O)C1CCCN1C(=O)CCCCCCC)C(=O)NCCN] |

| # | HYDROPHOBIC INTERMEDIATE COMPOUNDS |
|---|---|
| A11 | |
| A12 | |
| A14 | |
| A15 | |
| A16 | |

-continued
| # | HYDROPHOBIC INTERMEDIATE COMPOUNDS |
|---|---|
| A17 | 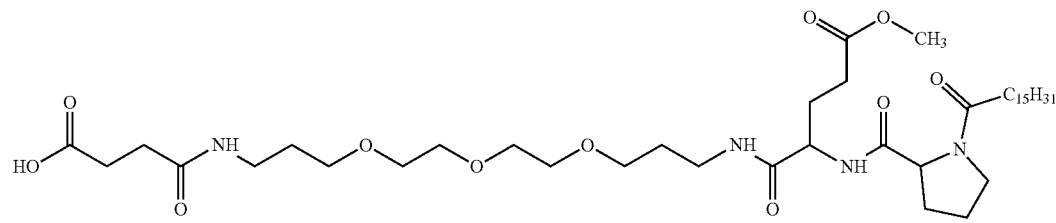 |
| A18 | 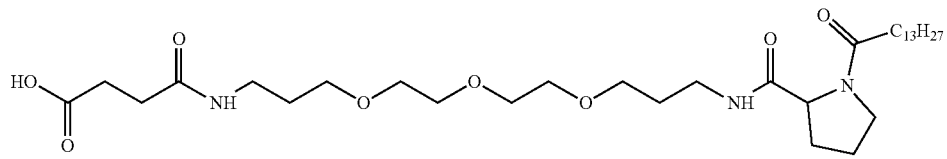 |
| A19 | 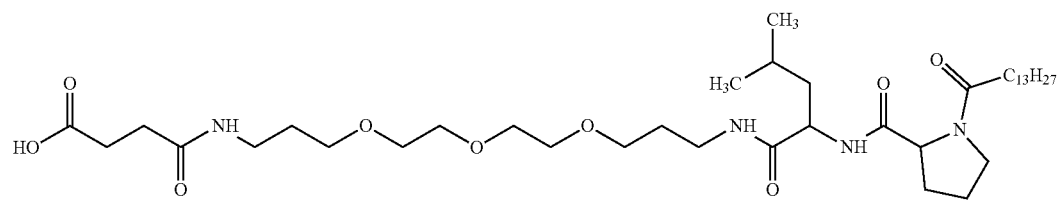 |
| A21 | 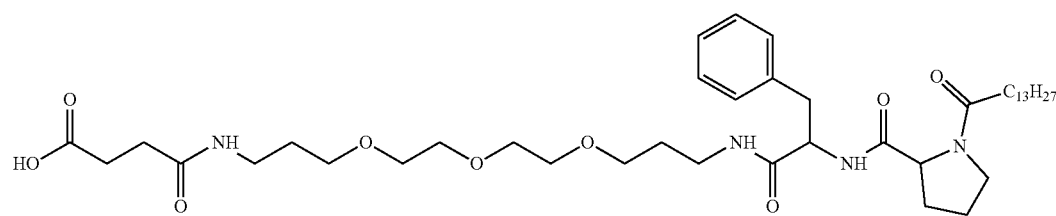 |
| A22 | 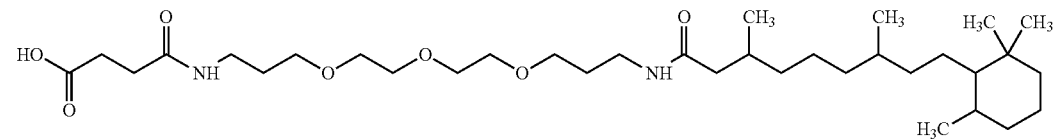 [SMILES: CC(CCCC(C)CC(=O)NCCCOCCOCCOCCCNC(=O)CCC(=O)O)CCC1C(C)CCCC1(C)C] |
| A23 | 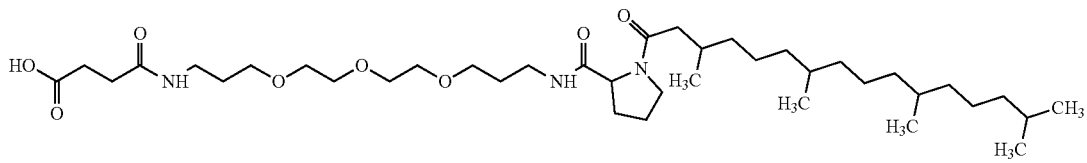 [SMILES: CC(C)CCCC(C)CCCC(C)CCCC(C)CC(=O)N1CCCC1C(=O)NCCCOCCOCCOCCCNC(=O)CCC(=O)O] |
| A26 | 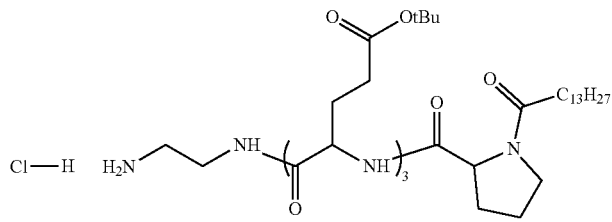 |
| A27 | 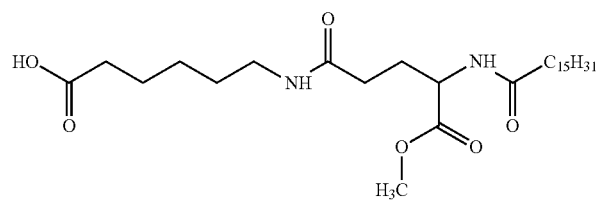 |

Example A1: Molecule A1

To a solution of L-proline (300.40 g, 2.61 mol) in 2 N aqueous sodium hydroxide (1.63 L) at 0° C. is added slowly over 1 h myristoyl chloride (322 g, 1.30 mol) in solution in dichloromethane (DCM, 1.63 L). At the end of the addition, the reaction medium is returned to 20° C. in 3 h, then stirred for a further 2 h. The mixture is cooled to 0° C. then a 37% HCl aqueous solution (215 mL) is added in 15 min. The reaction medium is stirred for 3 h from 0° C. to 20° C., then cooled to 3° C. 37% HCl (213 mL) is added in 15 min and the mixture is stirred for 1 h from 0° C. to 20° C. The organic phase is separated, washed with a 10% HCl aqueous solution (3×430 mL), an aqueous solution saturated with NaCl (430 mL), dried on $Na_2SO_4$, filtered on cotton then concentrated under reduced pressure. The residue is solubilized in heptane (1.31 L) at 50° C., then the solution is progressively returned to ambient temperature. After initiating crystallization using a glass rod, the medium is once again heated to 40° C. for 30 min then returned to ambient temperature for 4 h. A white solid of molecule A1 is obtained after filtration on a sintered filter, washing with heptane (2×350 mL) and drying under reduced pressure.

Yield: 410 g (97%)

$^1$H NMR ($CDCl_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 651.7; (calculated ([M+H]$^+$): 326.3; ([2M+H]$^+$): 651.6).

Example A2: Molecule A2

Molecule 1: Product obtained by the reaction between decanoyl chloride and L-proline.

Using a similar method to the one used for the preparation of molecule A1 and applied to decanoyl chloride (75.0 g, 393.27 mmol) and to L-proline (90.55 g, 786.53 mmol), a colorless oil of molecule 1 is obtained after washing the organic phase with a 10% HCl aqueous solution (3×125 mL), an aqueous solution saturated with NaCl (125 mL), drying on Na2SO4, cotton filtration then concentration under reduced pressure.

Yield: 104.64 g (99%)

$^1$H NMR ($CDCl_3$, ppm): 0.86 (3H); 1.10-1.51 (12H); 1.56-1.80 (2H); 1.83-2.46 (6H); 3.42-3.66 (2H); 4.37-4.41 (0.1H); 4.53-4.60 (0.9H); 10.12 (1H). LC/MS (ESI): 270.1; (calculated ([M+H]$^+$): 270.2).

Molecule A2

To a solution of molecule 1 (90.0 g, 334.09 mmol) in THF (600 mL) at 0° C. are added successively N-hydroxysuccinimide (NHS, 40.4 g, 350.80 mmol) followed by dicyclohexylcarbodiimide (DCC, 72.38 g, 350.80 mmol) in solution in THF (60 mL). After 16 h of stirring at ambient temperature, the reaction medium is filtered and introduced onto a solution of L-lysine hydrochloride (30.51 g, 167.05 mmol) and N,N-diisopropylethylamine (DIPEA, 97.16 g, 751.71 mmol) in water (66 mL) and the mixture is stirred for 48 h at 20° C. After concentration under reduced pressure, water (360 mL) is added and the mixture obtained is treated by successive addition of ethyl acetate (AcOEt, 500 mL) followed by a 5% $Na_2CO_3$ aqueous solution (1 L). The aqueous phase is then washed once again with AcOEt (200 mL), acidified by adding a 6 N HCl aqueous solution and the product is extracted with dichloromethane (DCM, 3×250 mL). The organic phase is dried on $Na_2SO_4$, filtered and concentrated under vacuum. The white solid obtained after crystallization in AcOEt is solubilized in DCM (400 mL), the organic phase is washed with a 1 N HCl aqueous solution (200 mL) followed by an aqueous solution saturated with NaCl (200 mL), dried on $Na_2SO_4$, filtered and concentrated under vacuum. A white solid of molecule A2 is obtained after crystallization in AcOEt.

Yield: 75.90 g (70%)

$^1$H NMR (DMSO-d6, ppm): 0.85 (6H); 1.10-2.04 (42H); 2.07-2.30 (4H); 2.92-3.08 (2H); 3.28-3.57 (4H); 4.07-4.28 (2H); 4.32-4.40 (1H); 7.66-7.73 (0.6H); 7.96-8.09 (1H); 8.27 (0.4H); 12.51 (1H).

LC/MS (ESI): 649.5 (calculated ([M+H]$^+$): 649.5).

Example A3: Molecule A3

Molecule 2: Product obtained by the reaction between lauroyl chloride and L-proline.

Using a similar method to the one used for the preparation of molecule A1 and applied to lauroyl chloride (27.42 g, 685.67 mmol) and to L-proline (60.0 g, 247.27 mmol), a white solid of molecule 2 is obtained.

Yield: 78.35 g (96%)

$^1$H NMR ($CDCl_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI): 298.1 (calculated ([M+H]$^+$): 298.2).

Molecule A3

Using a similar method to the one used for the preparation of molecule A2 applied to molecule 2 (42.49 g, 142.86 mmol) and to L-lysine hydrochloride (13.7 g, 75.0 mmol), a white solid of molecule A3 is obtained after crystallization in acetone.

Yield: 30.17 g (60%)

$^1$H NMR (DMSO-d6, ppm): 0.86 (6H); 1.07-2.05 (50H); 2.08-2.30 (4H); 2.93-3.09 (2H); 3.28-3.57 (4H); 4.08-4.29 (2H); 4.33-4.41 (1H); 7.70 (0.6H); 7.97-8.07 (1H); 8.28 (0.4H); 12.52 (1H).

LC/MS (ESI): 705.6; (calculated ([M+H]$^+$): 705.6).

Example A4: Molecule A4

Using a similar method to the one used for the preparation of molecule A2 applied to molecule A1 (200.0 g, 614.44 mmol) and to L-lysine hydrochloride (56.11 g, 307.22 mmol), a white solid of molecule A4 is obtained after crystallization in ethyl acetate.

Yield: 176.0 g (95%)

$^1$H NMR (DMSO-$d_6$, ppm): 0.85 (6H); 1.08-1.51 (48H); 1.53-2.04 (10H); 2.08-2.30 (4H); 2.93-3.09 (2H); 3.31-3.55 (4H); 4.10-4.40 (3H); 7.68 (0.6H); 7.97 (1H); 8.27 (0.4H); 12.50 (1H).

LC/MS (ESI): 761.8; (calculated ([M+H]$^+$): 761.6).

Example A5: Molecule A5

Molecule 3: Product obtained by the reaction between Fmoc-Lys(Fmoc)-OH and 2-Cl-trityl chloride resin.

To a suspension of Fmoc-Lys(Fmoc)-OH (7.32 g, 12.40 mmol) in DCM (60 mL) at ambient temperature is added DIPEA (4.32 mL, 24.80 mmol). After complete solubilization (10 min), the solution obtained is poured onto 2-Cl-trityl chloride resin (100-200 mesh, 1% DVB, 1.24 mmol/g) (4.00 g, 4.96 mmol) previously washed with DCM, in a reaction vessel suitable for solid substrate peptide synthesis. After 2 h of stirring at ambient temperature, HPLC grade methanol (0.8 mL/g resin, 3.2 mL) is added and the medium is stirred at ambient temperature for 15 min. The resin is filtered, washed successively with DCM (3×60 mL), DMF (2×60 mL), DCM (2×60 mL), isopropanol (1×60 mL) and DCM (3×60 mL).

Molecule 4: product obtained by the reaction between molecule 3 and an 80:20 DMF/piperidine mixture.

Molecule 3, previously washed with DMF, is treated with an 80:20 DMF/piperidine mixture (60 mL). After 30 min of stirring at ambient temperature, the resin is filtered, washed successively with DMF (3×60 mL), isopropanol (1×60 mL) and DCM (3×60 mL).

Molecule 5: Product obtained by the reaction between molecule 4 and 8-(9-Fluorenylmethyloxycarbonyl-amino)-3,6-dioxaoctanoic acid (Fmoc-O2Oc-OH).

To a suspension of Fmoc-O2Oc-OH (9.56 g, 24.80 mmol) and 1-[bis(dimethylamino)methylene]-1H-1,2,3-triazolo[4,5-b]pyridinium 3-oxide hexafluorophosphate (HATU, 9.43 g, 24.80 mmol) in a 1:1 DMF/DCM mixture (60 mL) is added DIPEA (8.64 mL, 49.60 mmol). After complete solubilization, the solution obtained is poured onto molecule 4. After 2 h of stirring at ambient temperature, the resin is filtered, washed successively with DMF (3×60 mL), isopropanol (1×60 mL) and DCM (3×60 mL).

Molecule 6: Product obtained by the reaction between molecule 5 and an 80:20 DMF/piperidine mixture.

Using a similar method to the one used for molecule 4 applied to molecule 5, molecule 6 is obtained.

Molecule 7: Product obtained by the reaction between molecule 6 and lauric acid.

Using a similar method to the one used for molecule 5 applied to molecule 6 and to lauric acid (4.97 g, 24.80 mmol) in DMF (60 mL), molecule 7 is obtained.

Molecule 8: product obtained by the reaction between molecule 7 and an 80:20 dichloromethane/1,1,1,3,3,3-hexafluoro-2-propanol (HFIP) mixture.

Molecule 7 is treated with an 80:20 dichloromethane/1,1,1,3,3,3-hexafluoro-2-propanol (HFIP) mixture (60 mL). After 20 min of stirring at ambient temperature, the resin is filtered and washed successively with dichloromethane (2×60 mL). The solvents are evaporated under reduced pressure. Two co-evaporations are then carried out on the residue with dichloromethane (60 mL) followed by diisopropylether (60 mL). A white solid of molecule 8 is obtained after recrystallization in acetonitrile.

Yield: 2.63 g (66% in 6 stages)

$^1$H NMR (CDCl$_3$, ppm): 0.87 (6H); 1.09-1.66 (40H); 1.77-1.98 (2H); 2.13-2.29 (4H); 3.24-3.75 (18H); 3.95-4.07 (4H); 4.65-4.70 (1H); 6.23-6.37 (1H); 6.39-6.62 (1H); 6.74-6.91 (1H); 7.38-7.54 (1H).

LC/MS (ESI): 801.6 (calculated ([M+H]$^+$): 801.6).

Molecule 9: product obtained by the reaction between molecule 8 and N-Boc ethylenediamine.

To a solution of molecule 8 (2.63 g, 3.29 mmol) in chloroform (20 mL) at ambient temperature are added successively N-hydroxybenzotriazole (HOBt, 654 mg, 4.27 mmol) and N-Boc ethylenediamine (BocEDA, 580 mg, 3.62 mmol). The mixture is cooled to 0° C. then (3-dimethylaminopropyl)-N'-ethylcarbodiimide hydrochloride (EDC, 819 mg, 4.27 mmol) is added. The reaction medium is stirred for 15 min at 0° C. followed by 18 h at ambient temperature. The organic phase is washed with an aqueous solution saturated with NH$_4$Cl (2×10 mL), an aqueous solution saturated with NaHCO$_3$ (2×10 mL), and an aqueous solution saturated with NaCl (2×10 mL). The organic phase is dried on Na$_2$SO$_4$, filtered and concentrated under reduced pressure. A white solid of molecule 9 is obtained after purification by silica gel chromatography (eluent: dichloromethane, methanol).

Yield: 2.37 g (76%)

$^1$H NMR (CDCl$_3$, ppm): 0.87 (6H); 1.08-1.47 (34H); 1.43 (9H); 1.48-1.70 (7H); 1.78-1.87 (1H); 2.14-2.25 (4H); 3.16-3.71 (22H); 3.92-4.04 (4H); 4.47-4.52 (1H); 5.33 (1H); 6.10 (1H); 6.65-7.01 (1H); 7.11-7.30 (2H); 7.47-7.63 (1H).

Molecule A5

To a solution of molecule 9 (2.37 g, 2.51 mmol) in dichloromethane (50 mL) at ambient temperature is added a 4 M HCl solution in dioxane (6.3 mL) then the medium is stirred for 2 h at ambient temperature. After concentration under reduced pressure, the residue is solubilized in dichloromethane (50 mL) then washed with a 1 N NaOH aqueous solution (2×12.5 mL) and an aqueous solution saturated with NaCl (25 mL). The organic phase is dried on Na$_2$SO$_4$, filtered and concentrated under reduced pressure. A white solid of molecule A5 is obtained after recrystallization in acetonitrile.

Yield: 1.57 g (74%)

$^1$H NMR (CDCl$_3$, ppm): 0.87 (6H); 1.08-1.43 (34H); 1.48-1.71 (7H); 1.74-1.93 (3H); 2.14-2.25 (4H); 2.79-2.86 (2H); 3.17-3.71 (20H); 3.93-4.05 (4H); 4.47-4.54 (1H); 6.08-6.29 (1H); 6.84-7.01 (1H); 7.15-7.32 (2H); 7.50-7.64 (1H).

LC/MS (ESI): 843.6 (calculated ([M+H]$^+$): 843.7).

Example A6: Molecule A6

Molecule 10: Product obtained by hydrogenating retinoic acid.

A solution of retinoic acid (19.0 g, 63.24 mmol) in methanol (450 mL) in the presence of 10% palladium on carbon (1.9 g) is placed in a hydrogen atmosphere (1 atm) at ambient temperature. After overnight, the reaction medium is filtered on a sintered filter and the filtrate is then concentrated under reduced pressure. A colorless oil of molecule 10 is obtained.

Yield: 19.50 g (99%)

$^1$H NMR (CDCl$_3$, ppm): 0.45-2.01 (35H); 2.10-2.17 (1H); 2.33-2.38 (1H); 11.14 (1H).

LC/MS (ESI): 309.3; (calculated ([M−H]$^-$): 309.3).

Molecule 11: Product obtained by coupling Boc-1-amino-4,7,10-trioxa-13-tridecane amine (BocTOTA) and molecule 10.

Using a similar method to the one used for the preparation of molecule 9 applied to molecule 10 (19.3 g, 62.15 mmol) and to BocTOTA (23.9 g, 74.58 mmol), an orange oil of molecule 11 is obtained.

Yield: 37.05 g (97%)

$^1$H NMR (CDCl$_3$, ppm): 0.43-1.71 (49H); 2.13-2.17 (1H); 3.17-3.24 (2H); 3.32-3.39 (2H); 3.51-3.66 (12H); 4.77 (0.1H); 4.94 (0.9H); 6.13 (0.9H); 6.29 (0.1H).

LC/MS (ESI): 613.5; (calculated ([M+H]$^+$): 613.5).

Molecule A6

Using a similar method to the one used for the preparation of molecule A5 applied to molecule 11 (34.9 g, 56.94 mmol), an orange oil of molecule A6 is obtained.

Yield: 28.5 g (97%)

$^1$H NMR (CDCl$_3$, ppm): 0.41-1.96 (42H); 2.13 (1H); 2.78 (2H); 3.31-3.36 (2H); 3.53 (4H); 3.55-3.58 (4H); 3.60-3.63 (4H); 6.43 (1H).

LC/MS (ESI): 513.5; (calculated ([M+H]$^+$): 513.5).

Example A7: Molecule A7

Molecule 12: Product obtained by the reaction between molecule 4 and Fmoc-Glu(OtBu)-OH.

To a suspension of Fmoc-Glu(OtBu)-OH (10.55 g, 24.80 mmol) and HATU (9.43 g, 24.80 mmol) in a 1:1 DMF/dichloromethane mixture (60 mL) is added DIPEA (8.64 mL, 49.60 mmol). After complete solubilization, the solution obtained is poured onto molecule 4. After 2 h of stirring at ambient temperature, the resin is filtered, washed successively with DMF (3×60 mL), isopropanol (1×60 mL) and dichloromethane (3×60 mL).

Molecule 13: Product obtained by the reaction between molecule 12 and a 50:50 DMF/morpholine mixture.

Molecule 12, previously washed with DMF, is treated with a 50:50 DMF/morpholine mixture (60 mL). After 1 h 15 of stirring at ambient temperature, the resin is filtered, washed successively with DMF (3×60 mL), isopropanol (1×60 mL) and dichloromethane (3×60 mL).

Molecule 14: Product obtained by the reaction between molecule A1 and molecule 13.

Using a similar method to the one used for molecule 12 applied to molecule 13 and to molecule A1 (8.07 g, 24.80 mmol) in DMF (60 mL), molecule 14 is obtained.

Molecule A7

Using a similar method to the one used for the preparation of molecule 8 and applied to molecule 14, a white solid of molecule A7 is obtained after purification by silica gel chromatography (eluent: DCM, methanol).

Yield: 2.92 g (52% in 6 stages)

$^1$H NMR (DMSO-d6, ppm): 0.85 (6H); 1.07-2.32 (88H); 2.95-3.09 (2H); 3.28-3.60 (4H); 4.06-4.19 (1.7H); 4.21-4.38 (2.6H); 4.40-4.46 (0.7H); 7.56-7.63 (0.7H); 7.78-8.09 (2.6H); 8.22-8.31 (0.7H); 12.64 (1H).

LC/MS (ESI) 1131.8 (calculated ([M+H]$^+$): 1131.8).

Example A8: Molecule A8

Molecule 15: Product obtained by the reaction between decanoic acid and L-leucine.

Using a similar method to the one used for the preparation of molecule A2 applied to decanoic acid (8.77 g, 50.94 mmol) and to L-leucine (7.00 g, 53.36 mmol), a white solid of molecule 15 is obtained.

Yield: 9.17 g (66%)

$^1$H NMR (DMSO-d6, ppm): 0.82-0.89 (9H); 1.18-1.65 (17H); 2.04-2.14 (2H); 4.19-4.23 (1H); 7.98 (1H); 12.40 (1H).

LC/MS (ESI): 286.2 (calculated ([M+H]$^+$): 286.2).

Molecule 16: Product obtained by the reaction between molecule 15 and L-lysine methyl ester.

To a solution of molecule 15 (9.16 g, 32.11 mmol) in THF (160 mL) are added successively triethylamine (8.12 g, 80.27 mmol) and 2-(1H-benzotriazol-1-yl)-1,1,3,3-tetramethyluronium tetrafluoroborate (TBTU) and the medium is stirred for 30 min at ambient temperature. L-lysine methyl ester dihydrochloride (3.93 g, 16.86 mmol) is added and the reaction medium is stirred for 3 h then concentrated under reduced pressure. The residue is diluted with AcOEt (200 mL), the organic phase is filtered and washed with a 1 N HCl aqueous solution then with water, dried on Na$_2$SO$_4$, filtered and concentrated under reduced pressure. A white solid of molecule 16 is obtained after triturating the residue in acetonitrile.

Yield: 7.33 g (66%)

$^1$H NMR (DMSO-d6, ppm): 0.80-0.91 (18H); 1.06-1.72 (38H); 2.03-2.16 (4H); 2.91-3.07 (2H); 3.60 (1.15H); 3.61 (1.85H); 4.13-4.28 (2H); 4.33-4.44 (1H); 7.79-7.92 (3H); 8.13-8.26 (1H).

LC/MS (ESI) 695.7 (calculated ([M+H]$^+$): 695.6).

Molecule 17: Product obtained by saponifying molecule 16.

To a solution of molecule 16 (7.33 g, 10.55 mmol) in a THF/methanol/water mixture (105 mL) is added LiOH (505.13 mg, 21.09 mmol) at 0° C. then the medium is stirred for 20 h at ambient temperature and concentrated under reduced pressure. The aqueous phase is acidified with a 1 N HCl solution to pH 1 and the solid formed is filtered, washed with water and dried under reduced pressure to get a white solid of molecule 17.

Yield: 7.09 g (99%)

$^1$H NMR (DMSO-d6, ppm): 0.80-0.89 (18H); 1.18-1.73 (40H); 2.03-2.16 (4H); 2.91-3.05 (2H); 4.03-4.13 (1H); 4.21-4.27 (1H); 4.31-4.40 (1H); 7.79-8.02 (4H).

LC/MS (ESI): 681.7 (calculated ([M+H]$^+$): 681.6).

Molecule 18: Product obtained by the reaction between molecule 17 and N-Boc ethylenediamine.

Using a similar method to that used for the preparation of molecule 16 applied to molecule 17 (7.09 g, 10.41 mmol) and to N-Boc ethylenediamine (1.83 g, 11.45 mmol), a white solid of molecule 18 is obtained after trituration in acetonitrile.

Yield: 6.64 g (77%)

$^1$H NMR (DMSO-d6, ppm): 0.80-0.91 (18H); 1.15-1.73 (49H); 2.03-2.18 (4H); 2.92-3.13 (6H); 4.05-4.30 (3H); 6.71-6.83 (1H); 7.69-8.23 (5H).

LC/MS (ESI): 824.0 (calculated ([M+H]$^+$): 823.7).

Molecule A8

Using a similar method to the one used for molecule A5 applied to molecule 18 (3.00 g, 3.64 mmol) without basic washing, a beige solid of molecule A8 in hydrochloride salt form is obtained after co-evaporating the residue 4 times in methanol.

Yield: 2.66 g (96%)

$^1$H NMR (DMSO-d6, ppm): 0.80-0.91 (18H); 1.15-1.76 (40H); 2.03-2.19 (4H); 1.78-2.89 (2H); 2.91-3.07 (2H); 3.22-3.37 (2H); 4.08-4.14 (1H); 4.17-4.28 (2H); 7.81-8.36 (8H).

LC/MS (ESI): 723.7 (calculated ([M+H]$^+$): 723.6).

Example A9: Molecule A9

Molecule 19: 13-Methyltetradecanoic acid.

In a dry triple neck round bottom flask under argon, magnesium (5.50 g, 226.3 mmol) chips are introduced. The magnesium is covered with anhydrous THF (25 mL) and a few drops of 1-bromo-2-methylpropane are added at ambient temperature to initiate the reaction. After observing an exotherm and slight turbidity of the medium, the remaining 1-bromo-2-methylpropane (28.42 g, 207 mmol) diluted in THF (60 mL) is added dropwise in 1 h whereas the temperature of the medium remains stable from 65 to 70° C. The reaction medium is then reflux heated for 2 h.

In a triple neck round bottom flask under argon, to a solution of CuCl (280 mg, 2.83 mmol) dissolved in N-methylpyrrolidone (NMP) previously distilled at 0° C. is added dropwise a solution of 11-bromoundecanoic acid (25 g, 94.27 mmol) dissolved in THF (60 mL). To this solution is then added dropwise the slightly warm organomagnesium solution diluted in THF (50 mL) in order to maintain the temperature of the medium below 25° C. The mixture is then stirred at ambient temperature for 16 h. The medium is cooled to 0° C. and the reaction is stopped by slowly adding a 1 N HCl aqueous solution to pH 1 (300 mL) and the medium is extracted with hexane (100 mL) and with ethyl acetate (2×75 mL). After washing the organic phase with a 1 N HCl aqueous solution (100 mL), water (100 mL) and drying on $Na_2SO_4$, the solution is filtered and concentrated under vacuum to produce a brown solid. After purification by flash chromatography (cyclohexane, ethyl acetate), a white solid is obtained.

Yield: 18.1 g (79%)

$^1$H NMR ($CDCl_3$, ppm): 0.87 (6H); 1.11-1.18 (2H); 1.20-1.38 (16H); 1.51 (1H); 1.63 (2H); 2.35 (2H).

Molecule 20: Product obtained by reacting molecule 19 and L-leucine.

To a solution of molecule 19 (18.05 g, 74.46 mmol) in THF (745 mL) at ambient temperature are added successively DCC (14.63 g, 70.92 mmol) and NHS (8.16 g, 70.92 mmol). After 40 h of stirring at ambient temperature, the medium is cooled to 0° C. for 20 min, filtered on a sintered filter. L-leucine (9.77 g, 74.46 mmol), DIPEA (86 mL) and water (150 mL) are added to the filtrate. After 20 h of stirring at ambient temperature, the medium is diluted with a saturated aqueous solution of $NaHCO_3$ (200 mL). The aqueous phase is washed with ethyl acetate (2×200 mL) and acidified with a 2 N HCl solution to pH 1. The precipitate is filtered, rinsed thoroughly with water and dried under vacuum at 50° C. Three times, the solid is triturated in pentane, sonicated then filtered to produce a white solid.

Yield: 18.8 g (75%)

$^1$H NMR ($CDCl_3$, ppm): 0.86 (6H); 0.96 (6H); 1.12-1.18 (2H); 1.20-1.78 (22H); 2.24 (2H); 4.58-4.63 (1H); 5.89 (1H).

LC/MS (ESI): 356.2; (calculated ([M+H]$^+$): 356.6).

Molecule 21: Product obtained by the reaction between molecule 20 and Boc-tri(ethyleneglycol)diamine.

To a solution of molecule 20 (16.7 g, 46.97 mmol) in THF (235 mL) are added successively DIPEA (20.3 mL) and TBTU at ambient temperature. After 20 min of stirring, Boc-tri(ethyleneglycol)diamine (14 g, 56.36 mmol) is added. After stirring at ambient temperature for 5 h, the mixture is concentrated under vacuum. The residue is taken up with ethyl acetate (500 mL), washed with a saturated aqueous solution of NaHCO3 (3×200 mL), a 1 N HCl aqueous solution (3×200 mL) and an aqueous solution saturated with NaCl (3×200 mL). After drying on Na2SO4, filtration and concentration under vacuum, the residue is purified by flash chromatography (cyclohexane, ethyl acetate, methanol) to produce a colorless oil.

Yield: 23.5 g (85%)

$^1$H NMR ($CDCl_3$, ppm): 0.86 (6H); 0.93 (6H); 1.10-1.17 (2H); 1.19-1.08 (31H); 2.18 (2H); 3.23-3.65 (12H); 4.41-4.56 (1H); 5.12-5.47 (1H); 5.99-6.11 (0.75H); 6.48-6.65 (1H); 7.30-7.40 (0.25H).

Molecule A9

Using a similar method to the one used for the preparation of molecule A5 applied to molecule 21 (23.46 g, 40.04 mmol) without basic washing, the residue obtained after concentration under vacuum is triturated in an acetonitrile/acetone mixture. The supernatant is removed and the pasty residue is dried under vacuum. The residue is triturated in acetone (150 mL) and the white solid of molecule A9 in hydrochloride salt form is filtered, rinsed with acetone then dried under vacuum.

Yield: 13.0 g (64%)

$^1$H NMR (DMSO-d6, ppm): 0.79-0.90 (12H); 1.09-1.61 (24H); 2.03-2.17 (2H); 2.92-2.98 (2H); 3.15-3.23 (2H); 3.40 (2H); 3.50-3.58 (4H); 3.61 (2H); 4.30-4.23 (1H); 7.88-8.14 (5H).

LC/MS (ESI): 486.4; (calculated ([M−Cl]$^+$): 486.8).

Example A10: Molecule A10

Molecule 22: Product obtained by the reaction between octanoyl chloride and L-proline.

Using a similar method to the one used for the preparation of molecule A1 and applied to octanoyl chloride (150.0 g, 0.922 mol) and to L-proline (212.3 g, 1.844 mol), a colorless oil of molecule 22 is obtained after washing the organic phase with a 10% HCl aqueous solution (3×300 mL), an aqueous solution saturated with NaCl (300 mL), drying on $Na_2SO_4$, filtration on cotton, concentration under reduced pressure, then the residue is purified by flash chromatography (eluent: DCM, MeOH)

Yield: 134 g (60%)

$^1$H NMR ($CDCl_3$, ppm): 0.87 (3H); 1.10-1.52 (8H); 1.57-1.74 (2H); 1.79-2.52 (6H); 3.37-3.67 (2H); 4.37-4.42 (0.07H); 4.53-5.63 (0.93H); 9.83 (1H).

LC/MS (ESI): 242.1; (calculated ([M+H]$^+$): 242.2).

Molecule 23: Product obtained by coupling molecule 22 and L-leucine.

To a solution of molecule 22 (132 g, 0.547 mol) in THF (924 mL) cooled to a temperature below 5° C. are added successively NHS (66.1 g, 0.574 mol) and DCC (118.5 g, 0.574 mol). After 21 h of stirring, the precipitate is removed by precipitation and the filtrate is added in 30 min to a solution of L-lysine (41.98 g, 0.287 mol) in a mixture of deionized water (82 mL) and DIPEA (476 mL, 2.735 mol) at 15° C. After 23 h of stirring at ambient temperature, the reaction medium is concentrated under reduced pressure to produce an oily residue which is diluted in water (1.3 L). The aqueous phase is washed twice with AcOEt (2×0.5 L), cooled to a temperature below 10° C., acidified by adding a 6 N HCl solution (120 mL) to pH 1 then extracted three times with DCM (3×0.6 L). The organic phases are combined, washed with a saturated NaCl solution (0.6 L), dried on $Na_2SO_4$ then concentrated under reduced pressure. The foam obtained is taken up with acetone (240 mL) at reflux for 2 h. After leaving overnight at 10° C., pentane (240 mL) is added dropwise. After 1 h of stirring, the precipitate is recovered by filtering under vacuum, washed with a 1:1 mixture of pentane and acetone (150 mL) then dried under a vacuum.

Yield: 83.9 g (52%)

$^1$H NMR ($CDCl_3$, ppm): 0.87 (6H); 1.06-1.78 (25H); 1.80-2.41 (13H); 2.80-3.72 (6H); 4.30-4.39 (0.15H); 4.46-4.70 (2.85H); 7.84 (1H); 7.93 (1H).

LC/MS (ESI): 593.5; (calculated ([M+H]$^+$): 593.4).

Molecule 24: Product obtained by coupling molecule 23 and L-lysine methyl ester (LysOMe).

To molecule 23 (76.26 g, 0.129 mol) are successively added HOPO (3.57 g, 32.1 mmol), LysOMe dihydrochloride (15.0 g, 64.3 mmol) and EDC (34.53 g, 0.18 mol). Then DMF (600 mL) previously cooled to 5° C. is added. After dissolution, triethylamine (43.9 mL, 0.315 mol) is added dropwise while maintaining the temperature below 5° C. for 2 h after addition. After leaving overnight at ambient temperature, the reaction medium is poured onto a mixture of water/ice (2 kg) and DCM (0.5 L). After 15 min of stirring, the phases are separated. The aqueous phase is extracted twice with DCM (2×0.4 L). The organic phases are combined, washed with a 1 N HCl solution (0.5 L) then with a saturated NaCl solution (0.5 L), dried on $Na_2SO_4$, concentrated under reduced pressure, then the residue is purified by flash chromatography (eluent: DCM, MeOH).

Yield: 56.7 g (67%)

$^1$H NMR ($CDCl_3$, ppm): 0.87 (12H); 1.10-2.40 (82H); 2.86-3.72 (17H); 4.16-4.60 (7H); 6.83-8.01 (6H).

Molecule A10

A solution of molecule 24 (4.0 g, 3.05 mmol) in ethylenediamine (30 mL) is heated at 50° C. overnight. The reaction medium is then diluted with methyl-tetrahydrofuran then the organic phase is washed 4 times with a saturated NaCl solution (4×30 mL) then 2 times with water (2×50 mL) before being dried on $Na_2SO_4$ and concentrated under reduced pressure. The residue is solubilized in acetonitrile at reflux for 30 min then the solution is cooled to ambient temperature under stirring overnight. The white precipitate is then recovered by filtering under vacuum, washed with cold acetonitrile (2×20 mL) then dried under vacuum.

Yield: 3.0 g (74%)

$^1$H NMR ($CDCl_3$, ppm): 0.87 (12H); 1.09-2.37 (84H); 2.74-4.56 (25H); 6.85-8.00 (7H).

LC/MS (ESI): 1338.0 (calculated ([M+H]$^+$): 1338.0).

Example A11: Molecule A11

Molecule 25: Product obtained by the reaction between molecule 13 and lauric acid.

Using a similar method to the one used for molecule 5 applied to molecule 13 (28 mmol) and lauric acid (28.04 g, 140 mmol) in DMF (330 mL), molecule 25 is obtained.

Molecule A11

Using a similar method to the one used for molecule 8 applied to molecule 25, a white solid of molecule A11 is obtained after recrystallization in acetonitrile.

Yield: 13.9 g (56% in 6 stages)

$^1$H NMR (DMSO-d6, ppm): 0.85 (6H); 1.05-1.61 (60H); 1.62-1.75 (2H); 1.78-1.91 (2H); 2.04-2.27 (8H); 2.96-3.06 (2H); 4.08-4.13 (1H); 4.17-4.22 (1H); 4.27-4.34 (1H); 7.82 (1H); 7.86 (1H); 7.90 (1H); 8.03 (1H); 12.54 (1H).

LC/MS (ESI+): 881.7 (calculated ([M+H]$^+$): 881.7).

Example A12: Molecule A12

Molecule 26: Product obtained by the reaction between molecule 13 and Fmoc-Glu(OtBu)-OH.

Using a similar method to the one used for molecule 5 applied to molecule 13 (9.92 mmol) and to Fmoc-Glu(OtBu)-OH (21.10 g, 49.60 mmol) in N-methyl-2-pyrrolidone (NMP, 120 mL), molecule 26 is obtained.

Molecule 27: Product obtained by the reaction between molecule 26 and an 80:20 NMP/piperidine mixture.

Using a similar method to the one used for molecule 4 applied to molecule 26, using NMP instead of DMF, molecule 27 is obtained.

Molecule 28: Product obtained by the reaction between molecule 27 and Fmoc-Glu(OtBu)-OH.

Using a similar method to the one used for molecule 26 applied to molecule 27 and to Fmoc-Glu(OtBu)-OH (21.10 g, 49.60 mmol), molecule 28 is obtained.

Molecule 29: Product obtained by the reaction between molecule 28 and an 80:20 NMP/piperidine mixture.

Using a similar method to the one used for molecule 27 applied to molecule 28, molecule 29 is obtained.

Molecule 30: Product obtained by the reaction between molecule 29 and molecule A1.

Using a similar method to the one used for molecule 26 applied to molecule 29 (4.96 mmol) and to molecule A1 (8.07 g, 24.80 mmol), molecule 30 is obtained.

Molecule A12

Using a similar method to the one used for molecule 8 applied to molecule 30, a white solid of molecule A12 is obtained after purification by flash chromatography (DCM, MeOH).

Yield: 4.6 g (50% in 10 stages)

$^1$H NMR ($CD_3OD$, ppm): 0.90 (6H); 1.22-2.53 (140H); 3.12-3.25 (2H); 3.43-3.80 (4H); 4.17-4.54 (9H).

LC/MS (ESI+): 1894.5 (calculated ([M+Na]$^+$): 1894.2).

Example A14: Molecule A14

Molecule 33: product obtained by reacting N-□-Boc-L-Lysine and palmitoyl chloride Using a similar method to the one used for the preparation of molecule A1 applied to N-□-Boc-L-Lysine (53.76 g, 218.28 mmol) and to palmitoyl chloride (50.00 g, 181.90 mmol), a white solid of molecule 33 is obtained after recrystallizing 2 times in acetonitrile and purification by flash chromatography (eluent: dichloromethane, methanol).

Yield: 49.10 g (70%)

$^1$H NMR (DMSO-d$_6$, ppm): 0.85 (3H); 1.09-1.66 (32H); 1.37 (9H); 2.01 (2H); 2.93-3.06 (2H); 3.78-3.85 (1H); 6.61-6.68 (0.2H); 6.96-6.98 (0.8H); 7.66-7.75 (1H); 12.38 (1H).

LC/MS (ESI): 385.1 (calculated ([M-Boc+H]$^+$): 385.3).

Molecule 34: Product obtained by the reaction between molecule 33 and methyl iodide.

To a solution of molecule 33 (23.40 g, 48.28 mmol) in DMF (200 mL) at ambient temperature are added $K_2CO_3$ (10.01 g, 72.41 mmol) followed by methyl iodide (5.96 mL, 98.55 mmol). The medium is stirred for 48 h. Water (350 mL) is added and the suspension is stirred for 15 min. The mixture is then filtered on a sintered filter and the solid obtained is rinsed with water (2×250 mL) and dried under vacuum. The solid is then solubilized in DCM (300 mL). The solution is washed with water (200 mL) then with an aqueous solution saturated with NaCl (200 mL), dried on $Na_2SO_4$, filtered and concentrated under reduced pressure. A white solid of molecule 34 is obtained after recrystallization in acetonitrile.

Yield: 19.22 g (80%)

$^1$H NMR ($CDCl_3$, ppm): 0.87 (3H); 1.06-2.23 (34H); 1.43 (9H); 3.09-3.33 (2H); 3.72 (3H); 3.94-4.35 (1H); 4.69-5.23 (1H); 5.33-5.75 (1H).

LC/MS (ESI): 543.3 (calculated ([M–H+HCOOH]$^-$): 543.4).

Molecule 35: Product obtained by hydrolyzing molecule 34 with hydrochloric acid

Using a similar method to that used for the preparation of molecule A5 applied to molecule 34 in solution in a 1:1 DCM/methanol mixture (385 mL), a white solid of molecule 35 is obtained after concentration under reduced pressure and co-evaporation with DCM followed by methanol.

Yield: 16.73 g (99%)

$^1$H NMR (DMSO-d$_6$, ppm): 0.85 (3H); 1.08-1.50 (30H); 1.67-1.84 (2H); 2.03 (2H); 2.94-3.13 (2H); 3.74 (3H); 3.92-4.01 (1H); 7.77-7.87 (1H); 8.25-8.73 (3H).

LC/MS (ESI): 399.2 (calculated ([M+H]$^+$): 399.4).

Molecule A14

To a suspension of molecule 35 (14.70 g, 33.79 mmol) in a mixture of methyl-THF (338 mL) and DMF (30 mL) are added successively DIPEA (17.70 mL, 101.40 mmol) followed by a solution of succinic anhydride (5.07 g, 50.68 mmol) in THF (60 mL). The medium is stirred for 4 h at ambient temperature. Methyl-THF (100 mL) is added and the organic phase is washed with a 5% HCl aqueous solution (300 mL). The aqueous phase is extracted with methyl-DCM (2×150 mL). The combined organic phases are washed with water (2×150 mL) then with an aqueous solution saturated with NaCl (150 mL), dried on $Na_2SO_4$, filtered and concentrated under reduced pressure. The crude product is purified by flash chromatography (eluent: DCM, methanol) then solubilized in methyl-THF. The purified product is then suspended in water. The suspension is stirred by sonication for 20 min followed by magnetic stirring for 30 min. A white solid of molecule A14 is obtained after filtration and drying under reduced pressure.

Yield: 12.99 g (77%)

$^1$H NMR (DMSO-$d_6$, ppm): 0.85 (3H); 1.08-1.71 (32H); 2.02 (2H); 2.29-2.45 (4H); 2.94-3.04 (2H); 3.61 (3H); 4.14-4.22 (1H); 7.70 (1H); 8.20 (1H); 12.04 (1H).

LC/MS (ESI): 499.3 (calculated ([M+H]$^+$): 499.4).

Example A15: Molecule A15 molecule 36: product obtained by coupling L-proline and palmitoyl chloride

Using a similar method to the one used for the preparation of molecule A1 applied to L-proline (38.05 g, 906.00 mmol) and to palmitoyl chloride (14.01 g, 350.16 mmol), a white solid of molecule 36 is obtained.

Yield: 47.39 g (96%)

$^1$H NMR (CDCl$_3$, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H) 6.60-8.60 (1H).

LC/MS (ESI): 354.5 (calculated ([M+H]$^+$): 354.3).

Molecule 37: Product obtained by the reaction between molecule 36 and N-Bocethylenediamine.

Using a similar method to the one used for molecule 9 applied to molecule 36 (75.1 g, 212.4 mmol), a white solid of molecule 37 is obtained after trituration in diisopropyl-ether (3×400 mL) and vacuum-drying at 40° C.

Yield: 90.4 g (86%).

$^1$H NMR (CDCl$_3$, ppm): 0.88 (3H); 1.20-1.37 (24H); 1.44 (9H); 1.54-1.70 (2H); 1.79-1.92 (1H); 1.92-2.04 (1H); 2.03-2.17 (1H); 2.17-2.44 (3H); 3.14-3.36 (4H); 3.43 (1H); 3.56 (1H); 4.29 (0.1H); 4.51 (0.9H); 4.82 (0.9H); 5.02 (0.9H); 6.84 (0.1H); 7.22 (0.9H).

Molecule 38: Product obtained by hydrolyzing molecule 37 with hydrochloric acid

Using a similar method to the one used for the preparation of molecule A5 applied to molecule 37 (38.17 g, 76.99 mmol), a white solid of molecule 38 is obtained.

$^1$H NMR (CDCl$_3$, ppm): 0.88 (3H); 1.07-1.40 (24H); 1.49-1.63 (2H); 1.77-2.18 (4H); 2.18-2.45 (2H); 3.14-3.32 (2H); 3.42-3.63 (2H); 3.63-3.84 (2H); 4.37 (0.1H); 4.48 (0.9H); 6.81-8.81 (4H).

LC/MS (ESI): 396.5; (calculated ([M+H]$^+$): 396.4).

Molecule A15

Using a similar method to the one used for the preparation of molecule A14 applied to molecule 38 (10.00 g, 253.00 mmol), a white solid of molecule A15 is obtained.

Yield: 10.00 g (80%)

$^1$H NMR (DMSO, ppm): 0.85 (3H); 1.07-1.51 (26H); 1.69-2.02 (4H); 2.08-2.53 (6H); 3.01-3.18 (4H); 3.39-3.58 (2H); 4.13-4.18 (0.7H); 4.23-4.27 (0.3H); 7.70-7.78 (1.4H); 7.81-7.86 (0.3H); 8.00-8.04 (0.3H); 12.08 (1H).

LC/MS (ESI): 496.3 (calculated ([M+H]$^+$): 496.4).

Example A16: Molecule A16

Molecule 39: Product obtained by the reaction between molecule 36 and Boc-1-amino-4,7,10-trioxa-13-tridecane amine.

Using a similar method to the one used for the preparation of molecule 9 applied to molecule 36 (17.00 g, 48.08 mmol) and to Boc-1-amino-4,7,10-trioxa-13-tridecane amine (18.49 g, 57.70 mmol), a pale yellow oil of molecule 39 is obtained.

Yield: 31.11 g (98%)

$^1$H NMR (DMSO-$d_6$, ppm): 0.85 (3H); 1.17-1.31 (24H); 1.37 (9H); 1.41-1.51 (2H); 1.54-1.67 (4H); 1.69-2.02 (4H); 2.08-2.29 (2H); 2.91-3.00 (2H); 3.01-3.17 (2H); 3.31-3.58 (14H); 4.20 (0.65H); 4.26 (0.35H); 6.29-6.82 (1H); 7.68 (0.65H); 8.02 (0.35H).

LC/MS (ESI): 656.4 (calculated ([M+H]$^+$): 656.5).

Molecule 40: Product obtained by hydrolyzing molecule 39 with hydrochloric acid

Using a similar method to the one used for the preparation of molecule A5 applied to molecule 39 (31.11 g, 47.43 mmol), a yellow wax of molecule 40 is obtained.

Yield: 27 g (97%)

$^1$H NMR (DMSO-$d_6$, ppm): 0.85 (3H); 1.18-1.31 (24H); 1.40-1.51 (2H); 1.55-1.67 (2H); 1.70-2.04 (6H); 2.09-2.30 (2H); 2.78-2.89 (2H); 2.99-3.18 (2H); 3.33-3.58 (14H); 4.19 (0.65H); 4.27 (0.35H); 7.55-8.14 (4H).

LC/MS (ESI): 556.3 (calculated ([M+H]$^+$): 556.5).

Molecule A16

Molecule 40 (26.40 g, 44.50 mmol) in hydrochloride form is solubilized in a mixture of DCM (350 mL) and an aqueous solution of NaHCO$_3$ (350 mL). The organic phase is separated and the aqueous phase is extracted with DCM (2×150 mL). The organic phases are combined dried on Na$_2$SO$_4$, filtered and concentrated under reduced pressure to produce a colorless oil. Using a similar method to the one used for the preparation of molecule A14, a yellow resin of molecule A16 is obtained after purification by flash chromatography (eluent: DCM, methanol).

Yield: 19.93 g (68%)

$^1$H NMR (DMSO-$d_6$, ppm): 0.85 (3H); 1.18-1.30 (24H); 1.40-1.51 (2H); 1.55-1.67 (4H); 1.70-2.02 (4H); 2.07-2.45 (6H); 2.99-3.18 (4H); 3.33-3.57 (14H); 4.19 (0.65H); 4.26 (0.35H); 7.68 (0.65H); 7.78 (1H); 8.02 (0.35H); 12.03 (1H).

LC/MS (ESI): 656.3 (calculated ([M+H]$^+$): 656.5).

Example A17: Molecule A17

Molecule 41: Product obtained by solid phase peptide synthesis (SPPS)

Molecule 41 is obtained by means of the conventional solid phase peptide synthesis (SPPS) method on 2-chlorotrityl resin To a solution of 4,7,10-trioxa-1,13-tridecanediamine (TOTA, 76.73 mL, 350 mmol) in DCM (350 mL) is added DIPEA (60.96 mL, 350 mmol). This solution is then poured onto the 2-chlorotrityl resin (47.30 g, 0.74 mmol/g) previously washed with DCM in a reaction vessel suitable for SPPS. After 1.5 h of stirring at ambient temperature, methanol (26 mL) is added and the medium is stirred for 15 min. The resin is filtered, washed successively with DCM (3×350 mL), DMF (2×350 mL), DCM (2×350 mL), isopropanol (1×350 mL) and DCM (3×350 mL). The □-methyl ester of N-Fmoc-L-glutamic acid (1,5 eq) followed by molecule 36 (1.5 eq) are coupled using the coupling agent 1-[bis(dimethylamino)methylene]-1H-1,2,3-triazolo[4,5-b]pyridinium 3-oxide hexafluorophosphate (HATU, 1.5 equivalents) and DIPEA (3 equivalents) in a 1:1 DCM/DMF mixture. A 1:1 DMF/morpholine mixture is used for the cleavage step of the Fmoc protecting group. The resin is washed with DCM, DMF and methanol after each coupling and deprotection step. The cleavage of the product from the resin is carried out using a 1:1 TFA/DCM mixture. The solvents are then evaporated under vacuum; the residue is solubilized in DCM (500 mL) and the organic phase is washed with a 5% $Na_2CO_3$ aqueous solution (500 mL). After drying on $Na_2SO_4$, the organic phase is filtered, concentrated under vacuum and a yellow oil of molecule 41 is obtained after drying under reduced pressure.

Yield: 15.95 g (65%)

1H NMR (DMSO-d6, ppm): 0.85 (3H); 1.16-1.31 (24H); 1.38-1.68 (6H); 1.68-2.37 (12H); 2.58 (2H); 3.01-3.17 (2H); 3.31-3.55 (14H); 3.58 (3H); 4.09-4.18 (0.7H); 4.18-4.29 (1H); 4.36-4.43 (0.3H); 7.62 (0.7H); 7.86 (0.7H); 7.98 (0.3H); 8.23 (0.3H).

LC/MS (ESI): 699.4 (calculated ([M+H]+): 699.5).

Molecule A17

Using a similar method to the one used for the preparation of molecule A14 applied to molecule 41 (14.05 g, 20.10 mmol), a yellow resin of molecule A17 is obtained after purification by flash chromatography (eluent: DCM, methanol).

Yield: 7.70 g (48%)

1H NMR (DMSO-d6, ppm): 0.85 (3H); 1.17-1.31 (24H); 1.38-1.54 (2H); 1.54-1.68 (4H); 1.68-2.21 (7H); 2.21-2.36 (5H); 2.36-2.44 (2H); 3.01-3.16 (4H); 3.34-3.55 (14H); 3.57 (3H); 4.10-4.18 (0.7H); 4.18-4.30 (1H); 4.40 (0.3H); 7.60 (0.7H); 7.78 (1H); 7.85 (0.7H); 7.95 (0.3H); 8.22 (0.3H); 12.06 (1H).

LC/MS (ESI): 799.5 (calculated ([M+H]+): 799.5).

Example A18: Molecule A18

Molecule 42: Product obtained by the reaction between molecule A1 and Boc-1-amino-4,7,10-trioxa-13-tridecane amine.

Using a similar method to the one used for the preparation of molecule 18 applied to molecule A1 (44.80 g, 137.64 mmol) and to Boc-1-amino-4,7,10-trioxa-13-tridecane amine (52.92 g, 165.16 mmol), an orange oil of molecule 42 is obtained.

Yield: 85.63 g (99%)

1H NMR (CDCl_3, ppm): 0.87 (3H); 1.08-1.56 (20H); 1.43 (9H); 1.58-1.67 (2H); 1.70-2.00 (6H); 2.04-2.41 (4H); 3.16-3.77 (18H); 4.26-4.29 (0.2H); 4.50-4.54 (0.8H); 4.68-5.10 (1H); 6.74 (0.2H); 7.19 (0.8H).

LC/MS (ESI): 628.4; (calculated ([M+H]$^+$): 628.5).

Molecule 43: Product obtained by hydrolyzing molecule 42 with hydrochloric acid

Using a similar method to the one used for the preparation of molecule A5 applied to molecule 42 (43.40 g, 69.12 mmol), a white solid of molecule 43 in hydrochloride salt form is obtained after trituration in diethylether, solubilisation of the residue in water and lyophilization.

Yield: 38.70 g (98%)

1H NMR (DMSO, ppm): 0.85 (3H); 1.07-1.38 (20H); 1.41-1.52 (2H); 1.55-1.66 (2H); 1.70-2.02 (6H); 2.08-2.30 (2H); 2.78-2.87 (2H); 3.00-3.16 (2H); 3.29-3.66 (14H); 4.16-4.22 (0.65H); 4.25-4.30 (0.35H); 7.74 (0.65H); 7.86 (3H); 8.10 (0.35H).

LC/MS (ESI): 528.4; (calculated ([M+H]$^+$): 528.4).

Molecule A18

Using a similar method to the one used for the preparation of molecule A14 applied to molecule 43 (13.09 g, 24.8 mmol), a yellow resin of molecule A18 is obtained after purification by flash chromatography (eluent: DCM, methanol).

Yield: 8.53 g (55%)

1H NMR (DMSO-d6, ppm): 0.86 (3H); 1.10-1.39 (20H); 1.42-1.51 (2H); 1.57-1.67 (4H); 1.71-2.03 (4H); 2.09-2.32 (4H); 2.42 (2H); 3.01-3.17 (4H); 3.36-3.57 (14H); 4.18-4.21 (0.65H); 4.24-4.28 (0.35H); 7.69 (0.65H); 7.80 (1H); 8.03 (0.35H); 12.04 (1H).

LC/MS (ESI): 628.5 (calculated ([M+H]$^+$): 628.5).

Example A19: Molecule A19

Molecule 44: Product obtained by SPPS

By means of a similar SPPS method to the one used for the preparation of molecule 41 and applied to TOTA, to N-Fmoc-L-Leucine, N-Fmoc-L-proline and to myristic acid, an orange oil of molecule 44 is obtained.

Yield: 19.87 g (69%)

$^1$H NMR (CDCl_3, ppm): 0.72-1.06 (9H); 1.09-1.42 (20H); 1.42-2.40 (17H); 2.80 (2H); 3.22-3.81 (16H); 4.25-4.61 (2H); 6.56-7.23 (2H).

LC/MS (ESI): 641.5; (calculated ([M+H]$^+$): 641.5).

Molecule A19

After a similar method to the one used for the preparation of molecule A14 applied to molecule 44 (13.09 g, 204.42 mmol), 4.81 g of the product obtained by purification by flash chromatography (eluent: DCM, methanol) is solubilized in a mixture of DCM (50 mL) and THF (5.5 mL) then washed with an aqueous solution saturated with NaCl (50 mL), a 0.1 N HCl aqueous solution (50 mL) and an aqueous solution saturated with NaCl (50 mL). The organic phase is dried on $Na_2SO_4$, filtered and concentrated under reduced pressure. A yellow oil of molecule A19 is obtained.

Yield: 4.20 g $^1$H NMR (DMSO-d$_6$, ppm): 0.72-1.02 (9H); 1.08-1.34 (20H); 1.34-2.23 (14H); 2.23-2.35 (3H); 2.42 (2H); 3.01-3.17 (4H); 3.17-3.66 (14H); 4.15-4.44 (2H); 7.53-8.23 (3H); 12.06 (1H).

LC/MS (ESI): 741.5; (calculated ([M+H]$^+$): 741.5).

Example A21: Molecule A21

Molecule 46: Product obtained by SPPS

By means of a similar SPPS method to the one used for the preparation of molecule 41 and applied to TOTA, to N-Fmoc-L-phenylalanine and to molecule A1, an orange oil of molecule 46 is obtained and used without purification.

Yield: 15.07 g (72%)

$^1$H NMR (CDCl_3, ppm): 0.87 (3H); 1.08-1.42 (20H); 1.42-1.62 (2H); 1.62-1.99 (7H); 1.99-2.26 (3H); 2.72 (2H); 2.86 (2H); 2.94-3.72 (18H); 4.20-4.72 (2H); 6.63-7.37 (7H).

LC/MS (ESI): 675.65; (calculated ([M+H]$^+$): 675.5).

Molecule A21

Using a similar method to the one used for the preparation of molecule A19 applied to molecule 46 (13.79 g, 20.43 mmol), a white solid of molecule A21 is obtained.

Yield: 7.56 g (48%)

$^1$H NMR (DMSO-d$_6$, ppm): 0.86 (3H); 1.02-1.42 (21H); 1.42-2.20 (10H); 2.23-2.38 (3H); 2.42 (2H); 2.78-3.18 (6H); 3.23-3.59 (14H); 4.12-4.58 (2H); 7.10-7.30 (5H); 7.53-8.33 (3H); 12.08 (1H).

LC/MS (ESI): 775.5; (calculated ([M+H]$^+$): 775.5).

Example A22: Molecule A22

Using a similar method to the one used for the preparation of molecule A14 applied to molecule A6 (22.15 g, 43.19 mmol), a yellow oil of molecule A22 is obtained.

Yield: 25.19 g (95%)

$^1$H NMR (DMSO-d$_6$, ppm): 0.42-1.51 (33H); 1.51-2.05 (8H); 2.29 (2H); 2.41 (2H); 3.07 (4H); 3.38 (4H); 3.43-3.54 (8H); 7.72 (1H); 7.79 (1H); 12.03 (1H).

LC/MS (ESI): 613.5 (calculated ([M+H]$^+$): 613.5).

Example A23: Molecule A23

Molecule 47: Product obtained by hydrogenating phytol.

To a solution of phytol (30.00 g, 101.20 mmol) in THF (450 mL) in argon is added platinum dioxide (PtO$_2$, 1.15 g, 6.61 mmol). The medium is placed under 1 bar of dihydrogen then stirred for 4 h at ambient temperature. After filtration under celite by rinsing with THF, a black oil of molecule 47 is obtained after concentration under reduced pressure.

Yield: 29.00 g (96%)

$^1$H NMR (CDCl$_3$, ppm): 0.84 (6H); 0.86 (6H); 0.89 (3H); 1.00-1.46 (22H); 1.46-1.68 (3H); 3.61-3.73 (2H).

Molecule 48: Product obtained by oxidizing molecule 47

To a solution of molecule 47 (29.0 g, 97.13 mmol) in a dichloroethane/water mixture (485 mL/388 mL) are added successively tetrabutylammonium bromide (16.90 g, 52.45 mmol), acetic acid (150 mL, 2.62 mol) followed by KMnO$_4$ (46.05 g, 291.40 mmol) in small fractions while maintaining the temperature from 16 to 19° C. The reaction medium is then stirred for 4.5 h at reflux, cooled to 10° C. then acidified to pH 1 with a 6 N HCl solution (20 mL). Na$_2$SO$_3$ (53.90 g) is added progressively while maintaining the temperature at 10° C. and the medium is stirred until completely discolored. Water (200 mL) is added, the phases are separated and the aqueous phase is extracted with DCM (2×400 mL). The combined organic phases are washed with a 10% HCl aqueous solution (20 mL), water (2×200 mL), an aqueous solution saturated with NaCl (200 mL), dried on Na$_2$SO$_4$, filtered and concentrated under reduced pressure. A yellow oil of molecule 48 is obtained after purification by flash chromatography (eluent: cyclohexane, AcOEt).

Yield: 28.70 g (94%)

$^1$H NMR (CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^−$): 311.3).

Molecule 49: Product obtained by coupling molecule 48 and methyl L-prolinate.

Using a similar method to the one used for the preparation of molecule 9 applied to molecule 48 (18.00 g, 57.59 mmol) and to methyl L-prolinate hydrochloride (14.31 g, 86.39 mmol) in DCM (380 mL), a yellow oil of molecule 49 is obtained after washing the organic phase with an aqueous solution saturated with NaHCO$_3$ (2×150 mL), a 10% HCL aqueous solution (2×150 mL), an aqueous solution saturated with NaCl (2×150 mL), followed by drying on Na$_2$SO$_4$, filtration and concentration under reduced pressure.

Yield: 23.20 g (95%)

$^1$H NMR (DMSO-d$_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule 50: Product obtained by saponifying molecule 49.

Using a similar method to the one used for the preparation of molecule 17 applied to molecule 49 (21.05 g, 49.68 mmol), a yellow oil of molecule 50 is obtained.

Yield: 20.40 g (99%)

$^1$H NMR (DMSO-d$_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule 51: Product obtained by coupling molecule 50 and Boc-1-amino-4,7,10-trioxa-13-tridecane amine.

Using a similar method to the one used for the preparation of molecule 9 applied to molecule 50 (8.95 g, 21.85 mmol) and to TOTA (8.40 g, 26.21 mmol), a colorless oil of molecule 51 is obtained after purification by flash chromatography (eluent: DCM, AcOEt, methanol).

Yield: 10.08 g (65%)

$^1$H NMR (DMSO-d$_6$, ppm): 0.78-0.89 (15H); 0.97-1.43 (29H); 1.43-1.55 (1H); 1.55-1.66 (4H); 1.71-2.30 (7H); 2.95 (2H); 3.00-3.19 (2H); 3.34-3.58 (14H); 4.17-4.29 (1H); 6.30-6.79 (1H); 7.67 (0.65H); 8.00 (0.35H).

LC/MS (ESI): 712.6 (calculated ([M+H]$^+$): 712.6).

Molecule 52: Product obtained by hydrolyzing molecule 42 with hydrochloric acid

Using a similar method to the one used for the preparation of molecule A5 applied to molecule 51 (10.08 g, 14.16 mmol), the residue obtained after concentration under reduced pressure is solubilized in DCM (200 mL). The organic phase is washed with a 2 N NaOH aqueous solution (2×100 mL), dried on Na$_2$SO$_4$, filtered and concentrated under reduced pressure. A colorless oil of molecule 52 in neutral amine form is obtained.

Yield: 8.23 g (95%)

$^1$H NMR (DMSO-d$_6$, ppm): 0.78-0.89 (15H); 0.97-1.43 (20H); 1.43-1.69 (6H); 1.69-2.30 (8H); 2.56 (2H); 2.99-3.19 (2H); 3.31-3.58 (14H); 4.15-4.29 (1H); 7.70 (0.65H); 8.04 (0.35H).

LC/MS (ESI): 612.5 (calculated ([M+H]+): 612.5).

Molecule A23

Using a similar method to the one used for the preparation of molecule A14 applied to molecule 52 (15.40 g, 25.17 mmol), a yellow oil of molecule A23 is obtained.

Yield: 15.19 g (85%)

$^1$H NMR (DMSO-d$_6$, ppm): 0.76-0.91 (15H); 0.98-2.26 (32H); 2.29 (2H); 2.41 (2H); 2.98-3.18 (4H); 3.32-3.63 (14H); 4.15-4.29 (1H); 7.68 (0.7H); 7.78 (1H); 8.01 (0.3H); 12.02 (1H).

LC/MS (ESI): 712.5 (calculated ([M+H]$^+$): 712.5).

Example A26: Molecule A26

Molecule 55: Product obtained by SPPS

Molecule 55 is obtained by means of the conventional solid phase peptide synthesis (SPPS) method on 2-chlorotrityl chloride (CTC) resin (47.56 g, 0.74 mmol/g).

The grafting of the first amino acid Fmoc-Glu(OtBu)-OH (2.5 equivalents) is performed in DCM (10 V), in the presence of DIPEA (5.0 equivalents). The unreacted sites are capped with methanol (0.8 mL/g resin) at the end of the reaction.

The protected amino acids Fmoc-Glu(OtBu)-OH (1.5 equivalents (×2)) and molecule A1 (1.5 equivalents) are coupled in DMF (10 V), in the presence of HATU (1.0 equivalent with respect to the acid) and DIPEA (2.0 equivalents with respect to the acid).

The protecting groups Fmoc are removed using an 80:20 DMF/piperidine solution (10 V).

The product is cleaved from the resin using an 80:20 DCM/HFIP solution (10 V).

After concentration under reduced pressure, two co-evaporations are performed on the residue with dichloromethane followed by diisopropylether. The product is purified by silica gel chromatography (dichloromethane, methanol). A colorless gum of molecule 55 is obtained.

Yield: 21.4 g (69% in 8 stages)

$^1$H NMR (DMSO-d6, ppm): 0.85 (3H); 1.16-1.30 (20H); 1.34-1.41 (27H); 1.41-1.53 (2H); 1.67-2.33 (18H); 3.26-3.60 (2H); 4.09-4.44 (4H); 7.73 (0.65H); 7.85 (0.65H); 7.93-8.04 (1H); 8.17 (0.35H); 8.27 (0.35H); 12.64 (1H).

LC/MS (ESI+): 881.7 (calculated ([M+H]$^+$): 881.6).

Molecule 56: Product obtained by the reaction between molecule 55 and 2-phthalimido ethylamine.

Using a similar method to the one used for the preparation of molecule 9 applied to molecule 55 (21.38 g, 24.26 mmol) and to 2-phthalimido ethylamine hydrochloride (HCl.PhthalEDA, 6.60 g, 29.12 mmol) in DCM and in the presence of DIPEA (5.07 mL, 29.12 mmol), a beige foam of molecule 56 is obtained without purification.

Yield: 25.56 g (100%)

$^1$H NMR (DMSO-d6, ppm): 0.85 (3H); 1.17-1.30 (20H); 1.34-1.41 (27H); 1.41-1.52 (2H); 1.56-2.32 (18H); 3.18-3.69 (6H); 4.01-4.43 (4H); 7.64-8.30 (8H).

LC/MS (ESI): 1053.8; (calculated ([M+H]$^+$): 1053.6).

Molecule A26

Molecule 56 (25.56 g, 24.26 mmol) is solubilized in a solution of 40% methylamine in MeOH (242.5 mL, 2.38 mol) at 4° C. then the mixture is stirred at ambient temperature for 5 h. Silica is added to the reaction medium then the mixture is concentrated under reduced pressure. The residue is purified by silica gel chromatography (solid deposition, dichloromethane, methanol, NH3) to produce molecule A26 in the form a pale yellow gum. This product is solubilized in DCM (250 mL) then the solution is washed with a 10% HCl aqueous solution. The aqueous phase is extracted with DCM (100 mL). The combined organic phases are dried on Na2SO4, filtered then concentrated under reduced pressure to produce the hydrochloride of molecule A26 in the form of a white solid.

Yield: 13.5 g (58%)

$^1$H NMR (DMSO-d6, ppm): 0.85 (3H); 1.18-1.30 (20H); 1.34-1.42 (27H); 1.42-1.53 (2H); 1.66-2.02 (9H); 2.02-2.39 (9H); 2.79-2.91 (2H); 3.25-3.64 (4H); 4.08-4.46 (4H); 7.68-8.37 (7H).

LC/MS (ESI): 923.8; (calculated ([M+H]$^+$): 923.6).

Example A27: Molecule A27

Molecule A27 is obtained by means of the conventional solid phase peptide synthesis (SPPS) method on 2-chlorotrityl chloride (CTC) resin (24.00 g, 1.37 mmol/g).

The grafting of the first amino acid Fmoc-6-aminohexanoic acid (1.5 equivalents) is performed in DCM (10 V), in the presence of DIPEA (2.5 equivalents). The unreacted sites are capped with methanol (0.8 mL/g resin) at the end of the reaction.

The protected amino acid Fmoc-Glu-OMe (1.5 equivalents) and palmitic acid (1.5 equivalents) are coupled in DMF (10 V), in the presence of HATU (1.0 equivalent with respect to the acid) and DIPEA (1.5 equivalents with respect to the acid).

The protecting groups Fmoc are removed using an 80:20 DMF/piperidine solution (10 V).

The product is cleaved from the resin using an 80:20 DCM/HFIP solution (10 V).

After concentration under reduced pressure, two co-evaporations are performed on the residue with dichloromethane followed by toluene. The product is purified by recrystallization in ethyl acetate. A white solid of molecule A27 is obtained.

Yield: 11.54 g (68% in 6 stages)

$^1$H NMR (CDCl$_3$, ppm): 0.88 (3H); 1.19-1.35 (24H); 1.35-1.44 (2H); 1.50-1.70 (6H); 1.91-2.01 (1H); 2.14-2.40 (7H); 3.14-3.34 (2H); 3.75 (3H); 4.51-4.59 (1H); 6.53 (1H); 6.70 (1H).

LC/MS (ESI+): 513.4 (calculated ([M+H]$^+$): 513.4).

Part B—Hydrophobic Co-Polyamino Acid Synthesis

| # | CO-POLYAMINO ACIDS BEARING CARBOXYLATE CHARGES AND HYDROPHOBIC RADICALS |
|---|---|
| B1 | [Chemical structure: polyamino acid with NaO-C(=O) glutamate-type repeat units, R$_1$-NH and NH-R$_1$ end groups, connected via ethylenediamine linker, with subscripts m and n]<br>i = 0.050, DP (m + n) = 40<br>R$_1$ = H, pyroglutamate or<br>[Chemical structure: palmitoyl-prolyl group with * indicating attachment point] |

-continued
| # | CO-POLYAMINO ACIDS BEARING CARBOXYLATE CHARGES AND HYDROPHOBIC RADICALS |
|---|---|
| B2 | 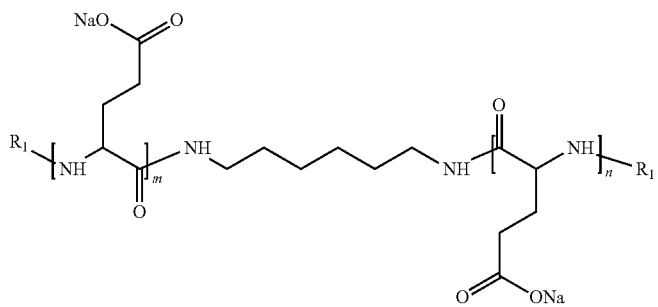<br>i = 0.0657, DP (m + n) = 30<br>$R_1$ = H, pyroglutamate or<br>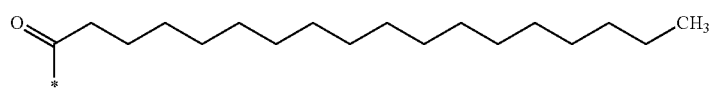 [SMILES: *C(=O)CCCCCCCCCCCCCCCCC] |
| B3 | 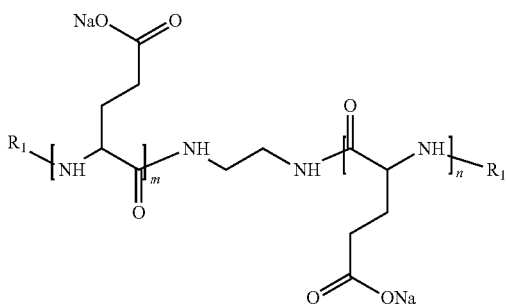<br>i = 0.0808, DP (m + n) = 24<br>$R_1$ = H, pyroglutamate or<br>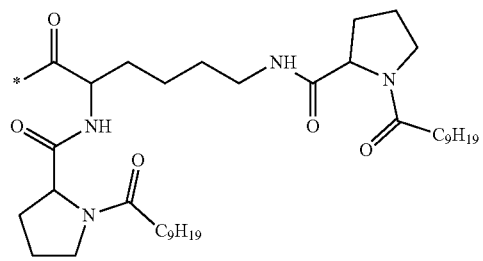 |
| B4 | 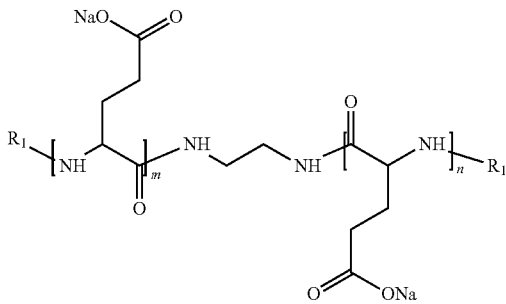<br>i = 0.134, DP (m + n) = 14<br>$R_1$ = H, pyroglutamate or |

-continued
| # | CO-POLYAMINO ACIDS BEARING CARBOXYLATE CHARGES AND HYDROPHOBIC RADICALS |
|---|---|
| | 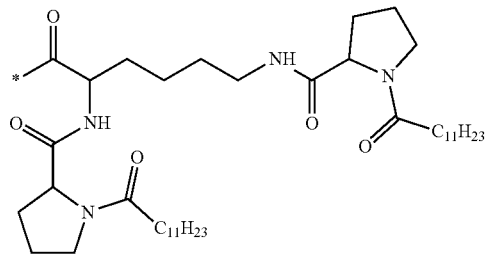 |
| B5 | 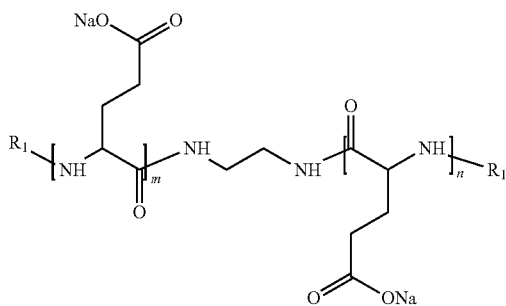
i = 0.077, DP (m + n) = 24
$R_1$ = H, pyroglutamate or
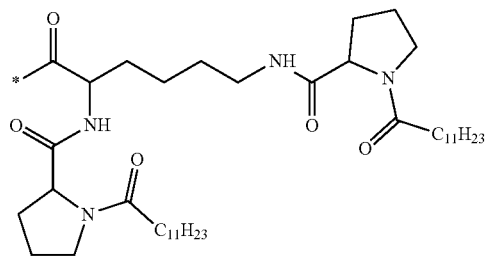 |
| B6 | 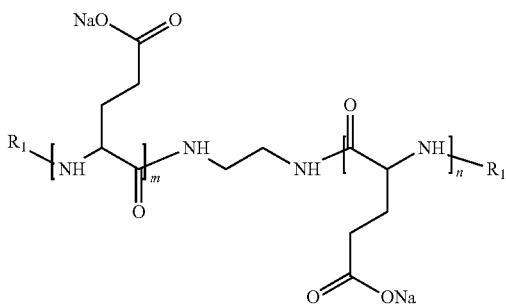
i = 0.0812, DP (m + n) = 24
$R_1$ = H, pyroglutamate or
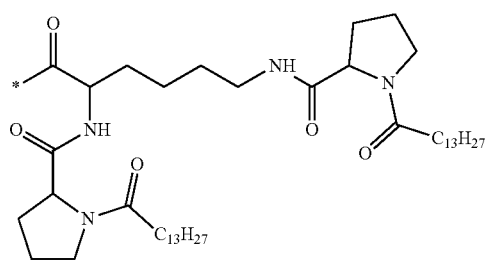 |

| # | CO-POLYAMINO ACIDS BEARING CARBOXYLATE CHARGES AND HYDROPHOBIC RADICALS |
|---|---|
| B9 | 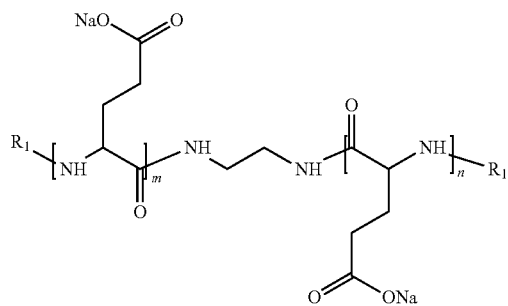<br>$i = 0.0833$, DP $(m + n) = 24$<br>$R_1 =$ H, pyroglutamate or<br>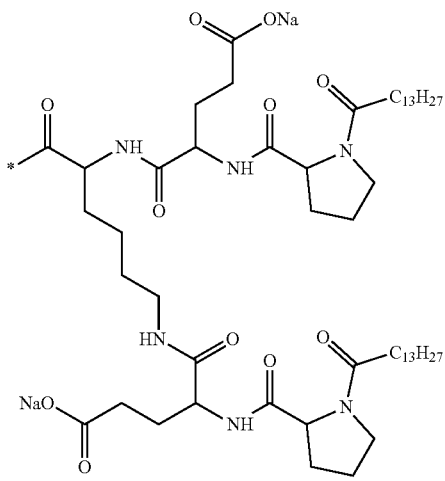 |
| B13 | $i = 0.079$, DP $(m + n) = 24$<br>$R_1 =$ H, pyroglutamate or |

| # | CO-POLYAMINO ACIDS BEARING CARBOXYLATE CHARGES AND HYDROPHOBIC RADICALS |
|---|---|
| B14 | 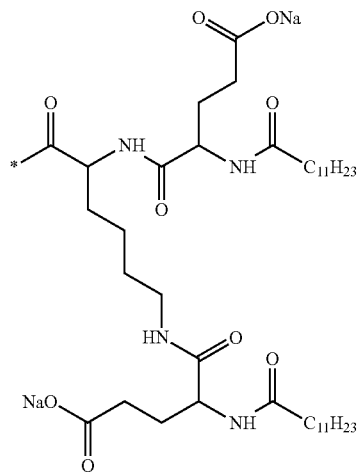 |
| | 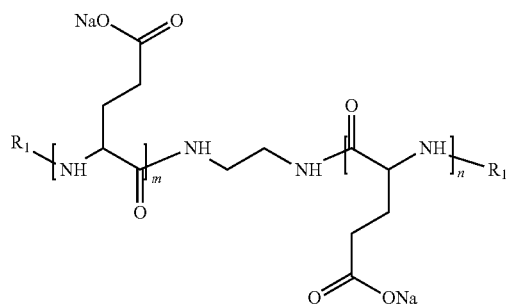
i = 0.072, DP (m + n) = 24
R₁ = H, pyroglutamate or
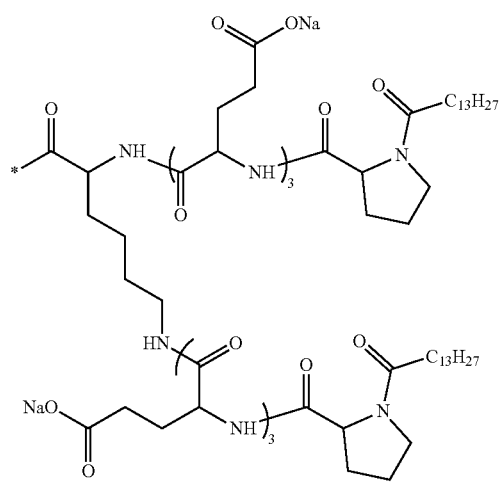 |

-continued
| # | CO-POLYAMINO ACIDS BEARING CARBOXYLATE CHARGES AND HYDROPHOBIC RADICALS |
|---|---|
| B15 | 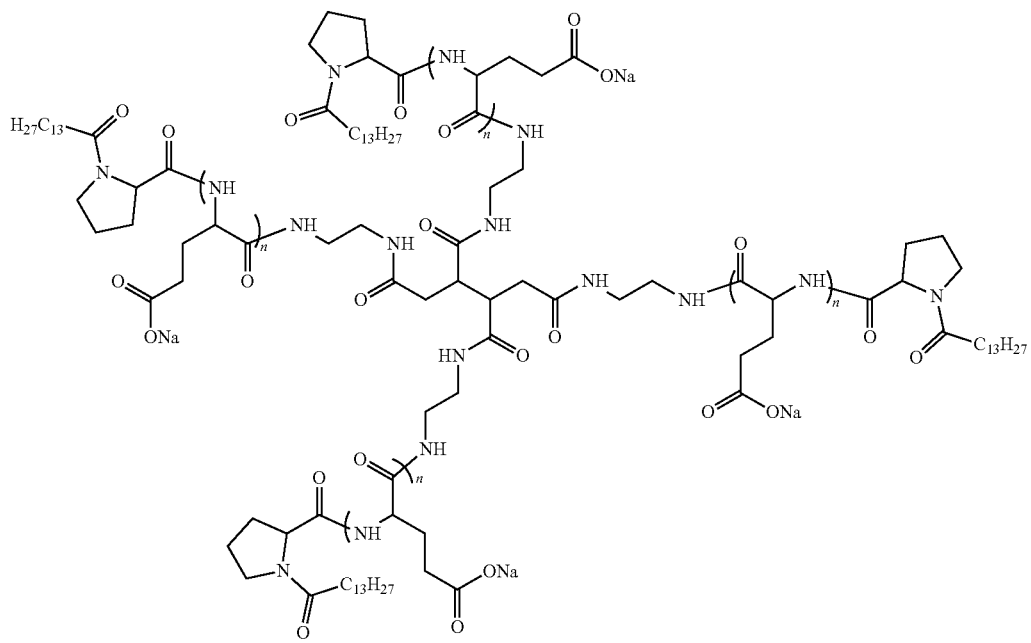<br>DP (n) = 5.5<br>i = 3.4 |
| B16 | 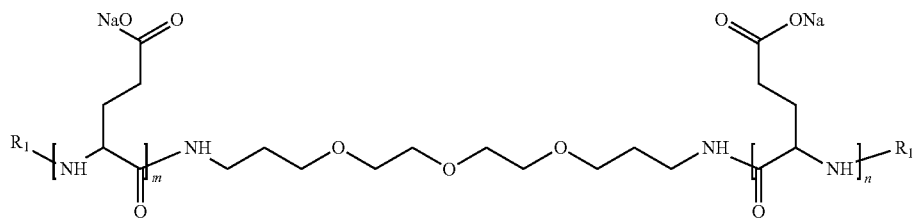<br>i = 0.078, DP (m + n) = 24<br>$R_1$ = H, pyroglutamate or<br>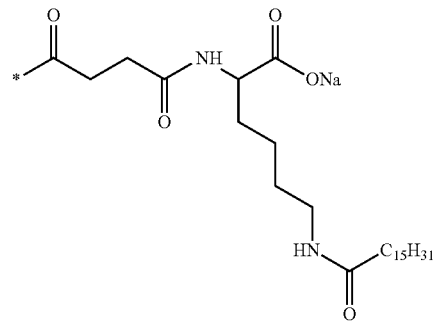 |

| # | CO-POLYAMINO ACIDS BEARING CARBOXYLATE CHARGES AND HYDROPHOBIC RADICALS |
|---|---|
| B17 | 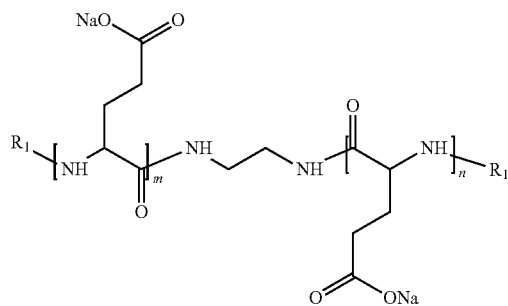<br>i = 0.048, DP (m + n) = 24<br>R₁ = H, pyroglutamate or<br>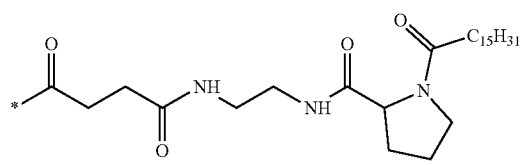 |
| B18 | 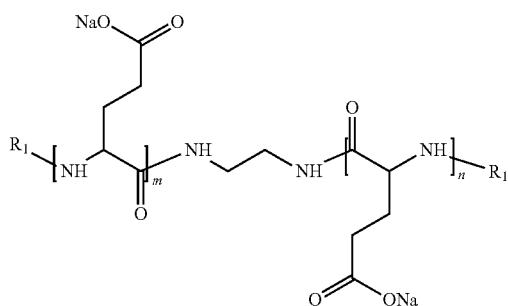<br>i = 0.075, DP (m + n) = 24<br>R₁ = H, pyroglutamate or<br>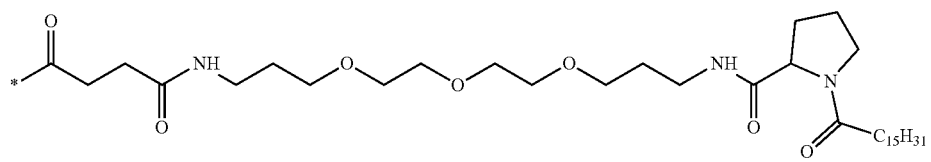 |
| B19 | 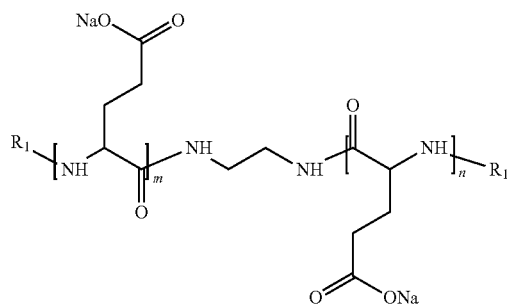<br>i = 0.066, DP (m + n) = 24<br>R₁ = H, pyroglutamate or |

| # | CO-POLYAMINO ACIDS BEARING CARBOXYLATE CHARGES AND HYDROPHOBIC RADICALS |
|---|---|
| | 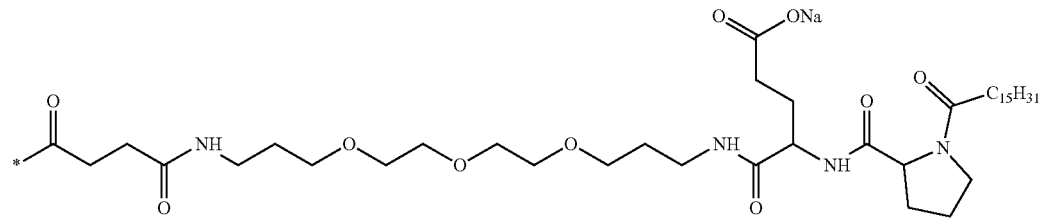 |
| B20 | 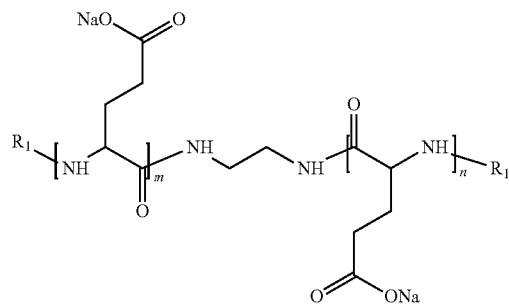
i = 0.075, DP (m + n) = 24
R₁ = H, pyroglutamate or
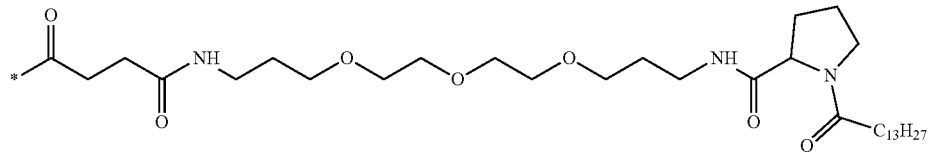 |
| B21 | 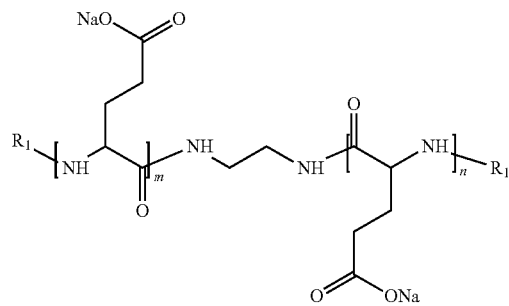
i = 0.077, DP (m + n) = 24
R₁ = H, pyroglutamate or
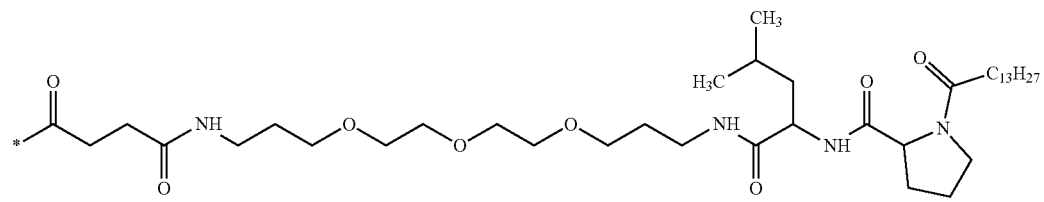 |

| # | CO-POLYAMINO ACIDS BEARING CARBOXYLATE CHARGES AND HYDROPHOBIC RADICALS |
|---|---|
| B23 | 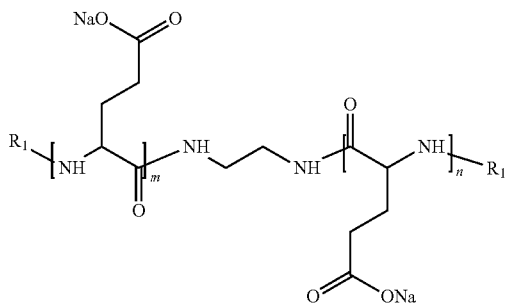 i = 0.080, DP (m + n) = 24<br>$R_1$ = H, pyroglutamate or<br>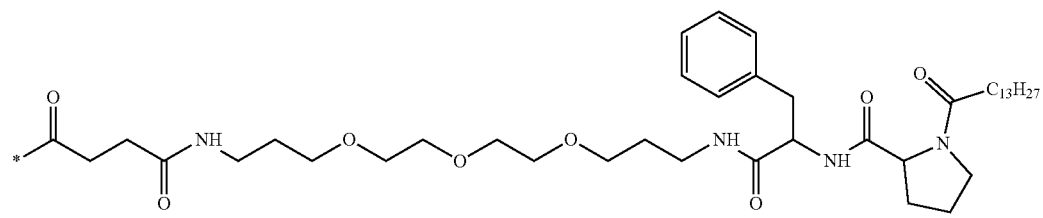 |
| B24 | 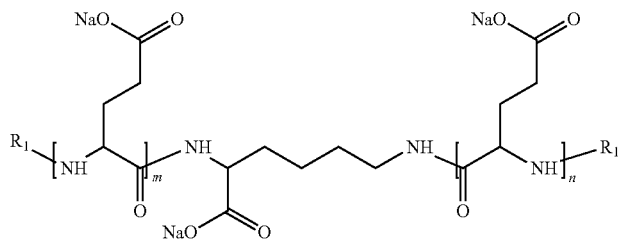 i = 0.143, DP (m + n) = 14<br>$R_1$ = H, pyroglutamate or<br>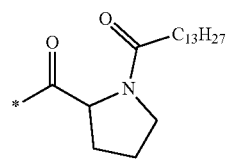 |
| B25 | 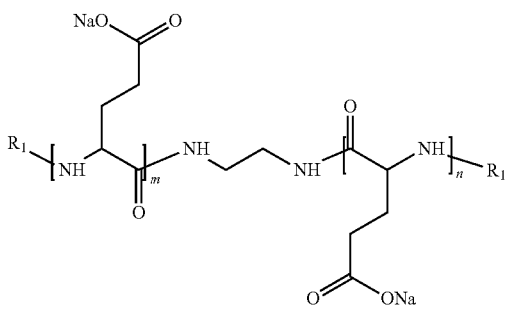 i = 0.079, DP (m + n) = 24<br>$R_1$ = H, pyroglutamate or |

-continued
| # | CO-POLYAMINO ACIDS BEARING CARBOXYLATE CHARGES AND HYDROPHOBIC RADICALS |
|---|---|
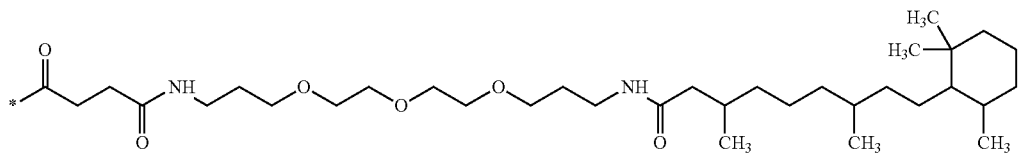 [SMILES: *C(=O)CCC(=O)NCCCOCCOCCOCCCNC(=O)CC(C)CCCC(C)CCC1C(C)CCCC1(C)C]
B26
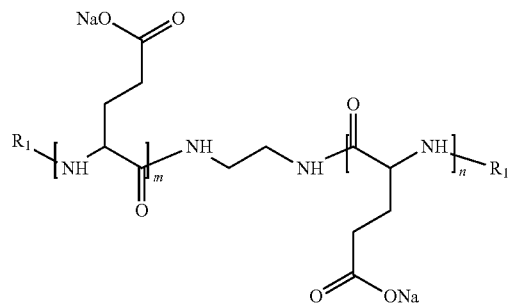
$i = 0.073$, DP $(m + n) = 24$
$R_1$ = H, pyroglutamate or
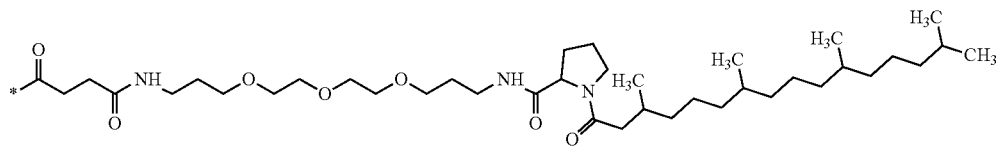 [SMILES: *C(=O)CCC(=O)NCCCOCCOCCOCCCNC(=O)C1CCCN1C(=O)CC(C)CCCC(C)CCCC(C)CCCC(C)C]
B27
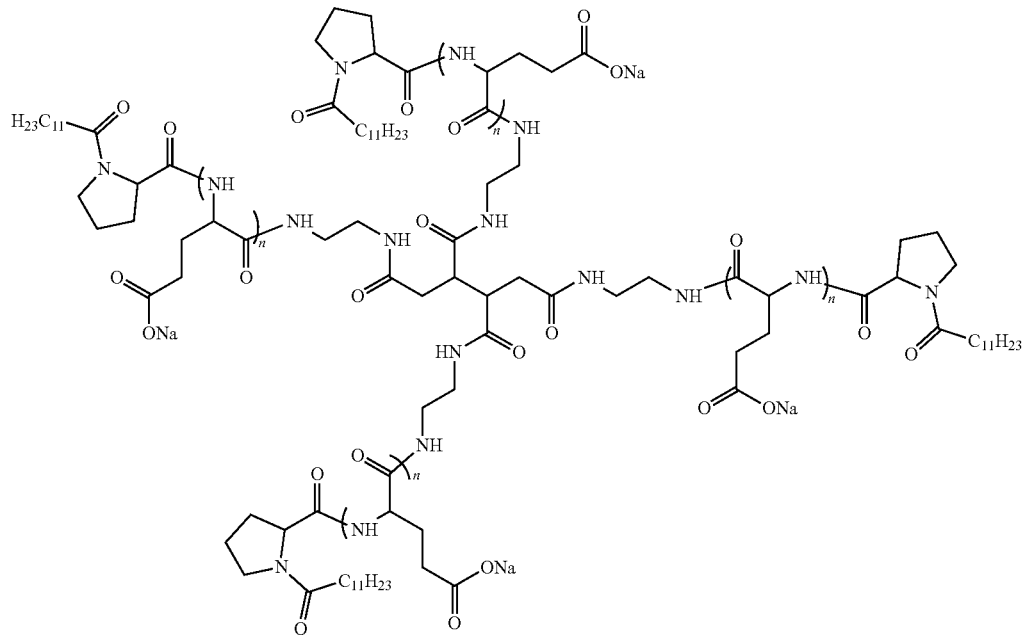
DP $(n) = 4.75$
$i = 3.7$ -continued
| # | CO-POLYAMINO ACIDS BEARING CARBOXYLATE CHARGES AND HYDROPHOBIC RADICALS |
|---|---|
| B28 | 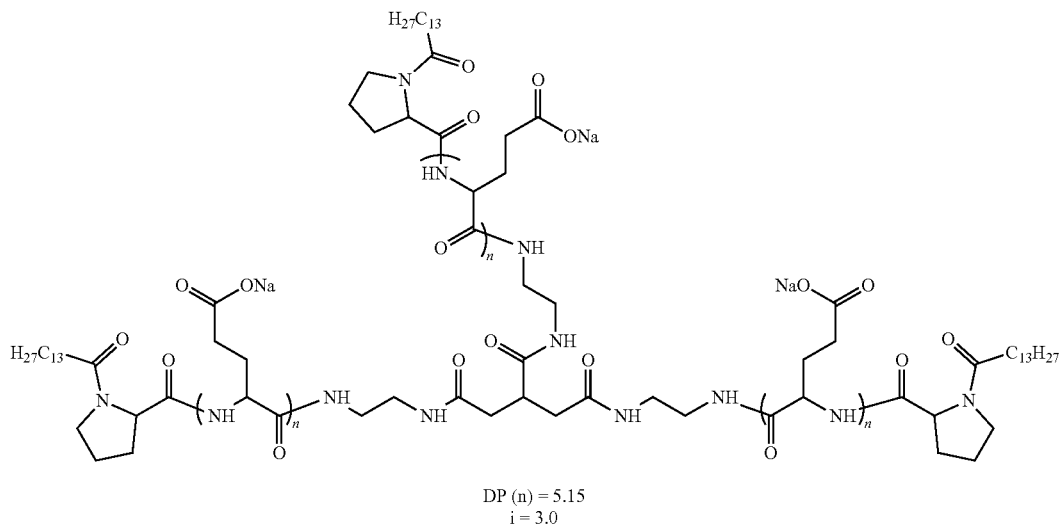 DP (n) = 5.15<br>i = 3.0 |
| B29 | 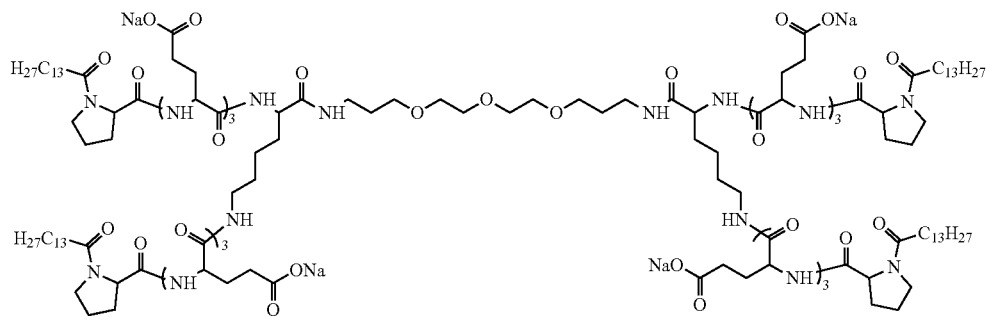 |
| B30 | 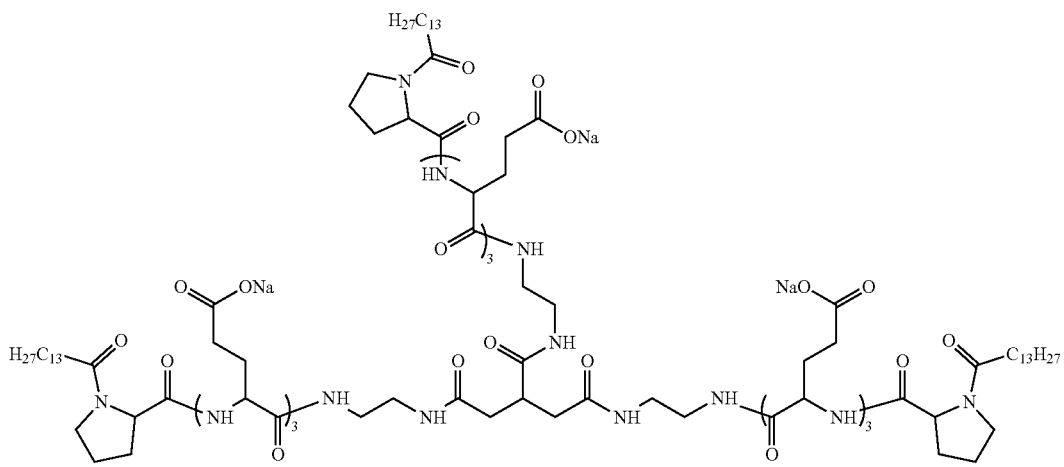 |

| # | CO-POLYAMINO ACIDS BEARING CARBOXYLATE CHARGES AND HYDROPHOBIC RADICALS |
|---|---|
| B31 | 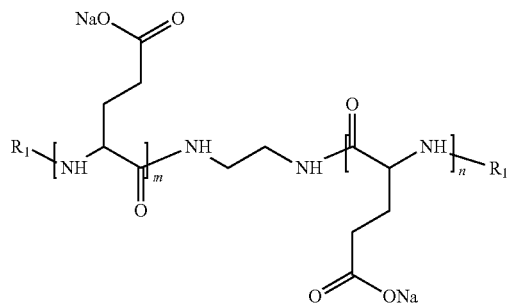<br>i = 0.075, DP (m + n) = 24<br>$R_1$ = H, pyroglutamate or<br>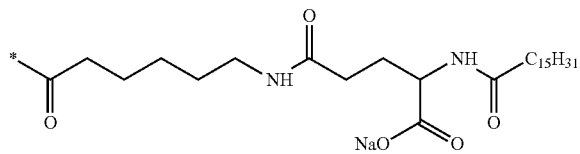 |

Example B1: Co-Polyamino Acid B1—Sodium Poly-L-glutamate Modified at its Extremities by Molecule A1 and having a Number Average Molar Mass (Mn) of 3600 g/mol Co-polyamino acid B1-1: poly-L-benzylglutamate obtained from the polymerization of γ-benzyl-L-glutamate N-carboxyanhydride initiated by ethylenediamine and modified at its extremities by molecule A1.

In an oven-dried flask, γ-benzyl-L-glutamate N-carboxyanhydride (34.74 g, 132 mmol) is solubilized in anhydrous DMF (78 mL). The mixture is then stirred until complete dissolution, cooled to 0° C., then ethylene diamine (0.205 g, 3.41 mmol) is introduced rapidly and the medium is stirred at 0° C.

In parallel, molecule A1 (2.26 g, 6.94 mmol) is solubilized in DMF (44 mL), then NHS (0.82 g, 7.12 mmol) and DCC (1.47 g, 7.12 mmol) are added successively. After stirring overnight at ambient temperature, the heterogeneous mixture is filtered on a sintered filter. The filtrate is then added to the polymer solution kept at 0° C. After 24 h, the solution is placed at ambient temperature. After 6 h of stirring, the reaction medium is poured onto diisopropylether (IPE, 1.8 L). The precipitate is filtered on a sintered filter, washed with IPE (3×30 mL) and dried at 30° C. under reduced pressure.

Co-Polyamino Acid B1

Co-polyamino acid B1-1 is diluted in trifluoroacetic acid (TFA, 132 mL), then the solution is cooled to 4° C. A 33% HBr solution in acetic acid (92.5 mL, 0.528 mol) is then added dropwise. The mixture is stirred at ambient temperature for 2 h, then poured dropwise onto a 1:1 (v/v) mixture of diisopropylether and water under stirring (0.8 L). After 2 h of stirring, the heterogeneous mixture is left to stand overnight. The white precipitate is recovered by filtration, washed with IPE (2×66 mL) then with water (2×66 mL). The solid obtained is then solubilized in water (690 mL) by adjusting the pH to 7 by adding an aqueous solution of 1 N sodium hydroxide. After solubilization, the theoretical concentration is adjusted to 20 g/L theoretical by adding water (310 mL), the solution is filtered on a 0.45 μm filter then purified by ultrafiltration against a 0.9% NaCl solution, followed by water until the conductimetry of the permeate is less than 50 μS/cm. The solution obtained is filtered on a 0.2 μm filter and stored at 2-8° C.

Dry extract: 24.3 mg/g
DP (estimated as per $^1$H NMR): 40
As per $^1$H NMR: i=0.050
The calculated average molar mass of co-polyamino acid B1 is 6719 g/mol.
HPLC-Organic SEC (PEG calibrator): Mn=3600 g/mol.

Example B2: Co-Polyamino Acid B2—Sodium Poly-L-glutamate Modified at its Extremities by Stearic Acid and having a Number Average Molar Mass (Mn) of 3400 g/mol Co-polyamino acid B2-1: poly-L-benzylglutamate obtained from the polymerization of γ-benzyl-L-glutamate N-carboxyanhydride initiated by hexamethylenediamine.

In an previously oven-dried flask, γ-benzyl-L-glutamate N-carboxyanhydride (30.0 g, 114 mmol) is solubilized in anhydrous DMF (67 mL). The mixture is then stirred until complete dissolution, cooled to 0° C., then hexamethylenediamine (0.442 g, 3.8 mmol) is introduced rapidly. After 23 h of stirring at 0° C., a 4 M HCl solution in dioxane (4.7 mL, 18.8 mmol) is added then the reaction medium is poured in 5 min onto a mixture of methanol (94 mL) and IPE (375 mL). The precipitate is filtered on a sintered filter, washed with IPE (2×70 mL) and dried at 30° C. under reduced pressure.

Co-polyamino acid B2-2: poly-L-benzylglutamate modified at its extremities by stearic acid.

To a solution of stearic acid (0.851 g, 2.99 mmol) in DMF (20 mL) at 0° C. are added successively HATU (1.484 g, 3.89 mmol) and DIPEA (1.166 g, 9.02 mmol). The solution is then introduced onto a solution of co-polyamino acid B2-1 (10.0 g) and triethylamine (TEA, 0.309 g, 3.04 mmol) in DMF (110 mL) at 0° C., and the medium is stirred for 18 h from 0° C. to ambient temperature. Dichloromethane (390 mL) is added, the organic phase is washed with 0.1 N HCl aqueous solution (3×190 mL), an aqueous solution saturated with NaHCO$_3$ (2×190 mL), an aqueous solution saturated with NaCl (2×190 mL) followed by water (190 mL). The medium is then poured onto IPE (1.4 L). The precipitate is filtered on a sintered filter, washed with IPE (2×100 mL) and dried at 30° C. under reduced pressure.

Co-Polyamino Acid B2

Using a similar method to the one used for the preparation of co-polyamino acid B1 applied to co-polyamino acid B2-2 (8.80 g, 36.5 mmol), a sodium poly-L-glutamate modified at its extremities with stearic acid is obtained.

Dry extract: 17.9 mg/g
DP (estimated as per $^1$H NMR): 30
As per $^1$H NMR: i=0.0657

The calculated average molar mass of co-polyamino acid B2 is 5174 g/mol.

HPLC-Organic SEC (PEG calibrator): Mn=3400 g/mol.

Example B3: Co-polyamino Acid B3—Sodium Poly-L-glutamate Modified at its Extremities by Molecule A2 and having a Number Average Molar Mass (Mn) of 3000 g/mol Co-polyamino acid B3-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylene diamine (0.765 g, 12.73 mmol) and to γ-benzyl-L-glutamate N-carboxyanhydride (80.0 g, 304 mmol), co-polyamino acid B3-1 is obtained.

Co-polyamino acid B3-2: poly-L-benzylglutamate modified at its extremities by A2.

Using a similar method to the one used for the preparation of co-polyamino acid B2-2 applied to co-polyamino acid B3-1 (30.0 g, 5.56 mmol) and to molecule A2 (7.94 g, 12.24 mmol), a poly-L-benzylglutamate modified at its extremities with molecule A2 is obtained.

Co-Polyamino Acid B3

To a solution of co-polyamino acid B3-2 (36.6 g, 133.5 mmol) in N,N-dimethylacetamide (DMAc, 146 mL) is added 5% palladium on alumina (7.3 g), then the solution is placed at 60° C. at 10 bar of hydrogen. After leaving overnight, the reaction medium is filtered on a sintered filter then on a 0.2 µm PTFE filter. The filtrate is then placed under stirring before adding water (1.4 L) previously acidified to pH 2 with a 1 N HCl solution (14 mL) dropwise. After overnight, the precipitate is filtered on a sintered filter, washed with water (4×110 mL) and dried at 30° C. under reduced pressure.

The solid obtained is then solubilized in water (1.09 L) by adjusting the pH to 7 by adding an aqueous solution of 1 N sodium hydroxide (121 mL). After solubilization, the solution is basified by adding 1 N sodium hydroxide (26 mL) up to pH 12. After 2 h, the solution is neutralized by adding 1 N HCl solution (28 mL). The theoretical concentration is adjusted to 12 g/L theoretical by adding water (650 mL) and ethanol (1040 mL) then the solution is filtered on an R53SLP carbon filter (3M) at a rate of 12 mL/min, then on a 0.2 µm PES filter. The solution is then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 21.6 mg/g
DP (estimated as per $^1$H NMR): 24
As per $^1$H NMR: i=0.0808

The calculated average molar mass of co-polyamino acid B3 is 4948 g/mol.

HPLC-Organic SEC (PEG calibrator): Mn=3000 g/mol.

Example B4: Co-Polyaminoacid B4—Sodium Poly-L-glutamate Modified at its Extremities by Molecule A3 and having a Number Average Molar Mass (Mn) of 2500 g/mol Co-polyamino Acid B4-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylene diamine (1.644 g, 27.35 mmol) and to γ-benzyl-L-glutamate N-carboxyanhydride (100.0 g, 380 mmol), co-polyamino acid B4-1 is obtained.

Co-polyamino acid B4-2: poly-L-benzylglutamate modified at its extremities by molecule A3.

Using a similar method to the one used for the preparation of co-polyamino acid B2-2 applied to co-polyamino acid B4-1 (10.0 g, 3.12 mmol) and to molecule A3 (4.412 g, 6.26 mmol), a poly-L-benzylglutamate modified at its extremities with molecule A3 is obtained.

Co-Polyamino Acid B4

Using a similar method to the one used for the preparation of co-polyamino acid B3 applied to co-polyamino acid B4-2 (12.0 g, 37.3 mmol), a sodium poly-L-glutamate modified at its extremities with molecule A3 is obtained.

Dry extract: 21.7 mg/g
DP (estimated as per $^1$H NMR): 14
As per $^1$H NMR: i=0.134

The calculated average molar mass of co-polyamino acid B4 is 3464 g/mol.

HPLC-Organic SEC (PEG calibrator): Mn=2500 g/mol.

Example B5: Co-polyamino Acid B5—Sodium Poly-L-glutamate Modified at its Extremities by Molecule A3 and having a Number Average Molar Mass (Mn) of 2800 g/mol Co-polyamino acid B5-1: poly-L-benzylglutamate obtained from the polymerization of γ-benzyl-L-glutamate N-carboxyanhydride initiated by Ethylenediamine.

Using a similar method to the one used for the preparation of co-polyamino acid B2-1 applied to ethylene diamine (0.95 g, 15.83 mmol) and to γ-benzyl-L-glutamate N-carboxyanhydride (100.0 g, 380 mmol), co-polyamino acid B5-1 is obtained.

Co-polyamino acid B5-2: Poly-L-benzylglutamate modified at its extremities by molecule A3.

Using a similar method to the one used for the preparation of co-polyamino acid B2-2 applied to co-polyamino acid B5-1 (20.0 g, 3.71 mmol) and to molecule A3 (5.233 g, 7.42 mmol), a poly-L-benzylglutamate modified at its extremities with molecule A3 is obtained.

Co-Polyamino Acid B5

Using a similar method to the one used for the preparation of co-polyamino acid B1 applied to co-polyamino acid B5-2 (15.6 g, 55.93 mmol), a sodium poly-L-glutamate modified at its extremities with molecule A3 is obtained.

Dry extract: 27.4 mg/g
DP (estimated as per $^1$H NMR): 24
As per $^1$H NMR: i=0.077

The calculated average molar mass of co-polyamino acid B5 is 4956 g/mol.

HPLC-Organic SEC (PEG calibrator): Mn=2800 g/mol.

Example B6: Co-polyamino Acid B6: Sodium poly-L-glutamate Modified at its Extremities by Molecule A4 and having a Number Average Molar Mass (Mn) of 2900 g mol Co-polyamino Acid B6-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylene diamine (0.951 g, 15.83 mmol) and to γ-benzyl-L-glutamate N-carboxyanhydride (100.0 g, 380 mmol), co-polyamino acid B6-1 is obtained.

Co-polyamino acid B6-2: poly-L-benzylglutamate modified at its extremities by molecule A4.

Using a similar method to the one used for the preparation of co-polyamino acid B2-2 applied to co-polyamino acid B6-1 (20.0 g, 3.71 mmol) and to molecule A4 (6.649 g, 8.74 mmol), a poly-L-benzylglutamate modified at its extremities with molecule A4 is obtained.

Co-Polyamino Acid B6

Using a similar method to the one used for the preparation of co-polyamino acid B1 applied to co-polyamino acid B6-2 (19.7 g, 69.47 mmol), a sodium poly-L-glutamate modified at its extremities with molecule A4 is obtained.

Dry extract: 28.7 mg/g
DP (estimated as per $^1$H NMR): 24
As per $^1$H NMR: i=0.0812

The calculated average molar mass of co-polyamino acid B6 is 5135 g/mol.

HPLC-Organic SEC (PEG calibrator): Mn=2900 g/mol.

Example B9: Co-polyamino acid B9—Sodium Poly-L-glutamate Modified at its Extremities by Molecule A7 wherein the Side Chains are Deprotected and having a Number Average Molar Mass (Mn) of 3200 g/mol Co-polyamino acid B9-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylene diamine (0.96 g, 15.94 mmol) and to γ-benzyl-L-glutamate N-carboxyanhydride (100.0 g, 380 mmol), co-polyamino acid B9-1 is obtained.

Co-polyamino acid B9-2: poly-L-benzylglutamate modified at its extremities by molecule A7.

Using a similar method to the one used for the preparation of co-polyamino acid B2-2 applied to co-polyamino acid B9-1 (25.0 g, 4.64 mmol) and to molecule A7 (10.49 g, 9.27 mmol), a poly-L-benzylglutamate modified at its extremities with molecule A7 is obtained.

Co-polyamino acid B9-3: poly-L-benzylglutamate modified at its extremities by molecule A7 wherein the side chains are deprotected.

Co-polyamino acid B9-2 (18.6 g) is solubilized in TFA (100 mL). After 2 h under stirring, the reaction medium is concentrated under reduced pressure.

Co-Polyamino Acid B9

Using a similar method to the one used for the preparation of co-polyamino acid B3 applied to co-polyamino acid B9-3 (18.0 g, 59.0 mmol), a sodium poly-L-glutamate modified at its extremities with molecule A7 is obtained.

Dry extract: 21.8 mg/g
DP (estimated as per $^1$H NMR): 24
As per $^1$H NMR: i=0.0833

The calculated average molar mass of co-polyamino acid B9 is 5776 g/mol.

HPLC-Organic SEC (PEG calibrator): Mn=3200 g/mol.

Example B13: Co-polyamino Acid B13—Sodium Poly-L-glutamate Modified at its Extremities by Molecule A11 wherein the Esters are Deprotected and having a Number Average Molar Mass (Mn) of 3200 g/mol Co-polyamino acid B13-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylene diamine (4.76 g, 15.94 mmol) and to γ-benzyl-L-glutamate N-carboxyanhydride (500.0 g, 1900 mmol), co-polyamino acid B13-1 is obtained.

Co-polyamino acid B13-2: poly-L-benzylglutamate modified at its extremities by molecule A11.

To a solution of co-polyamino acid B13-1 (12.0 g) in DMF (40 mL) at 0° C. are successively added a solution of molecule A11 (5.88 g, 6.67 mmol) in DMF (20 mL), N-2-hydroxypyridine oxide (HOPO, 0.82 g, 7.34 mmol), N-(3-dimethylaminopropyl)-N'-ethylcarbodiimide (EDC) (1.66 g, 8.68 mmol), followed by DIPEA (0.97 mL, 5.56 mmol). The reaction medium is stirred at 0° C. for 16 h and at 20° C. for 2 h. Dichloromethane (150 mL) is added and the organic phase is washed with a 0.1 N HCl aqueous solution (6×75 mL), dried on $Na_2SO_4$ then filtered. The organic phase is then poured onto IPE (600 mL), then left to stand for 18 h. The white precipitate is recovered by filtration, washed with IPE (2×150 mL) then dried under reduced pressure at 30° C.

Co-polyamino acid B13-3: poly-L-benzylglutamate modified at its extremities by molecule A11 wherein the esters are deprotected Co-polyamino acid B13-2 is solubilized in TFA (60 mL), and the solution is stirred for 2 h at ambient temperature then is poured dropwise onto diisopropylether under stirring (600 mL). After 18 h, the white precipitate is recovered by filtration, triturated with IPE and dried under reduced pressure.

Co-Polyamino Acid B13

Using a similar method to the one used for the preparation of co-polyamino acid B3 applied to co-polyamino acid B13-3 (14.5 g), a sodium poly-L-glutamate modified at its extremities with molecule A11 wherein the esters are deprotected is obtained.

Dry extract: 18.0 mg/g
DP (estimated as per $^1$H NMR): 24
As per $^1$H NMR: i=0.079

The calculated average molar mass of co-polyamino acid B13 is 5194 g/mol.

HPLC-Organic SEC (PEG calibrator): Mn=3200 g/mol

Example B14: Co-polyamino Acid B14—Sodium poly-L-glutamate Modified at its Extremities by Molecule A12 wherein the Esters are Deprotected and having a Number Average Molar Mass (Mn) of 3700 g/mol Co-polyamino acid B14-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylene diamine (4.76 g, 15.94 mmol) and to γ-benzyl-L-glutamate N-carboxyanhydride (500.0 g, 1900 mmol), co-polyamino acid B14-1 is obtained.

Co-polyamino acid B14-2: poly-L-benzylglutamate modified at its extremities by molecule A12

Using a similar method to the one used for the preparation of co-polyamino acid B2-2 applied to molecule A12 (2.67 g, 1.43 mmol) and to co-polyamino acid B14-1 (3.5 g), a poly-L-benzylglutamate modified at its two extremities with molecule A2 is obtained.

Co-polyamino acid B14-3: poly-L-benzylglutamate modified at its extremities by molecule A12 wherein the esters are deprotected Using a similar method to the one used for the preparation of co-polyamino acid B13-3 applied to co-polyamino acid B14-2, a poly-L-benzylglutamate modified at its two extremities with molecule A12 wherein the esters are deprotected is obtained.

Co-Polyamino Acid B14

Using a similar method to the one used for the preparation of co-polyamino acid B3 applied to co-polyamino acid B14-3 (1.97 g), in a hydrogen atmosphere (1 atm, 48 h, 65° C.), a sodium poly-L-glutamate modified at its two extremities with molecule A12 wherein the esters are deprotected is obtained.

Dry extract: 13.2 mg/g
DP (estimated as per $^1$H NMR): 24
As per $^1$H NMR: i=0.072
The calculated average molar mass of co-polyamino acid B14 is 6537 g/mol.
HPLC-Organic SEC (PEG calibrator): Mn=3700 g/mol Example B15: Co-polyamino Acid B15—Butyltetracarboxylic Acid Substituted with Molecule A13 wherein the Esters are Deprotected and having a Number Average Molar Mass (Mn) of 2700 g/mol Molecule A13

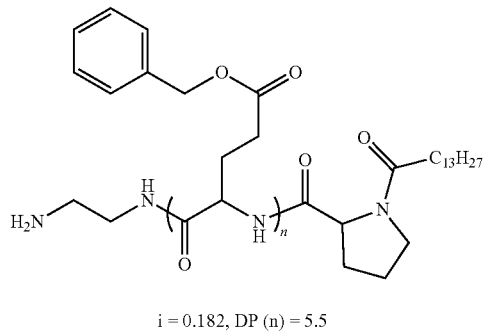

i = 0.182, DP (n) = 5.5

Molecule 31: Product obtained by polymerization of γ-benzyl-L-glutamate N-carboxyanhydride initiated by N-Boc-ethylenediamine.

A solution of BocEDA (12.00 g, 74.9 mmol) in DMF (12 mL) is prepared. In a reaction vessel, γ-benzyl-L-glutamate N-carboxyanhydride (78.87 g, 300.0 mmol) is solubilized in DMF (165 mL) at 25° C. The mixture is then stirred until complete dissolution, cooled to −10° C., then the BocEDA solution is introduced rapidly. The reaction medium is stirred at 0° C. for 4 h then a solution of HCl in 1,4-dioxane (3.33 M, 19.8 mL, 65.34 mmol) is added. The reaction medium is stirred at ambient temperature then the solution is poured onto a solution of MeOH/IPE (245 mL/990 mL) cooled by an ice bath. After 62 h of stirring at ambient temperature, the white precipitate is filtered on a sintered filter, washed with IPE (2×160 mL) and dried at 30° C. under reduced pressure.

$^1$H NMR (DMSO-d6, ppm): 1.35 (9H); 1.70-2.10 (10H); 2.26-2.65 (10H); 2.85-3.18 (4H); 3.85 (1H); 4.14-4.42 (4H); 4.87-5.24 (10H); 6.34-6.86 (1H); 7.11-7.56 (25H); 7.90-8.44 (7H); 8.69 (1H).
DP (estimated as per $^1$H NMR): 5.0
The calculated average molar mass of molecule 31 in hydrochloride salt form is 1292.9 g/mol.

Molecule 32: Product obtained by coupling molecule 31 and molecule A1.

Molecule 31 (10.0 g, 7.73 mmol) is solubilized in a mixture of DCM (90 mL) and DIPEA (1.585 g, 9.32 mmol) at 0° C. To this solution are added successively HOPO (1.242 g, 11.18 mmol), molecule A1 (3.335 g, 10.25 mmol) and EDC (2.141 g, 11.17 mmol). After stirring overnight, the reaction medium is washed twice with a 0.1 N HCl solution (2×100 mL), twice with a 5% Na$_2$CO$_3$ aqueous solution (2×100 mL) followed by a saturated NaCl solution (100 mL). The organic phase is dried on Na$_2$SO$_4$, filtered and concentrated under reduced pressure. The residue is solubilized in DCM (30 mL) and the solution is poured onto isopropyl alcohol (600 mL) under stirring at 0° C. The precipitate formed is recovered by vacuum filtration then dried under vacuum at 30° C.

Yield: 7.58 g (62%)
$^1$H NMR (CDCl$_3$, ppm): 0.87 (3H); 1.06-2.76 (58.6H); 3.06-4.45 (12.4H); 4.88-5.25 (10.8H); 5.72-8.40 (34.4H).
DP (estimated as per $^1$H NMR): 5.4
The calculated average molar mass of molecule 32 in hydrochloride salt form is 1651.6 g/mol.

Molecule A13

After solubilizing molecule 32 (5.93 g, 3.59 mmol) in DCM (40 mL), the solution is cooled to 0° C. and TFA (40 mL) is added. The reaction medium is stirred at 0° C. for 3 h then is dry concentrated under reduced pressure at ambient temperature. The residue is taken up in DCM (120 mL) and washed with an aqueous carbonate buffer solution at pH 10.4 (3×240 mL) then by a 0.1 N HCl aqueous solution (2×240 mL). The organic solution is dried on Na$_2$SO$_4$, filtered and concentrated under reduced pressure. A white solid of molecule A13 in hydrochloride salt form is obtained.

Yield: 5.17 g (91%)
$^1$H NMR (TFA-d, ppm): 0.87 (3H); 1.06-1.46 (20H); 1.46-1.68 (2H); 1.68-2.81 (28H); 3.13-4.59 (12.5H); 4.83-5.25 (11H); 7.02-9.13 (37H)
DP (estimated as per $^1$H NMR): 5.5
The calculated average molar mass of molecule A13 in hydrochloride salt form is 1609.8 g/mol.

Co-polyamino acid B15-1: Molecule A13 (3.47 g, 2.16 mmol) is solubilized in DCM (17 mL) then is added successively at 0° C. butyltetracarboxylic acid (BTCA, 115 mg, 0.49 mmol), HOPO (275 mg, 2.48 mmol), DIPEA (377 μL, 2.16 mmol) followed by EDC (473 mg, 2.47 mmol). After stirring overnight at 0° C., the reaction medium is poured onto MeOH (220 mL) under stirring at 0° C. After overnight, the white precipitate is recovered by vacuum filtration, triturated with cold MeOH then dried under vacuum at 30° C.

Co-Polyamino Acid B15

A solution of co-polyamino acid B15-1 (2.33 g, 0.362 mmol) in DMAc (33 mL) is placed in a hydrogen atmosphere (1 atm) in the presence of 5% palladium on alumina (465 mg) then the solution is heated to 60° C. After leaving overnight, the solution is cooled, filtered under Celite® then the filtrate is poured onto a 15% NaCl solution at pH 2 (500 mL). After leaving overnight, the precipitate is filtered on a sintered filter then washed twice with a 15% NaCl solution (2×8 mL). The solid obtained is then solubilized in water (70 mL) by adjusting the pH to 7 by adding an aqueous solution of 1 N sodium hydroxide. After solubilization, the solution is filtered on a 0.45 μm filter then purified by ultrafiltration against a 0.9% NaCl solution, followed by water until the conductimetry of the permeate is less than 50 μS/cm. The solution obtained is filtered on a 0.2 μm filter and stored at 2-8° C.

Dry extract: 25.8 mg/g
$^1$H NMR ($D_2O$, ppm): 0.90 (10.2H); 1.18-1.46 (68H); 1.53-1.9 (6.8H); 1.86-3.04 (101.2H); 3.17-3.80 (20.4H); 4.19-4.68 (22.1H)
DP (estimated as per $^1$H NMR): 5.5
As per $^1$H NMR: i=3.4
The calculated average molar mass of co-polyamino acid B15 is 4261.3 g/mol.
HPLC-Organic SEC (PEG calibrator): Mn=2700 g/mol.

Example B16: Co-polyamino Acid B16—Sodium Poly-L-glutamate Modified at its Extremities by Molecule A14 wherein the Esters are Deprotected and having a Number Average Molar mass (Mn) of 3200 g/mol Co-polyamino acid B16-1: poly-L-benzylglutamate obtained from the polymerization of γ-benzyl-L-glutamate N-carboxyanhydride initiated by 1-amino-4,7,10-trioxa-13-tridecane amine (TOTA).

Using a similar method to the one used for the preparation of co-polyamino acid B2-1 applied to TOTA (13.96 g, 63.37 mmol) and to γ-benzyl-L-glutamate N-carboxyanhydride (400.0 g, 1519 mmol), co-polyamino acid B16-1 is obtained.

Co-Polyamino Acid B16

To a solution of molecule A14 (6.74 g, 13.5 mmol) in DMAc (38 mL) are successively added HOPO (1.65 g, 14.8 mmol)m, and EDC (3.36 g, 17.6 mmol).

To a solution of co-polyamino acid B16-1 (30.0 g) in DMAc (113 mL) at ambient temperature are successively added DIPEA (1.90 mL, 13.5 mmol) followed by the solution of molecule A14 previously prepared.

After 24 h of stirring at ambient temperature, DMAc (82 mL) is added and the solution is placed at 60° C. under 10 bar of hydrogen in the presence of 5% palladium on alumina (7.0 g). After 17 h of reaction, the reaction medium is filtered on a sintered filter then on a 0.2 μm PTFE filter.

The filtrate is placed under stirring, then a 300 g/L sodium carbonate solution (46 mL) followed by acetone (275 mL) are then added successively dropwise. After 3 h, the precipitate is filtered on a sintered filter, washed with acetone (3×70 mL) and dried under reduced pressure.

After solubilizing the solid obtained in water (1.3 L) then diluting with ethanol (0.7 L), the solution is basified by adding 10 N sodium hydroxide (13 mL) until a pH of 13 is obtained. After 3 h of stirring at ambient temperature, the solution is neutralized by adding 1 N HCl solution (190 mL) then the solution is filtered on an R53SLP carbon filter (3M), then on a 0.2 μm PES filter. The solution is then purified by ultrafiltration against a 0.9% NaCl solution, followed by water until the conductimetry of the permeate is less than 50 μS/cm. The solution obtained is filtered on a 0.2 μm filter and stored at 2-8° C.

Dry extract: 21.4 mg/g
DP (estimated as per $^1$H NMR): 24
As per $^1$H NMR: i=0.078
The calculated average molar mass of co-polyamino acid B16 is 4761 g/mol.
HPLC-Organic SEC (PEG calibrator): Mn=3200 g/mol.

Example B17: Co-Polyaminoacid B17—Sodium Poly-L-glutamate Modified at its Two Extremities by Molecule A15 and having a Number Average Molar Mass (Mn) of 3200 g/mol Co-polyamino acid B17-1: Poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylenediamine (4.77 g, 79.37 mmol) and to γ-benzyl-L-glutamate N-carboxyanhydride (500.0 g, 1899 mmol), co-polyamino acid B17-1 is obtained.

Co-polyamino acid B17

Using a similar method to the one used for the preparation of co-polyamino acid B16 applied to co-polyamino acid B17-1 (15.0 g) and to molecule A15 (3.45 g) with a saponification step at pH 12 for 50 min, co-polyamino acid B17 is obtained.

Dry extract: 20.3 mg/g
DP (estimated as per $^1$H NMR): 24
As per $^1$H NMR: i=0.048
The calculated average molar mass of co-polyamino acid B17 is 4237 g/mol.
HPLC-Organic SEC (PEG calibrator): Mn=3200 g/mol Example B18: Co-Polyaminoacid B18—Sodium Poly-L-glutamate Modified at its Two Extremities by Molecule A16 and having a Number Average Molar Mass (Mn) of 3150 g/mol Co-polyamino acid B18-1: poly-L-benzylglutamate obtained from the polymerization of γ-benzyl-L-glutamate N-carboxyanhydride initiated by ethylenediamine.

Using a similar method to the one used for the preparation of co-polyamino acid B2-1 applied to ethylenediamine (4.74 g, 78.89 mmol) and to γ-benzyl-L-glutamate N-carboxyanhydride (498.4 g, 1893 mmol), co-polyamino acid B18-1 is obtained.

Co-Polyamino Acid B18

Using a similar method to the one used for the preparation of co-polyamino acid B17 applied to co-polyamino acid B18-1 (14.0 g) and to molecule A16 (4.26 g), co-polyamino acid B18 is obtained.

Dry extract: 9.7 mg/g
DP (estimated as per $^1$H NMR): 24
As per $^1$H NMR: i=0.075
The calculated average molar mass of co-polyamino acid B18 is 4839 g/mol.
HPLC-Organic SEC (PEG calibrator): Mn=3150 g/mol Example B19: Co-polyamino Acid B19—Sodium Poly-L-glutamate Modified at its Extremities by Molecule A17 wherein the Esters are Deprotected and having a Number Average Molar Mass (Mn) of 3400 g/mol Using a similar method to the one used for the preparation of co-polyamino acid B16 applied to co-polyamino acid B18-1 (20.39 g) and to molecule A17 (7.553 g), co-polyamino acid B19 is obtained.

Dry extract: 18.6 mg/g
DP (estimated as per $^1$H NMR): 24
As per $^1$H NMR: i=0.066

The calculated average molar mass of co-polyamino acid B19 is 4936 g/mol.

HPLC-Organic SEC (PEG calibrator): Mn=3400 g/mol

Example B20: Co-Polyaminoacid B20—Sodium Poly-L-glutamate Modified at its Two Extremities by Molecule A18 and having a Number Average Molar Mass (Mn) of 3200 g/mol Using a similar method to the one used for the preparation of co-polyamino acid B17 applied to co-polyamino acid B17-1 (12.45 g) and to molecule A18 (3.56 g), co-polyamino acid B20 is obtained.

Dry extract: 16.8 mg/g
DP (estimated as per $^1$H NMR): 24
As per $^1$H NMR: i=0.075

The calculated average molar mass of co-polyamino acid B20 is 4784 g/mol.

HPLC-Organic SEC (PEG calibrator): Mn=3200 g/mol

Example B21: Co-Polyaminoacid B21—Sodium Poly-L-glutamate Modified at its Two Extremities by Molecule A19 and having a Number Average Molar Mass (Mn) of 3600 g/mol Using a similar method to that used for the preparation of co-polyamino acid B17 applied to co-polyamino acid B17-1 (12.16 g) and to molecule A19 (4.16 g), co-polyamino acid B21 is obtained.

Dry extract: 26.4 mg/g
DP (estimated as per $^1$H NMR): 24
As per $^1$H NMR: i=0.077

The calculated average molar mass of co-polyamino acid B21 is 5023 g/mol.

HPLC-Organic SEC (PEG calibrator): Mn=3600 g/mol

Example B23: Co-Polyaminoacid B23—Sodium Poly-L-glutamate Modified at its Two Extremities by Molecule A21 and having a Number Average Molar Mass (Mn) of 3350 g/mol Using a similar method to the one used for the preparation of co-polyamino acid B17 applied to co-polyamino acid B17-1 (18.68 g) and to molecule A21 (7.03 g), co-polyamino acid B23 is obtained.

Dry extract: 23.2 mg/g
DP (estimated as per $^1$H NMR): 24
As per $^1$H NMR: i=0.080

The calculated average molar mass of co-polyamino acid B23 is 5140 g/mol.

HPLC-Organic SEC (PEG calibrator): Mn=3350 g/mol

Example B24: Co-polyamino Acid B24—Sodium Poly-L-glutamate Modified at its Extremities by Molecule A1 and having a Number Average Molar Mass (Mn) of 2300 g/mol Co-polyamino acid B24-1: poly-L-benzylglutamate obtained from the polymerization of γ-benzyl-L-glutamate N-carboxyanhydride initiated by molecule 4 and modified at its extremities by molecule A1.

To a suspension of molecule 4 (9.92 mmol) in anhydrous DMF (80 mL) cooled to 0° C. is rapidly added a solution of γ-benzyl-L-glutamate N-carboxyanhydride (26.11 g, 99.2 mmol) in anhydrous DMF (20 mL) at 0° C. After 24 h of stirring at 0° C., a freshly prepared solution of molecule A1 (16.1 g, 49.6 mmol), HATU (18.9 g, 49.6 mmol) and DIPEA (8.64 mL, 49.6 mmol) in DMF (80 mL) is added to the medium and the mixture is stirred from 0° C. to 25° C. for 3.5 h. The resin is filtered, washed successively with DMF (3×100 mL), isopropanol (1×100 mL) and DCM (3×100 mL). The resin obtained is then treated with an 80:20 DCM/HFIP mixture (120 mL). After 30 min of stirring at ambient temperature, the resin is filtered and washed successively with DCM (3×100 mL). The solvents are evaporated under reduced pressure to produce co-polyamino acid B24-1

Co-Polyamino Acid B24

Using a similar method to the one used for the hydrogenation step of co-polyamino acid B16 applied to co-polyamino acid B24-1 (27.4 g), with a saponification step at pH 12 for 50 min but without the carbofiltration step, co-polyamino acid B24 is obtained.

Dry extract: 14.1 mg/g
DP (estimated as per $^1$H NMR): 14
As per $^1$H NMR: i=0.143

The calculated average molar mass of co-polyamino acid B24 is 2899 g/mol.

HPLC-Organic SEC (PEG calibrator): Mn=2300 g/mol.

Example B25: Co-Polyaminoacid B25—Sodium Poly-L-glutamate Modified at its Extremities by Molecule A22 and having a Number Average Molar Mass (Mn) of 3050 g/mol Using a similar method to the one used for the preparation of co-polyamino acid B17 applied to co-polyamino acid B18-1 (30.0 g) and molecule A22 (8.56 g) using a four-fold greater quantity of 300 g/l sodium carbonate solution to precipitate the polymer after the hydrogenolysis step, co-polyamino acid B25 is obtained.

Dry extract: 23.7 mg/g
DP (estimated as per $^1$H NMR): 24
As per $^1$H NMR: i=0.074

The calculated average molar mass of co-polyamino acid B25 is 4743 g/mol.

HPLC-Organic SEC (PEG calibrator): Mn=3050 g/mol

Example B26: Co-Polyaminoacid B26—Sodium poly-L-glutamate Modified at its Two Extremities by Molecule A23 and having a Number Average Molar Mass (Mn) of 3400 g/mol Using a similar method to the one used for the preparation of co-polyamino acid B25 applied to co-polyamino acid B17-1 (25.78 g) and to molecule A23 (8.27 g), co-polyamino acid B21 is obtained.

Dry extract: 11.8 mg/g
DP (estimated as per $^1$H NMR): 24
As per $^1$H NMR: i=0.073

The calculated average molar mass of co-polyamino acid B21 is 4902 g/mol.

HPLC-Organic SEC (PEG calibrator): Mn=3400 g/mol

Example B27: Co-polyamino Acid B27—Butyltetracarboxylic Acid Substituted with Molecule A24 wherein the Esters are Deprotected and having a Number Average Molar Mass (Mn) of 2500 g/mol Molecule A24

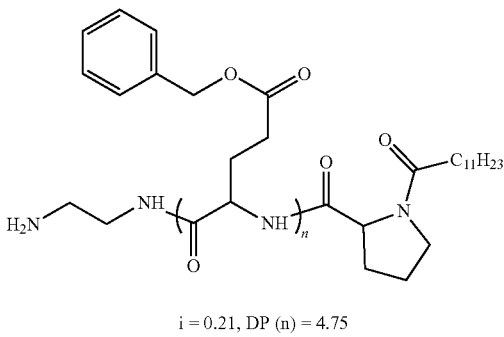

i = 0.21, DP (n) = 4.75

Molecule 53: Product obtained by polymerization of γ-benzyl-L-glutamate N-carboxyanhydride initiated by N-Boc-ethylenediamine then capped with molecule 2.

A solution of BocEDA (12.00 g, 74.9 mmol) in DMF (12 mL) is prepared. In a reaction vessel, γ-benzyl-L-glutamate N-carboxyanhydride (78.87 g, 300.0 mmol) is solubilized in DMF (165 mL) at 25° C. The mixture is then stirred until complete dissolution, cooled to −10° C., then the BocEDA solution is introduced rapidly. The reaction medium is stirred at 0° C. for 3 h then are introduced successively DMF (100 mL), molecule 2 (26.73 g, 89.88 mmol), HOPO (9.99 g, 89.88 mmol) and EDC (17.23 g, 89.88 mmol). The reaction mixture is stirred at 0° C. for 1 h, from 0° C. to 20° C. for 2 h then at 20° C. for 16 h. It is then poured onto a 1:1 2-propanol/$H_2O$ solution (10 V) under stirring. After 3 h, the white precipitate is filtered on a sintered filter, washed with a 1:1 2-propanol/$H_2O$ mixture (2×360 mL) and dried at 30° C. under reduced pressure.

Yield: 70 g (71%)

$^1$H NMR (TFA-d, ppm): 0.99 (3H); 1.34-1.59 (16H); 1.68-2.85 (36H); 3.52-3.62 (2H); 3.79-3.99 (4H); 4.70-4.92 (5.75H); 5.20-5.38 (9.5H); 7.36-7.52 (23.75H).

DP (estimated as per $^1$H NMR): 4.75

The calculated average molar mass of molecule 53 is 1481.0 g/mol.

Molecule A24

Using a similar method to the one used for the preparation of molecule A13 applied to molecule 53 (34.00 g, 22.96 mmol), a white solid of molecule A24 in hydrochloride salt form is obtained.

Yield: 29.40 g (90%)

$^1$H NMR (TFA-d, ppm): 1.00 (3H); 1.35-1.61 (16H); 1.79-1.93 (2H); 2.05-2.90 (25H); 3.53-3.65 (2H); 3.79-4.02 (4H); 4.74-4.94 (5.75H); 5.20-5.43 (9.5H); 7.32-7.58 (23.75H).

DP (estimated as per $^1$H NMR): 4.75

The calculated average molar mass of molecule A13 in hydrochloride salt form is 1417.2 g/mol.

Co-Polyamino Acid B27-1:

Using a similar method to the one used for the preparation of co-polyamino acid B15-1 applied to molecule A24 (11.9 g, 8.40 mmol) and to BTCA (0.41 g, 1.75 mmol) in solution in DMF, a white solid is obtained after drying at 30° C. under reduced pressure.

Co-Polyamino Acid B27

Using a similar method to the one used for the preparation of co-polyamino acid B15 applied to co-polyamino acid B27-1 (9.31 g, 1.64 mmol), under hydrogen pressure (6 bar) and with a saponification step at pH 12 for 1 h prior to the ultrafiltration step, co-polyamino acid B27 is obtained.

Dry extract: 19.9 mg/g

DP (estimated as per $^1$H NMR): 4.75

As per $^1$H NMR: i=3.7

The calculated average molar mass of co-polyamino acid B27 is 4085.8 g/mol.

HPLC-Organic SEC (PEG calibrator): Mn=2500 g/mol.

Example B28: Co-polyamino Acid B28—Tricarballylic Acid Substituted with Molecule A25 wherein the Esters are Deprotected and having a Number Average Molar Mass (Mn) of 2200 g/mol Molecule A25

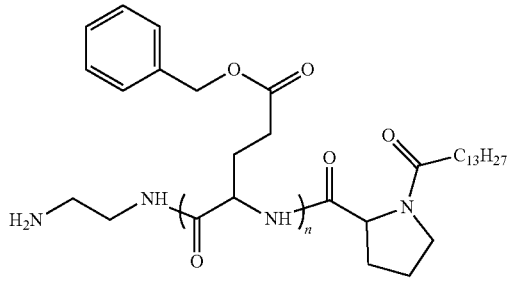

i = 0.19, DP (n) = 5.15

Molecule 54: Product obtained by polymerization of γ-benzyl-L-glutamate N-carboxyanhydride initiated by N-Boc-ethylenediamine then capped with molecule A1.

Using a similar method to the one used for the preparation of molecule 53 applied to BocEDA (6.00 g, 37.45 mmol), to γ-benzyl-L-glutamate N-carboxyanhydride (39.44 g, 150.00 mmol) and to molecule A1 (14.63 g, 44.94 mmol), a white solid of molecule 54 is obtained.

Yield: 23.71 g (40%)

$^1$H NMR (CDCl$_3$, ppm): 0.87 (3H); 1.12-2.76 (57.6H); 3.06-4.50 (12.15H); 4.90-5.25 (10.3H); 5.91-8.49 (32.9H).

DP (estimated as per $^1$H NMR): 5.15

The calculated average molar mass of molecule 54 is 1596.8 g/mol.

Molecule A25

Using a similar method to the one used for the preparation of molecule A13 applied to molecule 54 (23.29 g, 14.59 mmol), a translucent solid of molecule A25 in hydrochloride salt form is obtained.

Yield: 19.08 g (85%)

$^1$H NMR (CDCl$_3$, ppm): 0.87 (3H); 1.17-1.32 (20H); 1.48-1.63 (2H); 1.69-2.78 (29.6H); 3.15-4.40 (12.15H); 4.89-5.18 (10.3H); 7.06-9.13 (31.9H).

DP (estimated as per $^1$H NMR): 5.15

The calculated average molar mass of molecule A25 in hydrochloride salt form is 1533.1 g/mol.

Co-Polyamino Acid B28-1:

Using a similar method to the one used for the preparation of co-polyamino acid B15-1 applied to molecule A25 (3.93 g, 2.56 mmol) and to tricarballylic acid (TCA, 125.2 mg, 0.71 mmol) in solution in DMF, a white solid is obtained after drying at 30° C. under reduced pressure.

Co-Polyamino Acid B28

Using a similar method to the one used for the preparation of co-polyamino acid B15 applied to co-polyamino acid B28-1 (2.98 g, 0.65 mmol) and with a saponification step at pH 12 for 1 h prior to the ultrafiltration step, co-polyamino acid B28 is obtained.

Dry extract: 25.8 mg/g

DP (estimated as per $^1$H NMR): 5.15

As per $^1$H NMR: i=3.0

The calculated average molar mass of co-polyamino acid B28 is 3559.2 g/mol.

HPLC-Organic SEC (PEG calibrator): Mn=2200 g/mol.

Example B29: Co-polyamino Acid B29-4,7,10-trioxa-1,13-tridecanediamine (TOTA) Substituted with Molecule A12 wherein the Esters are Deprotected and having a Number Average Molar Mass (Mn) of 2000 g/mol Co-polyamino acid B29-1:

To a solution of molecule A12 (3.70 g, 1.98 mmol) in chloroform (31 mL) at ambient temperature are added successively HOBt (304 mg, 1.98 mmol) and 4,7,10-trioxa-1,13-tridecanediamine (TOTA, 208 mg, 0.94 mmol). The mixture is cooled to 0° C. then EDC (380 mg, 1.98 mmol) is added. The reaction medium is stirred for 15 min at 0° C. followed by 18 h at ambient temperature. The organic phase is washed with a 0.1 N HCl aqueous solution (2×28 mL), and the organic phase is dried on $Na_2SO_4$, filtered and concentrated under reduced pressure. The solid obtained is solubilized in $CHCl_3$ (40 mL) and the solution is added dropwise to IPE (400 mL) under stirring. The suspension is placed in an ice bath without stirring for 17 h. The suspension is centrifuged at 3200 rpm for 10 min at 25° C. The colorless supernatant is removed and the solid obtained is concentrated under reduced pressure.

Yield: 4.59 g (quant.)

$^1$H NMR ($CDCl_3$, ppm): 0.88 (12H); 1.12-1.58 (192H); 1.58-2.17 (48H); 2.17-2.62 (44H); 3.08 (2H); 3.13-3.38 (6H); 3.48 (4H); 3.53-3.66 (12H); 3.74-3.83 (4H); 3.92 (2H); 4.00-4.12 (4H); 4.12-4.33 (10H); 4.37 (2H); 6.72-6.84 (4H); 7.06 (2H); 7.31 (2H); 7.52 (2H); 7.82 (2H); 7.94 (2H); 8.57-8.69 (4H).

Co-Polyamino Acid B29

Molecule B29-1 (3.67 g, 0.93 mmol) is solubilized in TFA (11.5 mL) and the solution is stirred at ambient temperature for 6 h. The solution is poured dropwise onto IPE (18 mL) at 5° C. then water (18 mL) is added. The suspension is placed in an ice bath under stirring for 15 h. The suspension is filtered and triturated with IPE (10 mL) and water (2×10 mL). The residue is dried under reduced pressure then solubilized in a 1 N NaOH solution (56 mL) with regular addition of 1 N NaOH to maintain the pH at 7. The solution is diluted to 20 g/L theoretical with water then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 8.0 mg/g

The calculated average molar mass of co-polyamino acid B29 is 3520 g/mol.

HPLC-Organic SEC (PEG calibrator): Mn=2000 g/mol.

Example B30: Co-polyamino Acid B30—Tricarballylic Acid Substituted with Molecule A26 wherein the Esters are Deprotected and having a Number Average Molar Mass (Mn) of 2100 g/mol Co-Polyamino Acid B30-1:

Using a similar method to supernatant used for the preparation of co-polyamino acid B15-1 applied to molecule A26 (10.87 g, 11.33 mmol) and to tricarballylic acid (TCA, 0.605 g, 3.43 mmol) in solution in DMF, a white solid is obtained after 2 consecutive precipitations of the product in solution in DMF in a 50:50 $H_2O$/MeCN mixture (10V), filtration, trituration with a 50:50 $H_2O$/MeCN mixture followed by drying under reduced pressure at 30° C.

Co-Polyamino Acid B30

Co-polyamino acid B30-1 (8.53 g, 2.95 mmol) is solubilized in TFA (30 mL), and the solution is stirred for 3 h at ambient temperature then is poured dropwise onto water under stirring (300 mL). After 1 h, the white precipitate is recovered by filtration, triturated with water and dried under reduced pressure. The solid obtained is then solubilized in water (350 mL) by adjusting the pH to 7 adding an aqueous solution of 1 N sodium hydroxide. The solution is filtered on a 0.2 µm filter then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 28.8 mg/g

The molar mass of co-polyamino acid B30 is 2585 g/mol.

HPLC-Organic SEC (PEG calibrator): Mn=2100 g/mol.

Example B31: Co-polyamino Acid B31—Sodium Poly-L-glutamate Modified at its Extremities by Molecule A27 wherein the Esters are Deprotected and having a Number Average Molar Mass (Mn) of 3800 g/mol Using a similar method to the one used for the preparation of co-polyamino acid B16 applied to co-polyamino acid B18-1 (28.6 g) and to molecule A27 (6.799 g), co-polyamino acid B31 is obtained.

Dry extract: 20.5 mg/g

DP (estimated as per $^1$H NMR): 24

As per $^1$H NMR: i=0.075

The calculated average molar mass of co-polyamino acid B31 is 4591 g/mol.

HPLC-Organic SEC (PEG calibrator): Mn=3800 g/mol

Part CE—Co-polyamino Acid Counterexamples

| # | CO-POLYAMINO ACID COUNTEREXAMPLES |
|---|---|
| CE1 | 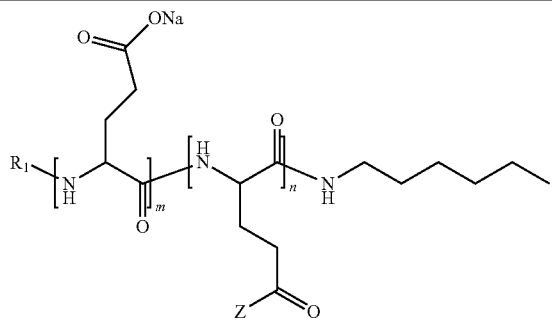<br>$i = 0.05$, DP $(m + n) = 22$<br>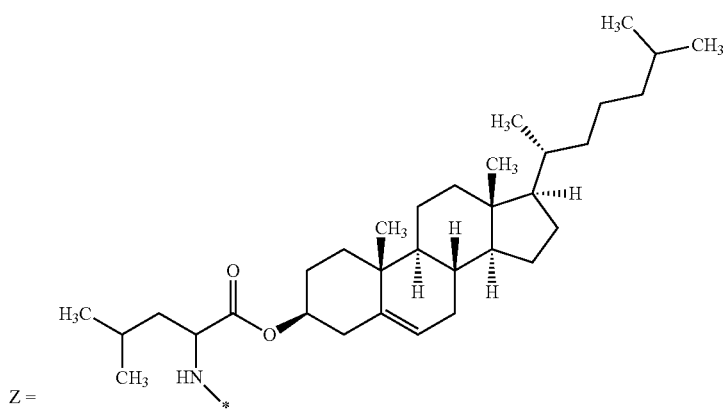<br>$R_1 = CH_3-CO-$, H or pyroglutamate |
| CE2 | $i = 0.05$, DP $(m + n) = 43$<br>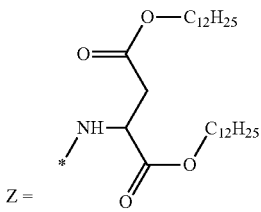<br>$R_1 = CH_3-CO-$, H or pyroglutamate |

Co-polyamino acids CE1 and CE2 are synthesized according to the method described in the application WO2017211916.

Part C: Compositions

Example C1

Rapid-Acting Insulin Analog Solution (Humalog®) at 100 U/mL

This solution is a commercial insulin lispro solution marketed by ELI LILLY under the trade name Humalog®. This product is a rapid-acting insulin analog. The excipients in Humalog® are m-cresol (3.15 mg/mL), glycerol (16 mg/mL), disodium phosphate (1.88 mg/mL), zinc oxide (to obtain 0.0197 mg of zinc ion/mL), sodium hydroxide and hydrochloric acid to adjust the pH (pH 7-7.8) and water.

Example C2

Rapid-Acting Insulin Lispro Analog Solution at 100-600 U/mL

This solution is an insulin solution prepared from insulin lispro powder produced by Gan&Lee. This product is a rapid-acting insulin analog. The excipients used are m-cresol, glycerol, zinc oxide, sodium hydroxide and hydrochloric acid to adjust the pH (pH 7-7.8) and water. The zinc concentration is 300 µM per 100 IU/mL of insulin. The concentration of the excipients varies according to of the one of lispro to obtain the desired concentrations in the final formulations.

Example C3

Slow-Acting Insulin Analog Solution (Lantus®) at 100 U/mL

This solution is a commercial insulin glargine solution marketed by SANOFI under the trade name Lantus®. This product is a slow-acting insulin analog. The excipients in Lantus® are zinc chloride (30 µg/mL), m-cresol (2.7 mg/mL), glycerol (20 mg/mL), polysorbate 20 (16 µM), sodium hydroxide and hydrochloric acid to adjust the pH (pH 4) and water.

Example C4

Insulin Glargine Solution at 100-400 U/mL

This solution is an insulin glargine solution prepared from insulin glargine powder produced by Gan&Lee. This product is a slow-acting insulin analog. The excipients used are zinc chloride, m-cresol, glycerol*, sodium hydroxide and hydrochloric acid to adjust the pH (pH 4) and water. The zinc concentration is 460 µM per 100 IU/mL of insulins. The concentration of the other excipients varies according to the one of glargine to obtain the desired concentrations in the final formulations.

Part CA—Compositions Comprising Insulin Glargine

Preparation method CA1: Preparation of a dilute co-polyamino acid/50 U/mL insulin glargine solution at pH 7.1, according to a method using insulin glargine in liquid form (in solution) and a co-polyamino acid in liquid form (in solution).

To a stock solution of co-polyamino acid at pH 7.1 are added concentrated solutions of m-cresol and glycerin so as obtain a co-polyamino acid solution of concentration $C_{stock\ co-polyamino\ acid/excipients}$ (mg/mL). The quantity of excipients added is adjusted in order to obtain a concentration of m-cresol of 35 mM and glycerin of 184 mM in the co-polyamino acid/50 U/mL insulin glargine composition at pH 7.1.

In a sterile container, a volume $V_{insulin\ glargine}$ of an insulin glargine solution at a concentration of 100 U/mL described in C3 or C4 is added to a volume $V_{stock\ co-polyamino\ acid/excipients}$ of a co-polyamino acid solution at the concentration $C_{stock\ co-polyamino\ acid/excipients}$ (mg/mL) in order to obtain a dilute co-polyamino acid composition $C_{dilute\ co-polyamino\ acid}$ (mg/mL)/50 U/mL insulin glargine at pH 7.1. A turbidity appears. The pH is adjusted to pH 7.1 by adding concentrated NaOH and the solution is placed under static conditions at 40° C. for 2 h until complete solubilization. This visually clear solution is placed at 4° C.

Preparation method CA2: Preparation of a concentrated co-polyamino acid/insulin glargine composition at pH 7.1 using a co-polyamino acid, according to a dilute composition concentration method.

A co-polyamino acid/50 U/mL insulin glargine composition at pH 7.1 described in example CA1 is concentrated by ultrafiltration on a 3 kDa membrane made of regenerated cellulose (Amicon® Ultra-15 marketed by Millipore). Following this ultrafiltration step, the retentate is clear and the insulin glargine concentration in the composition is determined by reverse phase chromatography (RP-HPLC). The insulin glargine concentration in the composition is then adjusted to the desired value by dilution in a solution of m-cresol/glycerin excipients in order to obtain a final concentration of m-cresol of 35 mM, Tween 20 of 52 µM and an osmolarity of 300 mOsmol/kg. The pH is measured and adjusted to pH 7.1 by adding NaOH and concentrated HCl. This visually clear solution at pH 7.1 has an insulin glargine concentration $C_{insulin\ glargine}$ (U/mL) and a co-polyamino acid concentration $C_{co-polyamino\ acid}$ (mg/mL)= $C_{dilute\ co-polyamino\ acid}$ (mg/mL)×$C_{insulin\ glargine}$ (U/mL)/50 (U/mL).

Preparation method CA3: Preparation of a concentrated co-polyamino acid/insulin glargine solution at pH 7.1, according to a method using insulin glargine in liquid form (in solution) and a co-polyamino acid in liquid form (in solution).

To a stock solution of co-polyamino acid at pH 7.1 is added a glargine solution of 220-400 IU/mL containing the excipients described in example C4. The concentration of the excipients in the glargine solution is adjusted in order to obtain a concentration of m-cresol of 35 mM, glycerin of 184 mM in the co-polyamino acid/insulin glargine composition at pH 7.1. A turbidity appears. The pH is adjusted to pH 7.1 by adding concentrated NaOH and the solution is placed under static conditions at 40° C. for 2 h until complete solubilization. This visually clear solution is placed at 4° C. after adding a volume of concentrated polysorbate 20 solution to obtain a final concentration of 52 µM.

According to preparation methods CA2 or CA3, co-polyamino acid/insulin glargine compositions were prepared for example with insulin glargine concentrations from 200 U/mL to 300 U/mL.

Example CA4

Preparation of Co-polyamino Acid/200 U/ml Insulin Glargine Compositions at pH 7.1

Co-polyamino acid/200 U/mL insulin glargine compositions are prepared according to the method described in CA2 and CA3 in order to obtain an insulin glargine concentration $C_{insulin\ glargine}$=200 U/mL and a co-polyamino acid concentration $C_{co-polyamino\ acid}$ (mg/mL).

These compositions are shown in Table 1.

TABLE 1

Insulin glargine (200 U/mL) compositions in the presence of co-polyamino acids.

| Composition | Co-polyamino acid | Co-polyamino acid concentration (in mg/ml) | Insulin glargine (U/mL) | Visual appearance of solution |
|---|---|---|---|---|
| CA3-1 | B5 | 5 | 200 | clear |
| CA3-2 | B6 | 7 | 200 | clear |

The co-polyamino acids allow the solubilization of insulin glargine at neutral pH and lead to a clear solution.

Example CA5

Determination of Minimum Co-polyamino Acid Concentration to Solubilize 50 IU/mL Insulin Glargine at pH 7.1

To a stock solution of co-polyamino acid at pH 7.2±0.3 are added concentrated solutions of zinc chloride, sodium chloride, m-cresol and glycerin. 0.5 mL of an insulin glargine solution at a concentration of 100 U/mL, prepared according to example C3 or C4, is added to a volume of 0.5 mL of the solution of co-polyamino acid and excipients to obtain a co-polyamino acid/50 U/ml insulin glargine composition with the desired composition. The co-polyamino acid concentration varies from one preparation to another: solutions having co-polyamino acid concentrations varying not more than 1 mg/ml are prepared in this way.

Following the addition of the glargine solution, a turbidity appears. The pH is adjusted to pH 7.1 by adding concentrated NaOH and the solution is placed in an oven at 40° C. overnight. After leaving overnight at 40° C., the samples are visually inspected and subjected to a static light scattering measurement at an angle of 173° using a zetasizer (Malvern). The minimum concentration of co-polyamino acid suitable for solubilizing insulin glargine is defined as the lowest concentration for which the co-polyamino acid/insulin glargine mixture at pH 7.1±0.1 is visually clear, is free from visible particles and has a scattered intensity less than 1500 kcps/s.

Preparation method CA5a: Preparation of a co-polyamino acid/insulin glargine solution at pH 7.2, according to a method using insulin glargine in liquid form (in solution) and a co-polyamino acid in liquid form (in solution).

To a stock solution of co-polyamino acid at pH 7-7.5 are added a sodium chloride solution and a $ZnCl_2$ solution to obtain the targeted concentrations in the co-polyamino acid/insulin glargine composition. A 100-220 U/mL glargine solution described in example C4 is added. The concentrations of the excipients in the glargine solution are adjusted in order to obtain a concentration of m-cresol of 35 mM and of glycerin of 230 mM in the co-polyamino acid/insulin glargine composition. A turbidity appears. The pH is adjusted to pH 7.5 by adding concentrated NaOH and the solution is placed in an oven at 40° C. for 2 h until complete solubilization. The solution obtained is visually clear.

Example CA6

Determination of Minimum Concentration of Co-polyamino Acid B20 to Solubilize 50 IU/ml Insulin Glargine at pH 7.1 in the Presence of Glycerin (184 mM), m-cresol (35 mM) and different NaCl and Zinc Chloride Concentrations According to the preparation method CA5, the minimum concentration of co-polyamino acid B20 to solubilize insulin glargine is determined for different zinc chloride and sodium chloride contents. The results are described in Table 1a.

Example CA6a

Determination of Minimum Concentration of different Co-polyamino Acids to Solubilize 50 IU/ml Insulin Glargine at pH 7.1 in the Presence of Glycerin (184 mM) and M-Cresol (35 mM)

Using a similar method to the one described in example CA6, the minimum concentration determined for different co-polyamino acids according to the invention is shown in Table 1a.

TABLE 1a

Minimum concentration of different co-polyamino acids to solubilize insulin glargine

| Composition | Co-polyamino acid | [ZnCl$_2$] (mM) | [NaCl] (mM) | Co-polyamino acid concentration at limit of solubilization (mg/mL) | Ratio [Hy]/[insulin glargine] at limit of solubilization (mol/mol) |
|---|---|---|---|---|---|
| CA6-19 | B14 | 0.23 | — | 0.75 | 0.76 |
| CA6-21 | B26 | 0.23 | — | 0.63 | 0.8 |
| CA6-22 | B9 | 0.23 | — | 0.75 | 0.76 |
| CA7-23 | CE1 | 0.23 | — | 1.0 | 0.9 |
| CA7-24 | CE2 | 0.23 | — | 1.0 | 0.8 |

Co-polyaminoacids B14, B26 and B9 are suitable for solubilizing 50 U/mL glargine at a co-polyamino acid concentration less than or equal to 1 mg/mL.

Example CA6b

Determination of Improvement Percentage of the Minimum Concentration of Different Co-polyamino Acids to Solubilize 50 IU/ml Insulin Glargine at pH 7.1 in the Presence of Glycerin (184 mM), M-Cresol (35 mM) and different NaCl and Zinc Chloride Concentrations Using a similar method to the one described in example CA6, the reduction percentage of the minimum concentration determined for different co-polyamino acids according to the invention provided by adding NaCl and zinc chloride is shown in Table 1b.

TABLE 1b

Decrease of the minimum concentration of different co-polyamino acids to solubilize insulin glargine in the presence of NaCl and zinc chloride.

| Composition | Co-polyamino acid | [ZnCl$_2$] (mM) | [NaCl] (mM) | Reduction of co-polyamino acid concentration at limit of solubilization with respect to reference concentration without salts (%) |
|---|---|---|---|---|
| CA6-2 | B20 | 0.23 | 10 | 25% |
| CA6-3 | B20 | 0.76 | 10 | 50% |
| CA6-4 | B17 | 0.23 | 10 | 14% |
| CA6-5 | | | | |
| CA6-6 | | 0.40 | 10 | 57% |
| CA6-7 | B18 | 0.23 | 10 | 25% |
| CA6-8 | | | | |
| CA6-9 | | 0.40 | 10 | 37% |
| CA6-10 | B19 | 0.23 | 10 | 40% |
| CA6-11 | | | | |
| CA6-12 | | 0.40 | 10 | 70% |
| CA6-13 | B23 | 0.23 | 10 | 17% |
| CA6-14 | | | | |
| CA6-15 | | 0.40 | 10 | 50% |
| CA6-16 | B31 | 0.23 | 10 | 45% |
| CA6-17 | | | | |
| CA6-18 | | 0.40 | 10 | 64% |
| CA7-23-1 | CE1 | 0.23 | 5 | 10%≤ |

TABLE 1b-continued

Decrease of the minimum concentration of different co-polyamino acids to solubilize insulin glargine in the presence of NaCl and zinc chloride.

| Composition | Co-polyamino acid | [ZnCl$_2$] (mM) | [NaCl] (mM) | Reduction of co-polyamino acid concentration at limit of solubilization with respect to reference concentration without salts (%) |
|---|---|---|---|---|
| CA7-23-2 | CE1 | 0.23 | 5 | 10%≤ |
| CA7-24-1 | CE2 | 0.23 | 10 | 10%≤ |
| CA7-24-2 | CE2 | 0.23 | 5 | 10%≤ |

Adding salt and/or zinc chloride helps enhance the efficacy of the co-polyamino acids according to the invention with respect to co-polyamino acid/glargine compositions free from salt. Adding 10 mM NaCl makes it possible to reduce the minimum concentration of co-polyamino acid by at least 14% and the supplementary addition of zinc chloride by at least 37% with respect to the reference compositions free from NaCl.

Part CB—Compositions Comprising Insulin Glargine and Insulin Lispro

Preparation method CB1: Preparation of a dilute co-polyamino acid/43 (U/mL) insulin glargine/13.5 (U/mL) insulin lispro composition To a volume $V_{co\text{-}polyamino\ acid/dilute\ insulin\ glargine}$ of the dilute co-polyamino acid/50 U/mL insulin glargine composition at pH 7.1 described in CA1 is added a volume $V_{insulin\ lispro}$ of a 100 U/mL lispro solution and water in order to obtain a co-polyamino acid/43 (U/mL) insulin glargine/13.5 (U/mL) insulin lispro composition.

Preparation method CB2: Preparation of a concentrated co-polyamino acid/insulin glargine/insulin lispro composition at pH 7.1

A co-polyamino acid/43 (U/mL) insulin glargine/13.5 (U/ml) insulin lispro composition described in example CB1 is concentrated by ultrafiltration on a 3 kDa membrane made of regenerated cellulose (Amicon® Ultra-15 marketed by MILLIPORE). Following this ultrafiltration step, the retentate is clear and the insulin glargine concentration in the composition is determined by reverse phase chromatography (RP-HPLC). The insulin glargine and insulin lispro concentrations in the composition are then adjusted to the desired value by dilution in a solution of m-cresol/glycerin excipients in order to obtain a final concentration of m-cresol of 35 mM and an osmolarity of 300 mOsm/kg. During this dilution step, a volume of concentrated polysorbate 20 solution is also added to obtain a final concentration of 52 µM. The pH is measured and adjusted if required to pH 7.1 by adding NaOH and concentrated HCl. This visually clear solution at pH 7.1 has an insulin glargine concentration $C_{insulin\ glargine}$ (U/mL), an insulin lispro concentration $C_{insulin\ lispro} = C_{insulin\ glargine} \times 0.33$ and a co-polyamino acid concentration $C_{co\text{-}polyamino\ acid}$ (mg/mL)= $C_{dilute\ co\text{-}polyamino\ acid}$ (mg/mL)×$C_{insulin\ glargine}$ (U/mL)/50 (U/mL).

Preparation method CB3: Preparation of a concentrated co-polyamino acid/insulin glargine/insulin lispro composition at pH 7.1

To a volume $V_{co\text{-}polyamino\ acid/concentrated\ insulin\ glargine}$ of the concentrated co-polyamino acid/insulin glargine composition at pH 7.1 described in example CA3 is added a volume $V_{insulin\ lispro}$ of a lispro solution described in example C2. A volume of polysorbate 20 solution is also added to obtain a final concentration of 52 µM. The resulting solution at pH 7.1 has an insulin glargine concentration $C_{insulin\ glargine}$ (U/mL), an insulin lispro concentration $C_{insulin\ lispro} = C_{insulin\ glargine} \times 0.33$ and a co-polyamino acid concentration $C_{co\text{-}polyamino\ acid}$ (mg/mL)= $C_{dilute\ co\text{-}polyamino\ acid}$ (mg/mL)×$C_{insulin\ glargine}$ (U/mL)/50 (U/mL). The concentration of m-cresol is 35 mM and that of glycerin 230 mM.

Preparation method CB4: Preparation of a co-polyamino acid/75 U/mL insulin glargine/25 U/mL insulin lispro composition at pH 7.2

To a volume of the concentrated co-polyamino acid/insulin glargine composition described in example CA5a is added a volume of an insulin lispro solution described in example C2. The pH is adjusted to 7.2 by adding a concentrated hydrochloric acid solution. The visually clear resulting solution has a concentration of insulin glargine of 75 U/mL and of insulin lispro of 25 U/mL. The concentration of m-cresol is 35 mM and that of glycerin 230 mM.

Preparation method CB5: Preparation of a co-polyamino acid/150 U/mL insulin glargine/50 U/mL insulin lispro composition at pH 7.2

To a volume of the concentrated co-polyamino acid/insulin glargine composition described in example CA5a is added a volume of a lispro solution described in example C2. The pH is adjusted to 7.2 by adding a concentrated hydrochloric acid solution. The visually clear resulting solution has a concentration of insulin glargine of 150 U/mL and of insulin lispro of 50 U/mL. The concentration of m-cresol is 35 mM and the one of glycerin 230 mM.

Example CB2 and CB3: Preparation of Co-polyamino Acid/200 U/mL Insulin Glargine/66 U/mL Insulin Lispro Compositions at pH 7.1

Co-polyamino acid/200 U/mL insulin glargine/66 U/ml insulin lispro compositions are prepared according to one of the methods described in examples CB2 and CB3 in order to obtain an insulin glargine concentration $C_{insulin\ glargine} = 200$ U/mL, an insulin lispro concentration $C_{insulin\ lispro} = 66$ U/mL and a co-polyamino acid concentration $C_{co\text{-}polyamino\ acid}$ (mg/mL).

These compositions are shown in Table 2.

TABLE 2

Insulin glargine (200 U/mL) and insulin lispro (66 U/ml) compositions in the presence of co-polyamino acids.

| Composition | Co-polyamino acid | Co-polyamino acid concentration (in mg/ml) | Insulin glargine (U/mL) | Visual appearance of solution |
|---|---|---|---|---|
| CB2-1 | B5 | 5 | 200 | clear |
| CB3-1 | B6 | 7 | 200 | clear |

Example CB4: Preparation of Co-polyamino Acid/Insulin Glargine/Insulin Lispro Compositions at pH 7.2

Co-polyamino acid/75 U/ml insulin glargine/25 U/ml insulin lispro compositions are prepared according to the method described in example CB4.

TABLE 2a

Insulin glargine (75 U/mL) and insulin lispro (25 U/ml) compositions in the presence of co-polyamino acids.

| Composition | Co-polyamino acid | Co-polyamino acid concentration (in mg/ml) | [ZnCl$_2$] (mM) | [NaCl] (mM) | Visual appearance of solution |
|---|---|---|---|---|---|
| CB4-1 | B23 | 3.1 | 0.5 | 0 | Clear |
| CB4-2 | B23 | 2.6 | 0.5 | 10 | Clear |
| CB4-3 | B23 | 2.0 | 1 | 10 | Clear |
| CB4-4 | B23 | 1.5 | 0.7 | 10 | Clear |
| CB4-5 | B14 | 1.5 | 0.5 | — | Clear |
| CB4-6 | B14 | 1.4 | 0.5 | 5 | Clear |
| CB4-7 | B26 | 2.0 | 0.5 | — | Clear |
| CB4-8 | B9 | 1.5 | 0.5 | — | Clear |
| CB4-9 | B6 | 2.6 | 0.5 | — | Clear |
| CB4-10 | CE1 | 2.0 | 0.5 | — | Clear |
| CB4-11 | CE2 | 2.0 | 0.5 | — | Clear |

Example CB5: Preparation of a Co-Polyamino Acid B23/Insulin Glargine/Insulin Lispro Composition at pH 7.2

Co-polyamino acid/150 U/ml insulin glargine/50 U/ml insulin lispro compositions are prepared according to the method described in example CB5.

TABLE 2b

Insulin glargine (150 U/mL) and insulin lispro (50 U/ml) compositions in the presence of co-polyamino acid B23.

| Composition | Co-polyamino acid | Co-polyamino acid concentration (in mg/ml) | [ZnCl$_2$] (mM) | [NaCl] (mM) | Visual appearance of solution |
|---|---|---|---|---|---|
| CB5-1 | B23 | 3.1 | 1.4 | 10 | Clear |

Co-polyamino acid B23 enables the solubilization of insulin glargine in the presence of insulin lispro at neutral pH and lead to a clear solution.

Part CD—Results

Demonstration of Physical Stability of Compositions

Example CD1: Accelerated Stability at 25° C. under Dynamic Conditions

3×3 mL vials filled with 1 mL of co-polyamino acid/insulin glargine or co-polyamino acid/insulin glargine/prandial insulin composition are placed vertically on an orbital stirrer. The stirrer is placed in an oven at 25° C. and the vials are placed under stirring at 250 rpm. The vials are inspected visually daily/weekly in order to detect the appearance of visible particles or turbidity. This inspection is carried out according to the recommendations of the European Pharmacopeia (EP 2.9.20): the vials are placed under lighting of at least 2000 Lux and are observed against a white background and a black background. The number of days of stability corresponds to the period from which at least 2 vials exhibit visible particles or are turbid.

The accelerated stability result with co-polyamino acid B5 is shown in Table 3.

TABLE 3

Stability result of co-polyamino acid B5/insulin glargine (200 U/mL)/insulin lispro (66 U/mL) composition at 25° C. under dynamic conditions.

| Composition | Co-polyamino acid | Co-polyamino acid concentration (in mg/ml) | Insulin glargine (U/mL) | Insulin Lispro (U/mL) | Stability in days |
|---|---|---|---|---|---|
| CB2-1 | B5 | 5 | 200 | 66 | >10 |

Example CD2: Accelerated Stability at 30° C. under Static Conditions

At least 5×3 mL cartridges filled with 1 mL of co-polyamino acid/insulin glargine/prandial insulin composition are placed in an oven at 30° C. under static conditions. The cartridges are inspected visually twice monthly in order to detect the appearance of visible particles or turbidity. This inspection is carried out according to the recommendations of the European Pharmacopeia (EP 2.9.20): the vials are placed under lighting of at least 2000 Lux and are observed against a white background and a black background. The number of weeks of stability corresponds to the period from which the majority of the cartridges exhibit visible particles or are turbid.

The accelerated stability results under static conditions are shown in Table 4.

TABLE 4

Stability results of co-polyamino acid/insulin glargine insulin lispro compositions at 30° C. under static conditions.

| Composition | Co-polyamino acid | Co-polyamino acid concentration (mg/ml) | [ZnCl$_2$] (mM) | [NaCl] (mM) | Stability (week) |
|---|---|---|---|---|---|
| CB4-1 | B23 | 3.1 | 0.5 | 0 | >17 |
| CB4-2 | B23 | 2.6 | 0.5 | 10 | >17 |
| CB4-3 | B23 | 2.0 | 1 | 10 | >17 |
| CB4-5 | B14 | 1.5 | 0.5 | — | >23 |
| CB4-7 | B26 | 2.0 | 0.5 | — | >6 |

Co-polyamino acids B23, B14, B26 enable the solubilization of insulin glargine in the presence of insulin lispro at neutral pH and lead to a composition having good physical stability. Adding salt and zinc to the compositions comprising co-polyamino acid B23 enable maintaining good physical stability while using a reduced co-polyamino acid B23 concentration.

Example CD3: Precipitation of Insulin Glargine after Mixing Co-polyamino Acid/75 U/mL Insulin Glargine/25 U/mL Insulin Lispro Compositions in a Simulated Physiological Medium This test demonstrates the precipitation of insulin glargine following injection in a simulated physiological medium at physiological pH and ionic strength and containing albumin. These conditions help imitate the behavior of the composition following subcutaneous injection. To 100 µL of co-polyamino acid/75 U/ml insulin glargine/25 U/ml insulin lispro are added 100 µL of a 20 mg/mL bovine albumin solution in phosphate buffer at pH 7.4. The phosphate buffer (PBS or phosphate buffer saline) is concentrated such that the NaCl and phosphate contents are 140 mM and 10 mM respectively following mixing with the composition. The precipitation of glargine in this medium is followed at ambient temperature (20-25° C.) by absorbance measurements at 450 nm of the mixtures for 30 minutes. The absorbance measurements are made using a UV-visible multi-well plate reader.

The absorbance increases until it reaches a plateau. The precipitation time of glargine is defined as the time required for the absorbance measured to be greater than or equal to 80% of the value of the plateau.

TABLE 5

Precipitation time of insulin glargine after mixing the co-polyamino acid/insulin glargine/insulin lispro compositions to a medium simulating the subcutaneous medium.

| Composition | Co-polyamino acid | Co-polyamino acid concentration (in mg/ml) | Precipitation time (minute) |
|---|---|---|---|
| CB4-1 | B23 | 3.1 | 2 |
| CB4-2 | B23 | 2.6 | 3 |

TABLE 5-continued

Precipitation time of insulin glargine after mixing the co-polyamino acid/insulin glargine/insulin lispro compositions to a medium simulating the subcutaneous medium.

| Composition | Co-polyamino acid | Co-polyamino acid concentration (in mg/ml) | Precipitation time (minute) |
|---|---|---|---|
| CB4-5 | B14 | 1.5 | 2 |
| CB4-8 | B9 | 1.5 | 2 |
| CB4-9 | B6 | 2.6 | 3 |
| CB4-10 | CE1 | 2.0 | 4 |
| CB4-11 | CE2 | 2.0 | 4 |
| CB4-4 | B23 | 1.5 | 1 |

The co-polyamino acid/insulin glargine/insulin lispro compositions according to the invention result in rapid precipitation of glargine after mixing with a medium simulating the subcutaneous medium.

Part D Pharmacokinetics

D1: Pharmacokinetic measurement protocol of insulin glargine and insulin lispro formulations.

Studies on dogs were conducted with a view to evaluating the pharmacokinetics of insulins after administering a co-polyamino acid B23/insulin glargine (150 U/mL)/insulin lispro (50 U/mL) composition.

The pharmacokinetic profiles of insulin glargine (sum of the circulating concentration of insulin glargine and of the main metabolite M1 thereof) and of insulin lispro were obtained for this composition.

Ten animals placed under fasting conditions for about 17.5 hours were injected by the subcutaneous route at a dose of 0.68 U/kg of insulin. Blood samples are taken for the 16 h following administration to describe the pharmacokinetics of the insulins. The levels of glargine, glargine-M1 and lispro are determined by means of a specific bioanalysis method.

The pharmacokinetic parameters determined are as follows:

$AUC_{0-1\,h}$, $AUC_{0-2\,h}$, $AUC_{10-16\,h}$, $AUC_{13-16\,h}$ corresponding to the area under the curve of the concentrations of insulin glargine (and the metabolite M1 thereof) as a function of time from 0 to 1 h, 0 and 2 h, 10 and 16 h and 13 and 16 h post-administration, respectively;

$AUC_{0-30\,mm}$, $AUC_{0-1\,h}$, $AUC_{8-16\,h}$ corresponding to the area under the curve of the concentrations of insulin lispro as a function of time from 0 to 0.5 h, 0 and 1 h and 8 and 16 h post-administration, respectively;

$AUC_{last}$ corresponding to the area under the curve from the time 0 to the last measurement time performed on the subject.

Table 6 hereinafter reports different pharmacokinetic parameters of insulin glargine and insulin lispro.

TABLE 6

Mean pharmacokinetic parameters (ratio of means) of composition CB5-1 comprising co-polyamino acid B23/150 U/mL insulin glargine/50 U/mL insulin lispro.

| | Insulin glargine (150 U/mL) | | | | Insulin Lispro (50 U/mL) | | |
|---|---|---|---|---|---|---|---|
| | $AUC_{0-1\,h}/$ $AUC_{last}$ (%) | $AUC_{0-2\,h}/$ $AUC_{last}$ (%) | $AUC_{10-16\,h}/$ $AUC_{last}$ (%) | $AUC_{13-16\,h}/$ $AUC_{last}$ (%) | $AUC_{0-30\,min}/$ $AUC_{last}$ (%) | $AUC_{0-1\,h}/$ $AUC_{last}$ (%) | $AUC_{8-16\,h}/$ $AUC_{last}$ (%) |
| CB5-1 | 19.6 | 28.7 | 19.8 | 8.2 | 25.4 | 48.0 | 3.5 |

The results obtained demonstrate that, on one hand, the glargine component of the formulation is absorbed rapidly ($AUC_{0-1\,h}$ and $AUC_{0-2\,h}$) while retaining the basal properties thereof with a significant coverage at the end part of the observation time ($AUC_{10-16\,h}$ and $AUC_{13-16\,h}$).

Furthermore, the lispro component is rapidly absorbed ($AUC_{0-30\,min}$ and $AUC_{0-1\,h}$) and retains the prandial properties thereof. Indeed, lispro is no longer observed after 8 h ($AUC_{8-16\,h}$).

The invention claimed is:

1. A composition in the form of an injectable aqueous solution, wherein the pH is comprised from 6.0 to 8.0, comprising at least:
   a basal insulin which isoelectric point pI is comprised from 5.8 to 8.5;
   a co-polyamino acid comprising glutamic or aspartic units that is a co-polyamino acid according to formula I:

$[Q(PLG)_k][Hy]_j[Hy]_{j'}$  Formula I wherein:
   $j \geq 1$; $0 \leq j' \leq n'1$ and $j+j' \geq 1$ and $k=2$,
   Q is $Q[*]_k$, wherein $Q[*]_k$ is a divalent linear or branched radical or spacer $([Q']_q)[*]_k$, where * represents binding sites of the different represented elements, $1 \leq q \leq 5$ and $k=2$,
   wherein Q' is a radical selected from the group consisting of formula III and formula IV and forms $([Q']_q)[*]_k$:

$*\!-\!\!F_a\!-\!\!(CH_2)_l\!-\!\!F_{a'}\!-\!\!*$  Formula III

Formula IV

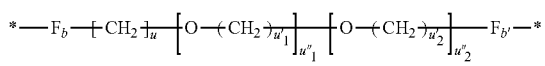

wherein:
1≤t≤8,
at least one of $u_1''$ or $u_2''$ is other than 0,
if $u_1''\neq 0$ then $u_1'\neq 0$ and if $u_2''\neq 0$ then $u_2'\neq 0$,
$u_1'$ and $u_2'$ are identical or different,
2≤u≤4,
0≤$u_1'$≤4,
0≤$u_1''$≤4,
0≤$u_2'$≤4,
0≤$u_2''$≤4, and
Fa, Fb, Fa', and Fb' are identical or different and each represents function —NH— or —CO,
the co-polyamino acid according to formula I bearing at least one hydrophobic radical -Hy, carboxylate charges and two chains of glutamic or aspartic units PLG bound together by the divalent linear or branched radical or spacer,
the divalent linear or branched radical or spacer being bound to two glutamic or aspartic unit chains PLG by an amide function and,
the amide function binding the divalent linear or branched radical or spacer to the two chains of glutamic or aspartic units results from a reaction between an amine function and an acid function respectively borne either by the Q' that forms the divalent linear or branched radical or spacer or by a glutamic or aspartic unit, and
the hydrophobic radical -Hy being bound either to a terminal amino acid unit and then j≥1, or to a carboxyl function borne by one of the chains of the glutamic or aspartic units PLG and then j'=n'1 and n'1 is the mean number of monomeric units bearing a hydrophobic radical -Hy,
wherein the hydrophobic radical -Hy is a radical according to formula X:

Formula X

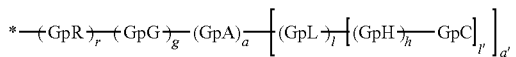

wherein
GpR is selected from the group consisting of radicals according to formulas VII, VII' and VII":

Formula VII

*—N(H)—N—N(H)—*  or

Formula VII'

*—C(O)—R—N(H)—*  or

Formula VII"

*—C(O)—R—C(O)—*;

GpG and GpH are identical or different and selected from the group consisting of radicals according to formulas XI and XI':

Formula XI

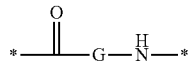

Formula XI'

*—NH—G—NH—*

GpA is a radical according to formula VIII:

Formula VIII

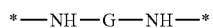

wherein A' is selected from the group consisting of radicals according to formulas VIII', VIII" and VIII"':

Formula VIII'

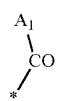

Formula VIII"

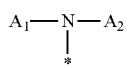

Formula VIII"'

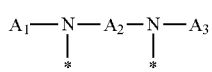

GpL is a radical according to formula XII:

Formula XII

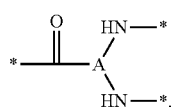

GpC is a radical according to formula IX:

Formula IX

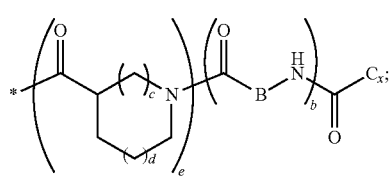

the * indicates the binding sites of the different represented elements bound by amide functions;
a is an integer equal to 0 or to 1 and a'=1 if a=0 and a'=1, 2 or 3 if a=1:
a' is an integer equal to 1, to 2 or to 3;
b is an integer equal to 0 or to 1;
c is an integer equal to 0 or to 1, and if c is equal to 0 then d is equal to 1 or to 2;
d is an integer equal to 0, to 1 or to 2;

e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
r is an integer equal to 0, to 1 or to 2, and
s' is an integer equal to 0 or 1;
A, $A_1$, $A_2$ and $A_3$ identical or different are linear or branched alkyl radicals comprising from 1 to 8 carbon atoms and/or substituted by a radical from a saturated, unsaturated or aromatic ring;
B is a radical selected from the group consisting of a non-substituted ether comprising from 4 to 14 carbon atoms and from 1 to 5 oxygen atoms, non-substituted polyether radical comprising from 4 to 14 carbon atoms and from 1 to 5 oxygen atoms, a linear alkyl radical comprising from 1 to 9 carbon atoms, a branched alkyl radical comprising from 1 to 9 carbon atoms, a linear alkyl radical comprising an aromatic nucleus and comprising from 1 to 9 carbon atoms, and a branched alkyl radical comprising an aromatic nucleus and comprising from 1 to 9 carbon atoms:
$C_x$ is a linear or branched monovalent alkyl radical, and/or comprising a cyclic part, wherein x indicates the number of carbon atoms and:
when the hydrophobic radical -Hy bears 1-GpC, then $9 \leq x \leq 25$,
when the hydrophobic radical -Hy bears 2-GpC, then $9 \leq x \leq 15$,
when the hydrophobic radical -Hy bears 3-GpC, then $7 \leq x \leq 13$,
when the hydrophobic radical -Hy bears 4-GpC, then $7 \leq x \leq 11$,
when the hydrophobic radical -Hy bears 5 or more -GpC, then $6 \leq x \leq 11$,
G is a branched alkyl radical of 1 to 8 carbon atoms, the alkyl radical bearing one or a plurality of free carboxylic acid function(s);
R is a radical selected from the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ and a non-substituted ether or polyether radical comprising from 4 to 14 carbon atoms and from 1 to 5 oxygen atoms;
the hydrophobic radical(s) -Hy according to formula X being bound to the PLG:
via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, or
via a covalent bond between a nitrogen atom of the hydrophobic radical -Hy and a carbonyl borne by the PLG thus forming an amide function obtained from the reaction of an amine function of a precursor -Hy' of the hydrophobic radical -Hy and an acid function borne by a PLG,
a ratio M between the number of hydrophobic radicals and the number of glutamic or aspartic units being between $0 < M \leq 0.5$;
when a plurality of hydrophobic radicals are borne by a co-polyamino acid then they are identical or different;

a degree of polymerization DP in glutamic or aspartic units for the PLG chains is comprised from 5 to 250; and
free carboxylic acid functions are in a form of alkali cation salt selected from the group consisting of $Na^+$ and $K^+$.

2. The composition according to claim 1, wherein the co-polyamino acid bearing carboxylate charges and at least one hydrophobic radical -Hy is a co-polyamino acid according to formula XXXb:

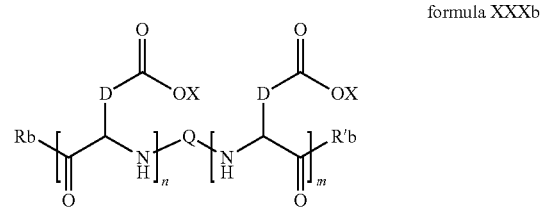

formula XXXb wherein,
D represents, independently, either a group —$CH_2$— (aspartic acid) or a group —$CH_2$—$CH_2$— (glutamic acid),
X represents a cationic entity selected from the group consisting of alkali cations,
Rb and R'b, which are identical or different, are either a hydrophobic radical -Hy, or a radical selected from the group consisting of an OH, an amino group, a terminal amino acid unit and a pyroglutamate,
at least one of Rb and R'b being a hydrophobic radical -Hy,
Q and Hy are as defined above,
n+m represents the degree of polymerization DP of the co-polyamino acid, namely the mean number of monomeric units per co-polyamino acid chain and $5 \leq n+m \leq 250$.

3. The composition according to claim 1, wherein the co-polyamino acid bearing carboxylate charges and at least one hydrophobic radical -Hy is a co-polyamino acid according to formula XXXa hereinafter:

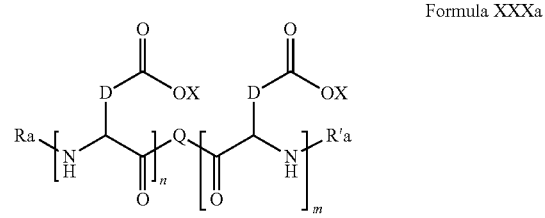

Formula XXXa wherein,
D represents, independently, either a group —$CH_2$— (aspartic acid) or a group —$CH_2$—$CH_2$— (glutamic acid),
X represents a cationic entity selected from the group consisting of alkali cations,
Ra and R'a, which are identical or different, are either a hydrophobic radical -Hy, or a radical selected from the group consisting of an H, a C2 to C10 linear acyl group, a C3 to C10 branched acyl group, a benzyl, a terminal amino acid unit and a pyroglutamate, at least one of Ra and R'a being a hydrophobic radical -Hy, Q and -Hy are as defined in Formula I, n+m represents the degree of polymerization DP of the co-polyamino acid, namely the mean number of monomeric units per co-polyamino acid chain and $5 \leq n+m \leq 250$.

4. The composition according to claim 1, wherein the co-polyamino acid bearing carboxylate charges and at least one hydrophobic radical -Hy is a co-polyamino acid according to formula XXXb':

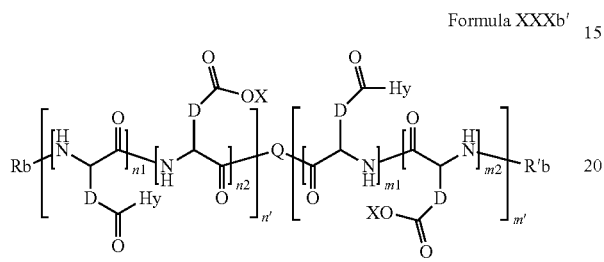

Formula XXXb' wherein:

D represents, independently, either a group —CH$_2$— (aspartic acid) or a group —CH$_2$—CH$_2$— (glutamic acid), X represents a cationic entity selected from the group consisting of alkali cations, Q and Hy are as defined in Formula I, Rb and R'b, which are identical or different, are either a hydrophobic radical -Hy, or a radical selected from the group consisting of an —OH, an amine group, a terminal amino acid unit and a pyroglutamate, at least one of Rb and R'b is a hydrophobic radical -Hy, n1+m1 represents the number of glutamic units or aspartic units of the PLG chains of the co-polyamino acid bearing a radical -Hy, n2+m2 represents the number of glutamic units or aspartic units of the PLG chains of the co-polyamino acid not bearing a radical -Hy, n1+n2=n' and m1+m2=m', n'+m' represents the degree of polymerization DP of the co-polyamino acid, namely the mean number of monomeric units per co-polyamino acid chain and $5 \leq n'+m' \leq 250$.

5. The composition according to claim 1, wherein the co-polyamino acid bearing carboxylate charges and at least one hydrophobic radical -Hy is a co-polyamino acid according to formula XXXa' hereinafter:

Formula XXXa' wherein:

D represents, independently, either a group —CH$_2$— (aspartic acid) or a group —CH$_2$—CH$_2$— (glutamic acid), X represents a cationic entity selected from the group consisting of alkali cations, Ra and R'a, which are identical or different, are either a hydrophobic radical -Hy, or a radical selected from the group consisting of an H, a C2 to C10 linear acyl group, a C3 to C10 branched acyl group, a benzyl, a terminal amino acid unit and a pyroglutamate, and at least one of Ra and R'a is hydrophobic radical -Hy, Q and Hy are as defined in Formula I, n$_1$+m$_1$ represents the number of glutamic units or aspartic units of the PLG chains of the co-polyamino acid bearing a radical -Hy, n$_2$+m$_2$ represents the number of glutamic units or aspartic units of the PLG chains of the co-poly amino acid not bearing a radical -Hy, n$_1$+n$_2$=n' and m$_1$+m$_2$=m'.

6. The composition according to claim 1, wherein the co-polyamino acid bearing carboxylate charges and hydrophobic radicals is a co-polyamino acid selected from the group according to formulas XXXa, XXXa', XXXb and XXXb':

Formula XXXa

Formula XXXa'

Formula XXXb

Formula XXXb' wherein the group D is a group —CH$_2$— (aspartic unit),

X represents a cationic entity selected from the group consisting of alkali cations, Ra and R'a, which are identical or different, are either a hydrophobic radical -Hy, or a radical selected from the group consisting of an a C2 to C10 linear acyl group, a C3 to C10 branched acyl group, a benzyl, a terminal amino acid unit and a pyroglutamate, and at least one of Ra and R'a is a hydrophobic radical -Hy, Rb and R'b, which are identical or different, are either a hydrophobic radical -Hy, or a radical selected, from the group consisting of an —OH, an amine group, a terminal amino acid unit and a pyroglutamate, at least one of Rb and R'b is a hydrophobic radical -Hy, Q and Hy are as defined in Formula I, n1+m1 represents the number of glutamic units or aspartic units of the PLG chains of the co-polyamino acid bearing a radical -Hy, n2+m2 represents the number of glutamic units or aspartic units of the PLG chains of the co-polyamino acid not bearing a radical -Hy, n1+n2=n' and m1+m2=m', and n'+m' represents the degree of polymerization DP of the co-polyamino acid, namely the mean number of monomeric units per co-polyamino acid chain and $5 \leq n'+m' \leq 250$.

7. The composition according to claim 1, wherein the co-polyamino acid bearing carboxylate charges and hydrophobic radicals is a co-polyamino acid selected from the group according to formulas XXXa, XXXa', XXXb or XXXb':

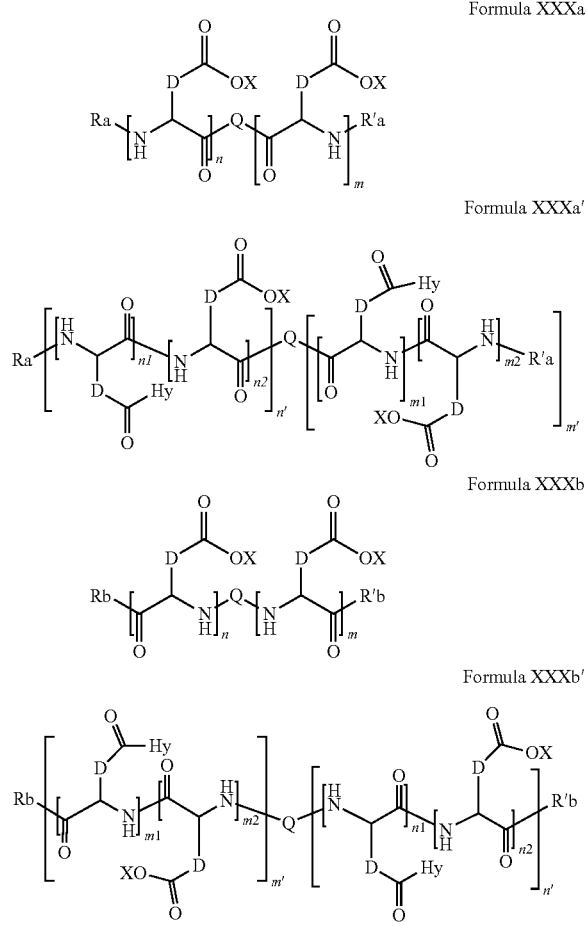

Formula XXXa

Formula XXXa'

Formula XXXb

Formula XXXb' wherein the group D is a group —CH$_2$—CH$_2$— (glutamic unit),

X represents a cationic entity chosen from the group consisting of alkali cations, Ra and R'a, which are identical or different, are either a hydrophobic radical -Hy, or a radical selected from the group consisting of an H, a C2 to C10 linear acyl group, a C3 to C10 brandied acyl group, a benzyl, a terminal amino acid unit and a pyroglutamate, and at least one Ra and R'a is a hydrophobic radical -Hy, Rb and R'b, which are identical or different, are either a hydrophobic radical -Hy, or a radical selected from the group consisting of an —OH, an amine group, a terminal amino acid unit and a pyroglutamate, at least one of Rb and R'b is a hydrophobic radical -Hy, Q and Hy are as defined in Formula n1+m1 represents the number of glutamic units or aspartic units of the PLG chains of the co-polyamino acid bearing a radical -Hy, n2+m2 represents the number of glutamic units or aspartic units of the PLG chains of the co-polyamino acid not bearing a radical -Hy, n1+n2=n' and m1+m2=m', and n'+m' represents the degree of polymerization DP of the co-polyamino acid, namely the mean number of monomeric units per co-polyamino acid chain and $5 \leq n'm' \leq 250$.

8. The composition according to claim 1, wherein the basal insulin which isoelectric point is comprised from 5.8 to 8.5 is insulin glargine.

9. The composition according to claim 1, wherein it comprises from 40 to 500 U/mL of basal insulin which isoelectric point is comprised from 5.8 to 8.5.

10. The composition according to claim 1, wherein the concentration of co-polyamino acid bearing carboxylate charges and hydrophobic radicals is not more than 60 mg/mL.

11. The composition according to claim 1, wherein the concentration of co-polyamino acid bearing carboxylate charges and hydrophobic radicals is not more than 40 mg/mL.

12. The composition according to claim 1, wherein the concentration of co-polyamino acid bearing carboxylate charges and hydrophobic radicals is not more than 20 mg/mL.

13. The composition according to claim 1, wherein the concentration of co-polyamino acid bearing carboxylate charges and hydrophobic radicals is not more than 10 mg/mL.

14. A co-polyamino acid bearing carboxylate charges and at least one hydrophobic radical according to formula X, according to formula I:

$$[Q(PLG)_k][Hy]_j[Hy]_{j'} \quad \text{Formula I}$$

wherein:

j≥1; 0≤j'≤n'1 and j+j'≥1 and k=2,

Q is $Q[*]_k$ is, wherein $Q[*]_k$ is a divalent linear or branched radical or spacer $([Q']_q[*]_k)$, where * represents binding sites of the different represented elements, $1 \leq q \leq 5$ and k=2, wherein Q' is of formula III and forms $([Q']_q[*]_k)$:

Formula III wherein 1≤t≤8, and

Fa and Fa' are identical or different and each represents function or —CO, said co-polyamino acid according to formula I bearing at least one hydrophobic radical -Hy, carboxylate charges and two chains of glutamic or aspartic units PLG bound together by the divalent linear or branched radical or spacer, the divalent linear or branched radical or spacer being bound to two glutamic or aspartic unit chains PLG by an amide function and, the amide function binding the divalent linear or branched radical or spacer to the two chains of glutamic or aspartic units results from a reaction between an amine function and an acid function respectively borne either by the Q' that forms the divalent linear or branched radical or spacer or by a glutamic or aspartic unit, the hydrophobic radical -Hy being bound either to a terminal amino acid unit and then j≥1, or to a carboxyl function borne by one of the chains of the glutamic or aspartic units PLG and then j'=n'1 and n'1 is the mean number of monomeric units bearing a hydrophobic radical -Hy, and wherein the at least one hydrophobic radical -Hy according to formula X is as defined hereinafter:

$$H-[(GpR)_{\overline{g}}-(GpG)_{\overline{g}}-(GpA)_a-[(GpL)_{\overline{l}}+(GpH)_{\overline{h}}-GpC]_{l'}]_{a'} \quad \text{Formula X'}$$

wherein

GpR is selected from the group consisting of radicals according to formulas VII, VII' and VII":

$$*-\overset{H}{N}-R-\overset{H}{N}-* \quad \text{or} \quad \text{Formula VII}$$

$$*-\overset{O}{\underset{\|}{C}}-R-\overset{H}{N}-* \quad \text{or} \quad \text{Formula VII'}$$

$$*-\overset{O}{\underset{\|}{C}}-R-\overset{O}{\underset{\|}{C}}-*; \quad \text{Formula VII''}$$

GpG and GpH are identical or different and are selected from the group consisting of radicals according to formulas XI and XI':

$$*-\overset{O}{\underset{\|}{C}}-G-\overset{H}{N}-* \quad \text{Formula XI}$$

$$*-NH-G-NH-* \quad \text{Formula XI'}$$

GpA is a radical according to formula VIII $$*-NH-\underset{*}{A'}-[NH-]_{s'}* \quad \text{Formula VIII}$$

wherein A' is selected from the group consisting of radicals according to VIII', VIII" or VIII'''

$$\underset{*}{\overset{A_1}{\underset{\diagdown}{CO}}} \quad \text{Formula VIII'}$$

$$A_1-\underset{*}{N}-A_2 \quad \text{Formula VIII''}$$

$$A_1-\underset{*}{N}-A_2-\underset{*}{N}-A_3 \quad \text{Formula VIII'''}$$

GpL is a radical according to formula XII $$*-\overset{O}{\underset{\|}{C}}-A\overset{HN-*}{\underset{HN-*}{\diagdown}}, \quad \text{Formula XII}$$

GpC is a radical according to formula IX:

Formula IX the * indicates the binding sites of the different groups bound by the amide function;

a is an integer equal to 0 or to 1 and a'=1 if a=0 and a'=2 or 3 if a=1;

a' is an integer equal to 1, to 2 or to 3;

h is an integer equal to 0 or to 1;

c is an integer equal to 0 or to 1, and if c is equal to 0 then d is equal to 1 or to 2;

d is an integer equal to 0, to 1 or to 2;

e is an integer equal to 0 or to 1;

g is an integer equal to 0, to 1, to 2, to 3 to 4 to 5 or to 6;

h is an integer equal to 0, to 1, to 2, to 3 to 4 to 5 or to 6;

l is an integer equal to 0 or 1 and l'=1 if l=0 and l'=2 if l=1;

r is an integer equal to 0, to 1 or to 2, and s' is an integer equal to 0 or 1;

A, $A_1$, $A_2$ and $A_3$ identical or different are linear or branched alkyl radicals comprising from 1 to 8 carbon atoms and/or substituted by a radical from a saturated, unsaturated or aromatic ring;

B is a radical selected from the group consisting of a non-substituted ether comprising from 4 to 14 carbon atoms and from 1 to 5 oxygen atoms, a non-substituted polyether radical comprising from 4 to 14 carbon atoms and from 1 to 5 oxygen atoms, a linear alkyl radical comprising from 1 to 9 carbon atoms, a branched alkyl radical comprising from 1 to 9 carbon atoms, a linear alkyl radical comprising an aromatic nucleus and comprising from 1 to 9 carbon atoms, and a branched alkyl radical comprising an aromatic nucleus and comprising from 1 to 9 carbon atoms;

$C_x$ is a linear or branched monovalent alkyl radical, optionally comprising a cyclic part, wherein x indicates the number of carbon atoms and:
  when the hydrophobic radical -Hy bears 1-GpC, then $9 \leq x \leq 25$,
  when the hydrophobic radical -Hy bears 2-GpC, then $9 \leq x \leq 15$,
  when the hydrophobic radical -Hy bears 3-GpC, then $7 \leq x \leq 13$,
  when the hydrophobic radical -Hy bears 4-GpC, then $7 \leq x \leq 11$,
  when the hydrophobic radical -Hy bears 5 or more -GpC, then $6 \leq x \leq 11$, G is a branched alkyl radical of 1 to 8 carbon atoms, said alkyl radical bearing one or a plurality of free carboxylic acid function(s); and R is a radical selected from the group consisting of a linear or branched, divalent alkyl radical comprising from 1 to 12 carbon atoms, a linear or branched, divalent alkyl radical comprising from 1 to 12 carbon atoms bearing one or a plurality of functions $CONH_2$, and a non-substituted ether or polyether radical comprising from 4 to 14 carbon atoms and from 1 to 5 oxygen atoms.

15. A method for improving the physicochemical stability of the composition according to claim 1, by adding one or more ionic species selected from the group of anions, cations and zwitterions.

* * * * *